United States Patent
Peters et al.

(10) Patent No.: US 8,603,742 B2
(45) Date of Patent: Dec. 10, 2013

(54) METHODS FOR THE DIAGNOSIS OF FETAL DISEASE

(75) Inventors: David G. Peters, Pittsburgh, PA (US); Tianjiao Chu, Wexford, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/177,381

(22) Filed: Jul. 6, 2011

(65) Prior Publication Data

US 2012/0065076 A1   Mar. 15, 2012

Related U.S. Application Data

(60) Provisional application No. 61/361,824, filed on Jul. 6, 2010.

(51) Int. Cl.
- *C12Q 1/68* (2006.01)
- *C12P 19/34* (2006.01)
- *C07H 21/02* (2006.01)

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

2011/0039724 A1   2/2011   Lo et al.

OTHER PUBLICATIONS

Chim S.S.C. et al. Clinical Chemistry 54:3, 500-511 (2008).*
dbSNP Submitted SNP (ss) Details for ss75234511, Aug. 28, 2007, from www.ncbi.nlm.nih.gov, p. 1.*
Chu et al., "A microarray-based approach for the identification of epigenetic biomarkers for the noninvasive diagnosis of fetal disease," *Prenat. Diagn.* 29:1020-1030 (2009).
Papageorgiou et al., "Sites of Differential DNA Methylation between Placenta and Peripheral Blood," *The American Journal of Pathology* 174(5):1609-1618 (May 2009).

* cited by examiner

*Primary Examiner* — Stephen Kapushoc
(74) *Attorney, Agent, or Firm* — Klarquist Sparkman, LLP

(57) ABSTRACT

Methods are provided for detecting an aneuploidy in a fetus. These methods can be used to detect trisomy 13, 8 or 21, amongst other aneupoloidies. In some embodiments, the methods include selectively purifying fetal DNA from a maternal biological sample using the methylation status of a CpG containing genomic sequence and genotyping the fetus using the purified fetal DNA, thereby detecting aneuploidy in the fetus.

15 Claims, 4 Drawing Sheets

SEQUENCE LISTING

```
<160> NUMBER OF SEQ ID NOS: 83

<210> SEQ ID NO 1
<211> LENGTH: 357
<212> TYPE: DNA
<213> ORGANISM: Homo sapiens

<400> SEQUENCE: 1
acaatatgga aaacacagct gtaacccata cacattcaca ccagcacaag cttcttccat      60
ccttcctgga gagagacaaa aacagaagac acagaaagga agggcaggat cagggacagc     120
aggttcgtgg gagggactgt tcgtggggga acccggcagg ggaagaaaga caggaagggg     180
aagaagggga aagagaggaa gtggggtagg gcagagggcc ctgggctgtg cactcccatc     240
tcacacttgt ccccagagca aggtctttaa ggccagactc caacccagga gcagggaggg     300
gggcaaacgc ccctgtagcc gccctgcacc ctcccaggag ggggagcaca ggctgtc        357

<210> SEQ ID NO 2
<211> LENGTH: 266
<212> TYPE: DNA
<213> ORGANISM: Homo sapiens

<400> SEQUENCE: 2
```

```
ccacaacctg tcagaaatgc ccccaagccc aaaggcgtcg agagaatggc caggttgttt      60
cagattgaca catatcctaa tgtacaagtc agcccacaca ccccacgtgc actgagcgtc     120
tcttgttgtt caccccaaat aaactctgcc ggaactgggg cggactcgc aggggcggag      180 aaggggggag acgggcagag ggcagaagtg gatggtgaga agagccaatg gaggggcccc    240
gtgagagtga gcaaggctgc acccct                                          266
```

<210> SEQ ID NO 3
<211> LENGTH: 601
<212> TYPE: DNA
<213> ORGANISM: Homo sapiens

<400> SEQUENCE: 3

```
tgataacact ggggagagtt aactttttca cctctgtttg ttgatatgcc cctttgtgct      60
ccgtattcac aaagggggcac ctcaacaagc ccatcatttg ttaatgaatg cctttacttt    120
catcgccagc aagacatttt cataaaccca ccatctactt tgcagttctc aagagttgct    180
tctcttaaac tggtgaggac gcggctaagc cctggaaatg agtccagatt ctcacggtgg    240
cccataaaca ctgctgtttc ctcccaccta ggaaacccgc agacctgcag aacctggctc    300
ccggaacaaa ccctccttc atgacttttg atggtgaagt caagacggat gtgaataaga    360
tcgaggagtt cttagaggag aaattagctc ccccgaggta ggcctcagaa accagtgtt    420 cataacttga ttgtcacttt cccccactag tagtcagttc taaagctctg gcagtgtgt    480 gtgtgtgtgg ttttctgcag cccacggtgc tcacttcctt aatcataacc ctggtgtaac    540
cagattagag ttcggggacc tgggtttcat tgtgctgcac ctgcagcttg gcaatcacag    600
t                                                                     601
```

<210> SEQ ID NO 4
<211> LENGTH: 601
<212> TYPE: DNA
<213> ORGANISM: Homo sapiens

<400> SEQUENCE: 4

```
atcagagtcg cccttgacct caaccctgcc cgagaaggaa gtgctggtgc aaccccagcc      60
cagctgcagg aagtggtacc tgtcaccaag tcccctgcac aggggaagca ggggggctgag   120 ggggcaggac caggggggacg aggtcatcct tccccggaga acccctcagg ggccgggcgc   180
ccttccctcc cgggcaccaa atggacacag ctaacaagaa ccacacttca cggtgagcaa    240
agctctgaac attcaggctc tgagacacga aagcggcgtc agaagagacc tgcagcagat    300
ccgggccaaa tcacacacac cctttcacag aagtcgagga caggagaaca ggagcaaaca    360
caggaaagga agaggccagc ctggtggctg acgcctgcaa tcccagtgtt ttgagaggcc    420
aaggcaggag aatcacttga ggccaggagt ttgagagcag cctgggcaac acagtgagac    480
tcctacctct acaaaaaata aaaatagaaa ataaattagc cagacatggt ggcatgcatc    540
tctagtccca gttactcagg aggctgaggc aggaggatca ctcgcgccca ggagggagag    600
a                                                                     601
```

<210> SEQ ID NO 5
<211> LENGTH: 601
<212> TYPE: DNA
<213> ORGANISM: Homo sapiens

<400> SEQUENCE: 5

```
ctctgagatg cgtcgtgtag taaacttctc aataaggcgt agtttatgtt caagagagaa      60
```

```
attctctttg tcacttagca taaaccttgt agctagcttt ctgaatattt gtatctcagt    120
agaagagtta aatgcctcat tcaagtatgt tttcaaaata aaaattgtaa ataaaatcac    180
gtgatgttta tatatgagaa gtcaccagct tttcattcag agttccccg tttctagagg     240 ttggaccagc ctcaatgatc gtggggaacc tggttgctgg aagagaatc gctcaggctt     300 ccgggagaga gctcgcccac ctggaggaca gcgaccaggc acggaaggtg acaggccagt    360
tccggggacg ggtggacggg tgtctgtgcc ccggaggcgc cagtgagcaa gtcgccctct    420
cgtgcagttc ctgttcctgg ctgacgtgct gcagtggcgt gcccacacca ctcctgacca    480
cccgctgttc ttgctgctga acgccaaggt gaggcagtgt cacgcccacg gggcttggaa    540
acacctgtgg gccggtggag cccttttgctt gtctagttca tggtgccagt gtcctggttg    600
t                                                                   601

<210> SEQ ID NO 6
<211> LENGTH: 601
<212> TYPE: DNA
<213> ORGANISM: Homo sapiens

<400> SEQUENCE: 6
aaaatctttt tttttttttt tttttttga gatggagtct cgcttttgtt gcccaggctg     60
gagcgaagtc tcttagtttc ctccccacgg tttcgtgcac tagaccccga agcaggcaag    120
ctgagcatct ttatccccat ttttcagagg aatgactaga agtcagggtt tgcccaaggt    180
caaacaacta gctggttgca agtaagaat tggaagccac ccatgttatt ccttccgcta     240
cacctccctc cagagacagg gctggccagc atcgcacgga acaggaaatt gaaatggctc    300
ccggtaaggc agcgagcctg ccaaccaccg agagaagctg acaagtgacc caaacccgcc    360
cagaatttaa aatgcctcct cagaggagtt gccgactaac ctcctcccac ctgctgcagt    420
gaagaaataa gttccaagag tctgcaaccc accatgcctg ttttttccacg ggaaggacca    480 agttagaaag gaagcttgaa taagtgggat gctgttgaag aactaagatg tagaagcagt    540
ttcccaatat gaacttacta gcttttttcc cactcctatc acatcgccac tcccccaca    600 c                                                                   601

<210> SEQ ID NO 7
<211> LENGTH: 601
<212> TYPE: DNA
<213> ORGANISM: Homo sapiens

<400> SEQUENCE: 7
gctccttttt gggtaaggtc tgttgcttct ctaggaacag tgacggtggc agagcccgtg    60
gcccctctct cctgtcccag agccaagctg tttcctctcc ccactcccgg gcaccctgcg    120
ggcaagtgag gggggcccac tctgccctgg cctgccccac cgccccattt gctgggttgt    180
cctcaaagca cacggtaagc accccgccc cgcccccca cacacgtacc gctgtcagcc     240
ttcttgctcg tcacctccat ccagggcaca tccgcccctc tgggtgctgt gagcctgttg    300
ccggcgcggt cccgctgctc ctccttctgc tgccctgcac tgccgtggca aaccctccc    360 tccgggtctc tgctgagccc tccaggcgct caggtctgcc gtctggttgc aggtgtttta    420
tagagtgcag ctttacgctc ccactccagt catctccacg ttggtgtccg tctgtgtgtc    480
ctctctgcct ttaagttctg cctctgtgtg acacagtttc acagtttctg tgaccaaaac    540
acaggtttag tcgcttgctg ctggcagagt ccaattaaca agagcacgtc gggtataaag    600
a                                                                   601
```

```
<210> SEQ ID NO 8
<211> LENGTH: 124
<212> TYPE: DNA
<213> ORGANISM: Homo sapiens

<400> SEQUENCE: 8
atgtgagaac ccagcaccaa aactgggctc acggatcaac aaaaataacc cgggcctcac    60
cgaccaaaat caagtagaat agcggttggg tcaaaggaga gaaaaatagg cttggttgct   120
aacc                                                                124

<210> SEQ ID NO 9
<211> LENGTH: 601
<212> TYPE: DNA
<213> ORGANISM: Homo sapiens

<400> SEQUENCE: 9
taaatatctg tgagaaatat ttgtgaaagt atattatgga aaaaatggaa tatgcatgta    60
aacttaggct atgttgagta aaataaaact aatgttttaa atatgaagaa atgaacagtt   120
gctcaatgct tgtttctcta cacatgtgca ggaagtatat aattcagtgc tgtacacata   180
tcacattgga gcattaatca cagccgtgtc ccactttacc caaacatggc cacatagtct   240
cttaatccaa gcatttggga actactagc aatcatttag agtggaaaca taatttgaca    300
ccggtttagc attccatttg tttgctacat ccctctttat gacaagaaag gaaaaatca    360 tgtaatacta taatttgagg aaatgtaata atgcattcag ggagacagaa gcaggaaaat   420
tttgcctgtg tagaatattg tcacacatac atgtatgtgt atgtgtatgt atatatcaga   480
aaacatattt caaaaataaa aaagctatgc ttagtatacc ccattgcaaa atcacttcat   540
aatgaaagca cagaccatgt acaacaaata agtgtgacag aaatgagttt ggcaactacc   600
c                                                                   601

<210> SEQ ID NO 10
<211> LENGTH: 601
<212> TYPE: DNA
<213> ORGANISM: Homo sapiens

<400> SEQUENCE: 10
atttacaaca gcaataggta gcaataggtc tcatgacttt acttctctaa tggattgaag    60
aaaaaccagt gaattttaat ttgtcctgcc tttgcttttt gtgaaatgag acaacttac    120 aagcccttca gatattagag ctaatactag aaatcctctg gtgaggtttt tattacttat   180
gttatatttt acaatcacaa attctctatt tgcctctttt aaaaaaatgt tttctaggtg   240
ggagtggtgg ctcaggtaag cagatactgc ctcatgtaac tctctgggta tgactttctc   300
ccggatttaa gggtagcaat aggtctcatg acttcagttc tctaatggat tgaagaaaaa   360
ccagtgaatt ttaaattgtc ctgcctttac tttttgtgaa acgagaacaa cttacaagcc   420
cttcagatgt tggagctaaa actagaaatc tctggtgag atttttatta cttcagttat   480
attttacaat cacaaattct ctatttgcct cttttaaaaa atatttttcta ggtgggagtg   540 gtggctcatg cctgtaatcc cagcactttg ggaggccgag gcgtgcggat cacctgcctg   600
a                                                                   601

<210> SEQ ID NO 11
<211> LENGTH: 601
<212> TYPE: DNA
<213> ORGANISM: Homo sapiens
```

<400> SEQUENCE: 11

```
ttctattcct ttccttataa atccaagcaa tagtttcatt ctttaaaaat gcataatgtg      60
aaaatagcat taggaaagct gccttgaaat atggatacta aatgcatccc actgggcaac     120
ttcagcaaac cgctgggtct tccaccacag ttaaaatagc tcctgctgtc cccggggcag     180
gagtggctta agaaagcatt taatccagga gtgcgtgtct ggagctttgt gttaatcaga     240
ttccatatga ctgaatgacc tttgttttcc ctctggtgga atcgtgaaca tttgggaaaa     300
ccggttttgct tttagtgagt gttgcagggt gcaaatgaaa ctgtattcaa cctaggattc    360
gactgggaga aaacaggag aaaggccaca ggattggtgc aaggacagca ggtcagtgtc      420
aggggctagg tgactgggga gaaagcttgc tgtcccctct gagtgtcctc ccccaaacct     480
cagcgtcccc ccttgggaac ccataccatg gccccgggca acagaggcag caacacaaat    540
aaatagaaga actgtttcat taaaacctcc tccagacaag gccagctctg gatgcagtct    600
t                                                                    601
```

<210> SEQ ID NO 12
<211> LENGTH: 601
<212> TYPE: DNA
<213> ORGANISM: Homo sapiens

<400> SEQUENCE: 12

```
gatggtgaac tgtgttctgg cggacttatt tttaatatac caattgtgtg tagcacaata      60
gtcatttcat aaaaggtctt caatgtgttg taatcactga atgggaaata aatttccatc     120
ctcttttgaa gggtgcattt gtgatgttat acttgctgca tattgtggta acaagcagtc     180
attcccaaaa atgaacatga ccctatttca taacaggata ttgattttgc atgcttaaat    240
taagtttgta tttattatta ctatatatct ctccagttag tttccatttt tacttctaat    300
ccggttaaaa acttactata ttttaaaaat actctctgct atagccatct aattatttaa    360
aatagaatct caggttatta ggcagtgcat tgcttcctac atccaaattt gagcttgaac    420
attttgctaa ctcttttgga attcaatttc cagtttactc acctctgaag aagtatggat    480
tacttgactt gttcactaac tttagtagaa ttagaactca cactcatgtg tcctaacatc    540
aaattttcat tgaagatcat gtgctgcatg acctatacag atggtcccca acttgagatg    600
g                                                                    601
```

<210> SEQ ID NO 13
<211> LENGTH: 601
<212> TYPE: DNA
<213> ORGANISM: Homo sapiens

<400> SEQUENCE: 13

```
tttgcaaaga attctctaag aaagacattt tcctgctttc gtttctgttt catgctgggt      60
aatgttggca agaattattc atggcacatg tgagcaattc aaagaaatat tgtaaaaaaa     120
aaaaaaaaaa caaggcagct ttgcagaggt gcgctatctg cttgatgact tggcatgctg     180
cctctggtgc ttggcatagc accctagctg ctggcacagg ggaagttaca tatacttgcc    240
attgggcctc tactatgcta cctgctgtgc acgatcaata tcaaccaact gcataaacaa    300
ccggatgaac cttgtatctg agggacagca aatagcattt gaattatttt acataaatct   360
gaaaatgtaa tagcggttga tgttcctatt agtattatat ctgagcacga tgatcataat   420
tgagtaacat taaatttagt ttattgaaca gcagtccact gcccggttta ctgtgactac   480
gatctgtgta atgaaaccag caatatgaaa aattctctca gttggtacac ttcctggaga  540
```

```
ggagccaaag tatttattgc tatttgtgca attaatggcc gtatcgattt cttttttttc    600
t                                                                    601

<210> SEQ ID NO 14
<211> LENGTH: 401
<212> TYPE: DNA
<213> ORGANISM: Homo sapiens

<400> SEQUENCE: 14
tcaacaatat aaattagttt ctgagatgcg cagataaatt aaaattccat gcaggtgacc     60
atagacatac ccctactatg tgtatctgtc taaactataa ccggagagga ctacaattaa    120
tcccttaagc cctttatctt cttttcgtct cctgcttggt tctacgtaaa cacctttgct    180
gaactggaag atccaaccaa cttatacgag cttcttggat gcgaatgaaa acctcgtgaa    240
ttgcccagca agttgacatt cctttctaga tccagcacat acaactctct ccaggtgagc    300
acaaagaaag aagagatttg aagtcagcga ggtgcgtttt attggttcaa aaggggaggt    360 tatttttaa aggcttatgg aaaaaggtag ctatgtttgt t                        401

<210> SEQ ID NO 15
<211> LENGTH: 601
<212> TYPE: DNA
<213> ORGANISM: Homo sapiens

<400> SEQUENCE: 15
tttgttagaa agtggctgtg atcacaaatc aaaaaatact aactcatgta caagtgaagg     60
accactggcc actttggagg tctcttgatc actcttggat tcccatcaac cttaaatagg    120
ataccagtca gtcccctgct gcctatcctc aagaattctt tcactttgaa ggatgtataa    180
cacccataac aacttatgag gcaaacatgt tatacatgaa ggcaactttt ccaatatatc    240
acctcccccc atacaactta acacatctga actttcatgg gattcaaaat acaaaaaagt    300
ccggattctt tcatatgcac gcagatccaa taataacaaa taattaatga ttctgagtgt    360
tattttatga ggatggcatt ttatatccct catgcttagg gcaattctag aaggagatat    420
tatcaccatt tcactgttga aactgactca gaagcttatc caagagcaca aatcaacatt    480
aagtaacaga gctgggattt aaacgctgct gagaaatccg agaggctctg tatttttaa    540 aaacaacttt tagagtaacc ttttcttttc agccatgtta attataggaa gagactacaa    600
t                                                                    601

<210> SEQ ID NO 16
<211> LENGTH: 601
<212> TYPE: DNA
<213> ORGANISM: Homo sapiens

<400> SEQUENCE: 16
cgagagtctg gcttccagtg aagaacactt gacaagggag aaaatctgga catttctgcc     60
tttgagtttt gcttaggcca atcttgcaat tctccctcaa tccacgtggt caccatcttc    120
ccacctaaag agcactcacc tcctttgaga agcctgtgct tgtcctgacc cctctgagca    180
cactttaaag tttatgaatt cattccttcc tttgccattt ccagaaggtc tttgtatttt    240
gcacaaggac tctagttctt tgtgctggca tcaattagag actgtttgtt ttctgttttc    300
ccgggttaat ggtaaatgtt ttaagggtaa agatcttatc tttacatagc attgattttt    360
gaacatttga ttacttgctt atttattaag cctttgctca tttgccttac cataatcttt    420
tctataccct catgtttgaa ttgtttttat ggcttaagta tatacatata atatgtatac    480
```

```
ataattatat aaaatatgta tattctcttt tatacactat gaaaacaatt cttggaagca    540
cataaaatgt ctttgcacaa taaagaaata ttttaatatt gataattcat aaattatatt    600
g                                                                    601

<210> SEQ ID NO 17
<211> LENGTH: 601
<212> TYPE: DNA
<213> ORGANISM: Homo sapiens

<400> SEQUENCE: 17
tgctcacttt ttccttaatg gagattttgt tccatgtatg gtaggtaatg atctgaggca     60
ggaagacaaa gagcagatag cattcagggc ctcaaaagat tcccctaatg tgtacaaaca    120
tactagatct gaagttctgg ttcaccatgg ttcttcctca ttaagccgca gatttccact    180
tggaaaattc attggtaaag tgccatgcct gcttgctgct gataggattt tcttattgtc    240
cagcagtatg caagtattca gccctcagtc tctcagaaga ggggtctgaa ttcccttgtt    300
ccggggttgt gaccttaacc ttgtcctgag atttatagcc cagagaggc tctcctcctg     360 atttacatag ttcctgatgt cactttgagc agtttagttc caatctctgc agaacatctt    420
gactatggaa tgtgggaaca cgacgagctg tttgttttat actcccaaat ccttgaacaa    480
aagttacaga gtgttttct atcttctcag aggaagaagg cccctctccc attcccattc     540
agttctacca gcagcagct gttgctgtgt gtactgtgtt taaaatccct ttgttttatg     600
c                                                                    601

<210> SEQ ID NO 18
<211> LENGTH: 601
<212> TYPE: DNA
<213> ORGANISM: Homo sapiens

<400> SEQUENCE: 18
ttctctttct taatgataaa attaccatag taccaaagta acttagcttt agccttcttc     60
taaaataggc atattcaacc tcagcaactg ggccagacaa attttttgttg agggaaatgt   120 tctttgtgtt ttaggatatt tagaagcact tctggcctct ggccaatagc tgcctaacac    180
tcctctccct cttttctaga gttgcaataa aaaatatgt ctagatgttg tcaaatctttt    240 cttgggggc aaaagtgtca cctcttcaga actaccagtt agtagatatg gtaaaaagag    300
ccgggttgct ttttaatttt attgcatatt gacaaattat aattgtatat aattatggga    360
tacaaagtgc aggaggctga atgaaatagg aggatcacct gagtctggga gttcgaggct    420
gcagtgagct atgatcgcac agtgcactct agcctggatg acagagtgag accctgtctc    480
aaaaaaaaaa aaaaaagga taaaaagga atatgcgata attgcgtacc tgcgataata    540
tgatgcaggt acgcaatgtg gaatgattaa atcaagttaa ttaacatatc catcatccat    600
c                                                                    601

<210> SEQ ID NO 19
<211> LENGTH: 601
<212> TYPE: DNA
<213> ORGANISM: Homo sapiens

<400> SEQUENCE: 19
tgctcacatc ccaatgtctt agtgactta ggaaataaag cagctctgta attttttttc     60
ttacatcctc gctattcaac accatactca gtacataaat ccagtgggaa tccggacagt    120
aaaataaatc tgaatgacag ataatgtgct gtcctcaaaa atgactctcc tccttttcaa    180
```

```
ctgaaagaag acatttgttt atttcagtga aaacgagttc attattatct gttcctactt    240
ccttgggagt gattattctg tcagatacat gctaagtgca aattttctgc atagcagaaa    300
ccgggtcttg aatccaggtg ttctgattct gagtttattt ctctaaacat tggtaatgac    360
catagaaagt ctattttaaa aggaaacaca aaccaaagac taataaaact atatgcaact    420
agagagaatt gtatcatgat ttagatgagc tctgctttct acccttctca atttaagtgg    480
gggttcatgt tatcccttac tttcattgtc attttccttg gtccagtgtt ctcctaggtc    540
tccaaatgaa gctatcactt gcagtctgca aaacacaaca ctgcactaat ttaattctgt    600
t                                                                    601

<210> SEQ ID NO 20
<211> LENGTH: 601
<212> TYPE: DNA
<213> ORGANISM: Homo sapiens

<400> SEQUENCE: 20
aatgttcctt ttagattccc ttctttcctt ttccttcctt ccttcctttcc ttttcctccc     60 ctccctccct ccctccctcc cttctttcca tgttgttcag gtcacactct tcagctagat    120
ttgggggaga agtgggctca gaaatgttgg gcatgtgtgg cagcacctaa aacgttatgg    180
aagcagggtg agtccctgag catgaagcaa aggagacatg taaaggaagg aatatccagt    240
tagtatctga aggtggaaca aaatcattta gttagttcta gccacacaat ctggttttac    300
ccggattgaa tagttatatg actcaggaat cagaacccaa acgaattaat aggcaagaaa    360
aatggcatcc cagaatctgt gaaaactcat attgattgaa ttttaagaac aaaaaaggac    420
cttagacgtg tcaaaatcaa ctattccaag tccctctgtg gtattaatga catcctgtta    480
aaacaaaaac aaaaacaaaa actttcagca acatcacttc aaaattatcc tttttttattt    540 ttgcataatt ttaattcata gaatctttta tgaaaatatt tctaaaaact ttctgcactt    600
a                                                                    601

<210> SEQ ID NO 21
<211> LENGTH: 601
<212> TYPE: DNA
<213> ORGANISM: Homo sapiens

<400> SEQUENCE: 21
tgacctcata tggcagcaat ctgactggtg attgcactga gagacaatgc acatggcata     60
agaacagctc ctttacgctc ctcttgatga agaagaacag gtggaatact tcatatactt    120
tagatattga tgtcactata agcagctttg actttgagtt cagaaagcaa ttgatgggaa    180
tgcaggcttc tagaagtata gctgtcacac agatttaggg tctgaaagca gttttctggt    240 ttacctttg gcacacaaac cttctctggt aagggactga acttaattgg agtctaagat    300
ccggtagaga gagccatatt gatacttata tgaattctag agttttggtg aaaaaaaatc    360
aaaggtaagt aagtgcaaaa taaattgttt tgcaggcata atattcaaa catataaata    420 tatgtcaggt ataaatatac atattaatat gtgaatatat tatatataaaa tatagtcaga    480 tataaatatt taatcatcat agatttagac cgaaggagga caacataaag aacattactc    540
atttctttga gttgctgggt atagctcaat gatggtggat cttgggtacc agaaaaaaat    600
g                                                                    601

<210> SEQ ID NO 22
<211> LENGTH: 601
```

<212> TYPE: DNA
<213> ORGANISM: Homo sapiens

<400> SEQUENCE: 22

```
tttcactaaa cattatgtta agtaatgtat gtaggttgat aggtttatat ggtacagtaa      60
gtcattaatt ttaaaccttc atatgaattc aatcaaatct ttcatgctat ctccttagac     120
attagaatta ttttaaattt gtgttttgtt ctgttttgtt actacaaaca ttgctaggat     180
aaacatttcg tgcatacgtg cagacgtttc tacacagttt atttatggtg gccacaaagt     240
ctctatatcc taattagtga cctctgtgtt ctattattag cacaaatgta tattttcaaa     300
ccggatcttg tagacaactc cttgggagtc attaacaggg agggtacctg atagttttct     360
tcagatcatt attataagca gggatatcat gcatggagaa tttatagctg ctctataagt     420
ggaagggcat tgttccatta ttactaaata ttgccaaagt gatcttcaca taggttgctt     480
ctatgtatat cccaacaaga aatacacgga agttctcatt actccagatt cttgacaaga     540
atttatatta tcagactttt aattctttta ccaaatgaac ataatgatt atatatcttg      600
t                                                                    601
```

<210> SEQ ID NO 23
<211> LENGTH: 601
<212> TYPE: DNA
<213> ORGANISM: Homo sapiens

<400> SEQUENCE: 23

```
tttgccaaag aactatgact ttagaatatg tgttatttac tcttccaaga tacagctgaa      60
tggagggggg attgggttgt gcagatggca cttttttgcat gtcccttgct cagataattg     120
gattgtagaa ataaagaaa taatcaggat gtcaaatttt aacattcctt ttactcatgg      180
atactttggt gttgctctta tttccatagg cagagggcag atgattttca gccccataga     240
aatagcagaa tgtgcaggct actaacttcg cttccttgaa ctaacattat gatatcatca     300
ccggattcct cagcacaaca gcctgttctt aactcagttc cgaatgtttt ctctcactat     360
catctcgatc acttccaaat gttttctctc actatcttct tgatcaggcc atcccattct     420
taggttctta ctgtgccttc tcactttgtc ttaaacagat aaagtccttc agctgattac     480
atttcaaatg cgtcaccagg ttggccagaa cgcgtcggtt tcttcctatc ttgtttcttc     540
cacttttttta aataaaatag attttttctag gaggacacta tttaactttt cagcacatat   600
c                                                                    601
```

<210> SEQ ID NO 24
<211> LENGTH: 601
<212> TYPE: DNA
<213> ORGANISM: Homo sapiens

<400> SEQUENCE: 24

```
ttgctgacga ttcacatttt attagtttgg ttatgttttg tccttttaaa acattttctt      60
ttgagatggg ggtcttgctc tgttgcccac gcaggagtgc agtggcatgc tctcagctca     120
ctgcagccct gactgcctag gctccagcaa tcttcttacg tcagcctcca gagtagctgg     180
gaccgcaggc acttgccacc acgcccccact aaaaattttt taaattgttg cctttcttga    240
agtgttctct gcctgtcttt gtcacaaaat ttcattttc tcatagttaa tttcatctct     300
ccggtaagat tttattggtg tttcttttat aactttgcag ttcttacacc gtttggtgat    360
tttcatgttt cttagaaact ttaaaccttt aacttcaaac attaaaatac aagtctttta    420
agtacatgag tgcttagaaa tgtacataat gtttatatac acttatgcct tacattaaag    480
```

```
tccaatatga gaaatacatg tttaacattc aataataatt ttaaaaattt gagaaataaa      540
ctctcataaa tgcacacatt tttataaact tgctacttgt ctgctgttga ttttaacatt      600
t                                                                     601

<210> SEQ ID NO 25
<211> LENGTH: 601
<212> TYPE: DNA
<213> ORGANISM: Homo sapiens

<400> SEQUENCE: 25
gcagaagctt ttcctctcct gccctgacgg cgagttttct ccataacttg ctcccggggt       60
tcccctgcgg gtgtcctctc ccatccagac tggctggcca ttcccgggac tagacggtgc      120
ttagggcgat cgggagctct gatccggcct gattttctg atcatcagct tcctttcttt       180
ttcatactct gattctaaag ataaagatag agccagtttc tcccccttg gtgtttcaaa       240 ttcctttctc atgactcttc aggcagtaca gtgaagagat taagtgcacg acgtggaatt      300
ccggcctgtc tccttaatag ccttacgatc tacctcacgg aagtgttatg agggtggaat      360
gagttagtgc acataaagcc tgtagcatgg tgcttggccc agaataggcc ctcagcgaat      420
gttagttatt atggtgatga ttaatacttc agtttctctg tgctcagcaa acaccacctc      480
cctgtgtggg cactgcataa tcccctcgcc acatatattc aaggtcctac ccctgtctgc      540
ttatgctatg gtctctaagg aggagcaatg ggggatgcct gtcaccttcc aagacttta      600 t                                                                     601

<210> SEQ ID NO 26
<211> LENGTH: 601
<212> TYPE: DNA
<213> ORGANISM: Homo sapiens

<400> SEQUENCE: 26
ttgtgttatt agtagagacg gggtttcacc atgttggcca ggccggtctc gaactcctga       60
cctcaggtga tccacccatc ttggcctccc aaagtgctag gattacaggc atgagccacc      120
atgcccagcc acatagaaag atttttgatta gatattagga aggatttggg ctacaacaaa      180
aacttgttga acgattaagt caaagcatac tcctttgaat actgaaaatg tttgctgagg      240
ttgtctcagt tttgaaggac tgctttccat tccattttc ttgttatctt ctgatctaaa       300
ccggtgataa atttatgct gtccgatgac aggcaggaat ggtaacagaa cttgcagata       360
ataggttgct taccaaaagt tatagattga ccaaatgaat ttgttttcta agaaaatgga      420
gggcattaat ataaaactca aattccttgg agttactcaa agccctcaag tatatttgtc      480
cttgtccatt gccatggatg tttccaaaat gtaagctttg atgagaagtg gtaaagaaaa      540
taaggcattc aaacaacaga catgagactc ttgagtggca ggaaattttc catctcactt      600
g                                                                     601

<210> SEQ ID NO 27
<211> LENGTH: 601
<212> TYPE: DNA
<213> ORGANISM: Homo sapiens

<400> SEQUENCE: 27
ccttagtttt ttgctgtaac ccagctcatg gccaaggcat cgttgcatag atttgagaca       60
ctagaaatca aacctgaact gccggaagtg cagatgccca ggcagacctc ctggtcaggc      120
ttcaaatccc accttccaca cctgttcctg ggagatgaag tttgtaccca tggtcatctg      180
```

-continued

```
tccctctgcc actccattca gatgtgtcca cgtctccatg gccccctccat ccaagagaaa    240 gcaacacaca tgtgcaacca ggaaacatac aaaagtgcct tgcagccttg tggatcctta    300
ccggccagat agccatgggc tgtggaatgg aacataaata tcacacaatg cagttttcct    360
tggcagcaaa aatgagcaaa caataacat acataataaa atgaataatt tcacaggcac    420
aatgaagagt gaacaaaacc aggcacaaat gagaacaccc tgcgtgattc tatttataca    480
aagttcaaga atacgcaaaa tgaacctgtt gtaatggaag gcaaacagt gtgatctccc    540 aatgagatac catctcacac cagttagaat ggcaatcatt aaaaagtcag gaaacaacag    600
g                                                                   601

<210> SEQ ID NO 28
<211> LENGTH: 601
<212> TYPE: DNA
<213> ORGANISM: Homo sapiens

<400> SEQUENCE: 28
ttttgcctag tttttctgta acctgcatag ttgtttaaag ctatagattt ttaaaaaaat    60
gtgtgcattc aagtttgttt agagtacaaa ttagaaaaga agggtgcttt cctttcccag    120
ataaaacctt tgcggatgtc ttgggggttg atactgacct ctagtgaaac cagtctaggt    180
cagtgctgta gctggaaatt taaaatccca ctcaattgat tggaatcagt gctaagagta    240
aattaagcta ataacaactc tctttcaata cagggaaaag aaacagaaaa ttctggacat    300
ccggaaaaat gttaaagatg ctatcgtggt aaggactttt ttaaatgatt gtttactaga    360
aaggtcaagt gctcttcatt ctaaaactgt gtagacagaa attacatatt gtagattatc    420
atacatggag cctaaatgtt tatccatatt ttttttctta ttccatttta gacaattgtt    480
tcagcaatga gtactataat acctccagtt ccgctggcca accctgaaaa ccaatttcga    540
tcagactaca tcaagagcat agcccctatc actgactttg aatattccca ggtaagaaat    600
g                                                                   601

<210> SEQ ID NO 29
<211> LENGTH: 601
<212> TYPE: DNA
<213> ORGANISM: Homo sapiens

<400> SEQUENCE: 29
aaccataaaa ggggcagaga tagactctgt gggttgtctt tggaatatcc caagggattt    60
gctcctctct gatcatgtag gtctgcggct ccaagggcag tccgtcacca ccctatctgg    120
agcactcttc tatcctcctc ccatctctgt cctctggcga tgaccacagc cccgggcact    180
gctagttgtg cccttgcta agctcccata ttttgtgtta aggagcaagg attttcacag    240
gctcatagag catttgcttc ctttctaggg taattaagac tacactagaa accatcttgt    300
ccggttctct tttacagatg ttgacattag ggccccaaga agatacgtag cctgctggtg    360
tcacttaggg aattaattcc tgagcaggtc tctggtgcct ggggccctgc tcagacccca    420
ttctctcctc tggttctcga tggccctcac ctcccatttc tttccatttc ccagaggagt    480
ctggttgaac ttatggcttt ttttgccttg attaattgac tatgaattta tgtcccctaa    540
aaaaggatta agttgcatca tttcttctta gcatgcagtg ctcagagaca acccagcaat    600
t                                                                   601

<210> SEQ ID NO 30
<211> LENGTH: 601
```

<212> TYPE: DNA
<213> ORGANISM: Homo sapiens

<400> SEQUENCE: 30

```
gataaagaaa gtaattttat aagagaggaa ataaaatgta atgcttttc cagcataagg      60
tgaatgagat catctgggtt aggaagtttt tctatgctgg aagatatga taaagtaatt     120
gaacataagt gcctagaatt ttataggaaa cttccaaagt cacttgattt agaaggacag    180
atgaggctca atatggcttc ttccctcaga agtggcatag gttacagcag tagaaactta    240
atccagcctc agaaagagtt cccaaagcac tcaaagttg tatgcaaaag acttagaaaa     300
ccgggctgga aatattttat acagtaaccc tgaatgcttt aggatggtta cttttaatg     360
tattccatgc ttgtctaaca cctgcccatt ccagggggta catacgcagg ggcctctcca    420
ggcgagcatc tcagttatac ttccatcagg tcctggcagg aacactggat agggaggcta    480
gattcactgc acatcgcctc taccatagct gctcagacct tcatgtgcac acaaaacacc    540
cagagatctt gttggaacac aaattgccag ggtacaaccc aggggaattt gcatttctca    600
c                                                                    601
```

<210> SEQ ID NO 31
<211> LENGTH: 601
<212> TYPE: DNA
<213> ORGANISM: Homo sapiens

<400> SEQUENCE: 31

```
aaaaatttta aaagaaaag tatgatgatg ataaaatgaa ccactaaaac taagaacaat      60
aagtgaaaaa aaatcacttt tttctgagtg ggagaaacaa aggtatagag acggtcttgc    120
taaggaaaa ttgtaaattt aagtagcaat aaagaacgtg gcataatttt ctccagcagt     180
attcagtggc agaggaaaaa tatatgcatg caagtagttt ggttgattga atctgtggac    240
agaaaaaat aaaaaagaaa accaattgat gaattgtggg aaactatttc aagcaatggc     300
ccgggtcttc tggaggtatt agggaatatt acagcatgaa atgacatatc ttaataaaga    360
agtttagaga gaataagaaa acagtatagt cgaatattgt tatagtaact acaataatta    420
actacaacaa ttcatcatta tattcaaaga cagagaccaa aagatcatat tgaaaccaac    480
ccaatagtct catggacagt tgtttttgga taaacataga aattgcccct ttctggtctt    540
aaaacttgaa gccggccagg cgcggtggct cacgcctgta atcccagcac tttgggaggc    600
c                                                                    601
```

<210> SEQ ID NO 32
<211> LENGTH: 601
<212> TYPE: DNA
<213> ORGANISM: Homo sapiens

<400> SEQUENCE: 32

```
tggatttaaa aaatatatat atcacgagcc gaagtatgaa ccacgagaga ttatctccac     60
cccctgacta aaatctccat taattaaaca tgaatgcaaa agtagcctct gcctacaatt    120
catgtgtgcc ataagatga ataaataatc cttactgagt gctttgaatc tctgaaaaga     180
gagcgagcat acaattgtta gacatcttta cacctgccct catgttatct aataagccca    240
ttatggagtt taatacaaga aatatataac aaaattgtag aacgtagaaa tatataaaat    300
ccgggatgag ccagaattta cctttgtaact agaattactt catttataat ctataatgct    360
acagatgtat attctcaata gtatcaaata ggtttatttt ttccaacccct ggatttctt    420
cttgcatctt caccatctct aagcaaagtg attccatagc taaaaggcag aaatgtgaat    480
```

```
tcttcttcaa acttgttaat acatgttgaa caagatgctg ataaacccaa tctctaaaaa    540
tatgaaatat ctgatatttt gtaactataa aaatcttaa aaagggaaac aaatccaaac     600
t                                                                    601
```

<210> SEQ ID NO 33
<211> LENGTH: 601
<212> TYPE: DNA
<213> ORGANISM: Homo sapiens

<400> SEQUENCE: 33

```
actagaaagg aaagaaactg cccttccttt aaggaatgtg gaatctttcc ttttgaagat    60
caagatttgg agcccataat cctgtggatg gatgacgcca acattcagct ctgctgctta   120
ttccccataa tttctccgct tgacctgtga cgaatcagct tctgcctttc cagggactta   180
gaacctttct tatgggactc ctctcactct gaatgatggt gattaattac cagtgtactt   240
taaaagtctc ctctatttaa ttacatcctc ctgagtattt ggactaattc ctcttagttt   300
ccggtgcaga tcggaatgtt gccttgagca agtctcatgt ttctttctcc cgcttacgca   360
gtcaagcaca tacatagata cgtaataaat attgattaag gttctgtatt aggctgtgtt   420
tttatcagta aggattaata ggcataaatg agagacatga tccctaccct ggagcctaaa   480
tggcatgtgt tataaagacg ctttcaggct gaccagttct tctagtgcag ctgagaagac   540
agccatgcct cctcattagc ccactttata gggaagaaat ggagactcaa agtatctaaa   600
t                                                                    601
```

<210> SEQ ID NO 34
<211> LENGTH: 601
<212> TYPE: DNA
<213> ORGANISM: Homo sapiens

<400> SEQUENCE: 34

```
ttttagcatc atctggtgag gctaaggatt ttcagaatca tcagatactg gttctttttt    60
gttcgatgtt cttccctcaa tttatctctt tcctctcccg cttcactata ataacatga   120
agaaaccagg tgatacactt aacactttgt ttggaaatag ccttagctat gtgaccaaca   180
tcatcgctta caagtcctgc tctccatgga caatttcatt aaactctctg gcacacatgg   240
gaaggatcct ccttgctccg atttcctgga acacctgtca cattcctttc tgagttctcc   300
ccggaggatt cacctttagc atccctattt cctctagcag tctgttcatg gtgatttggg   360
cttttctctgc tgtgctactc aaaagtctct tagcctctac tcgctgccaa gtcccaaagt   420
tgtttccaca ttttaagttc agaaggtttc caacttacaa tggtttggct taggatttca   480
taatgttacg aaagtgatat gggttcaata gaaactgtac ttcaagtgcc catacaatca   540
ttctgtgcta cattttcagt acaacattca acgaattaca tgagatactc aacacttgat   600
t                                                                    601
```

<210> SEQ ID NO 35
<211> LENGTH: 601
<212> TYPE: DNA
<213> ORGANISM: Homo sapiens

<400> SEQUENCE: 35

```
aataaaatag aaggaacttt gatatatgaa tcaatatgga taatccttac tcttatcgaa    60
atccttactc tgagtcaaaa aatccaggca agaatgcata cacagtatat cccatttata   120
taagtttttt aaaatgcaaa atacttggat gaaaggtggt cagtaactaa gttgttgcct   180
```

-continued

```
gaagatgggc atagagggag ccttggatta agcaagacag taggacactt tgggtggtaa      240
tgaaaatgtc ggttttcttg attataatga tggcttcaag cacagataca gatattaaaa      300
ccggtaaatt tttcaaatat gtgcagttta ttttaattaa attattcatc aatagagttt      360
aagacacaaa caactggatt ccaccagaaa actaaatata ttaccttgtt aaattgatgc      420
ctaagtgaag catagtgcct catagcagaa agggttaaat ttatttcatt aatcctctgt      480
tttgaaaaag tgatcactag ataagtttgt tcaaaagag acaaaataa taacaaaaac         540 aactaggctt tgactgaaaa tccagtgcct taaaaactgt agagaatttc tacactgttt      600
c                                                                      601

<210> SEQ ID NO 36
<211> LENGTH: 601
<212> TYPE: DNA
<213> ORGANISM: Homo sapiens

<400> SEQUENCE: 36
acaccagcat ggcacatgca tacatatata actaacctac acattgtgca catgtaccct       60
aaaacttaaa gtaataataa taaaaaaaa gaatgcttg cttacaaatt gtgtttcttt        120
agcacttaat gttgttttgt gtttttcaaa aaacagcat ccaaatatac tggttgacaa       180
tttgtttcca gttttttct ataatgaca aataggat ttaattttg tctagcgtag            240 agaagaaaca ttataatttt gacaaaaata tggtttcacc tttcatataa aattctaaac      300
ccggtagcac acttacctga aaggtgagaa atatgacatt gccccagtaa gtgacaacat      360
ctgtggtgct atcacaaggc taaattcctt tattgtgtct tttataagat actgttaagt     420
ctagcaaaat accattttga gatgctactt aaacgtggct cagaataaat aaaaaattgt      480
caaagaaacg ttttaaatta acacttctga ttttaaaata taaagcaatc aaagacagtg      540
gttttccaac gtgaacacac cgggtatcag aggagtatta ttgaggcaat gtaaagagta      600
t                                                                      601

<210> SEQ ID NO 37
<211> LENGTH: 601
<212> TYPE: DNA
<213> ORGANISM: Homo sapiens

<400> SEQUENCE: 37
aggcaagtag gcgttggatg gcaatcctct cccatgtaac cgtgctaccc catggtatgt       60
caataatgaa aacaagttat ataacagatt aagattgtct aaaatgtatt aacaagaagc      120
aaaaatagtc acatcaactg ctcttgtaag cttagaatac taaggctgtt cagacattct      180
gaaagcagga taagccaacc ttctagtttg ggtcaagcaa cattgtcatc tctgaaatga      240
aagtgtgtgg ccaaatggag atgtgaacct accatgctgc tccagagata ttagtttctg      300
ccggatttgc atatctttac atcgagttca tacatgggtg ttggtgcctg tacactcatt      360
ctatccagtc atgtaactca agcacagctc attttactaa tgtttgtatg ctaattaaaa      420
actcttaggt atagattcct ataataatat ttaaagttat tatgtagcta cttctgaagt      480
gtgaatacct gagtagggta cttcagatgt tcaatactcc cttagaacag tgaatatagt      540
aagcactcaa atgttactta ctactttct tgtacttatc ttggttgtca tcttcattag       600
t                                                                      601

<210> SEQ ID NO 38
<211> LENGTH: 601
```

```
<212> TYPE: DNA
<213> ORGANISM: Homo sapiens

<400> SEQUENCE: 38
gcctcatcaa agcattgtaa gaactgataa ccatcttcta gaagtatcat agtgatatta      60
agaacacaca tcacagatca tagtaaatgg ctttaatttt ttagcgaaat ctcactactg     120
caaatgcatt gttgtcctag ctaatgaatg catagagtat tgcctgcaaa ataataattg     180
agattctatt tttaagaagc ttagaacagt acatggtgca tagcaaagac tctgtgtatg     240
tgaagccaga ttttaaaata tggtaacaag tgtctgaaaa tatgtggctc aatttgtctc     300
ccggttactt ttccctctcc cccttttaaaa tgtagaggaa ggagaagaag agataagagg     360
tttgtgagtg aagacaaggg cccttttaagg cctgggaaga ctaacgccat agggatctcc     420
ctctgcctta aaaggcacag gaatcttagt ggggaaaaag aagtggtgat aaatagccag     480
tccgtgtgcc tggaatatca aagtcagtgc gtgccaggga tcacactgcg ggtcacgtgc     540
actctgggtc tctctctgca aacctgccct gcctcagtct gggaatatgc aactgcctaa     600
g                                                                    601

<210> SEQ ID NO 39
<211> LENGTH: 601
<212> TYPE: DNA
<213> ORGANISM: Homo sapiens

<400> SEQUENCE: 39
acccacctgg tcgcatcctg cgttcaccag ttcctgcagc atttgccggt tcacttctgc      60
agctgcagag gtgcccgatt cattagcaaa aggcaacaag gaatatctga tttcccctcaa    120 ggctttctga taaggtccga actttggggt ggctctcatc tgctgctgct gcctggtggc     180
atctttgctc cccaggactt tggcatccag ggaagtgtca ctgtttggtc ctgcgggtag     240
cccctgaacc gaagacttgg atggctgttt taaccccctca cgaatctctt gcagtcgctg    300
ccggctattt ccagaataag tcgtggcagg aaaagtcttt ggcctcattg ttagtccagt     360 ttcctttttac cataaataca atcttcttaa agtgttttat tatttaaaaa aaaaaactgt    420
caatagtatc agtttgttgt aaacatactt tcaaaataat ttccttttga aaatgttctt     480
tccttccatt tttgtagttc ctatagagaa cctaaaattt tccaaagtct tcattttgaa    540
gattatcact ctctgaaaaa gaaataaat gggagagaaa tgttcatttg tcattttcac     600
g                                                                    601

<210> SEQ ID NO 40
<211> LENGTH: 601
<212> TYPE: DNA
<213> ORGANISM: Homo sapiens

<400> SEQUENCE: 40
gggtgcccgt agtcgccgct gaccttctcg tagtgagggc agaagacgct gtccgcagtc      60
cttagcggga tgataatgtc actgggctct gagccgttgt tgttgccgct gcgcttgggt    120
gtggccagtg tgctgagcga cagcgtggtc gtgtgctgcg gcgagtgctt cctgtgtctc     180
ctccggtact tcagcaagag gaccaccagc gtgatgatga tgacgatgaa gatgatgcat    240
cctgaagcaa tccctgcaaa taaggccact tcggaaccga ggatgttgtt ccccgaatgt    300
ccggcgctgt tgccgtctgt gctagaacct gcagacgcgg agacagaaaa ggtcagagat    360
agttactgct gtcccagtgc agacggactg ctttttatgac ccttaaaaat gtgaaaaata   420
agccaggctt attactaact agaagctgga ctttgcctcg ccaataccctc gtctaagagc    480
```

```
tcaacgcaaa aggaaatgag aggtatctct aggagggact tccctaccct cccaagccac    540
agggtttcct ttgtatcatt atccagcaag agcacagact gtcggtgaca gccagccctt    600
g                                                                    601
```

<210> SEQ ID NO 41
<211> LENGTH: 601
<212> TYPE: DNA
<213> ORGANISM: Homo sapiens

<400> SEQUENCE: 41

```
tttttttacgt aatgctcaaa tagacctggg agataagcac tgctatgaat ccccaatccc    60
catgttacag acaaagaaat tagggccaac gagtggtaca actggattaa aacctaggct   120
tctggcccca gagccgcaca ctaaactgct gtgcttgagc gctataaaat aaccacattt   180
atttatgtat tttctctagt gatacttatt tgcaattttc catatcatga acaaatttca   240
gtgaacttcc ttatgcctac ctcttgtgtg tatgtggaca tttcctgggg atatatacct   300
ccggtggcat acctgtgaaa tcctttgctt attttttgag agaacagagc agagcagatg   360
ctaaaattgc cttttttcct tgagaatttt ttttctctga tagaatacat gttccatgaa   420
ggcagggatt tttgtctcct ttgtccactg ctccattctg agcatctaga agaatgccag   480
gcacatggga gatgctcagt aaatatctgt gaatgtatta atggctcctg aatacgacgc   540
tcttttagcc taattatgcg aactcttttt ttttgttcc ccgccccacc cccctccaga   600
c                                                                    601
```

<210> SEQ ID NO 42
<211> LENGTH: 601
<212> TYPE: DNA
<213> ORGANISM: Homo sapiens

<400> SEQUENCE: 42

```
atataaatct tctttaataa aacaattctg tgggacagat ctgctaccaa ggctcagaga    60
agttgagtgg cctgaccaca gtcacacagc tgataggtag caggattggg actagagcct   120
ggggctcctg cgccccaggt cagttactag gcatgaatag aaacaccgca ctgcaacact   180
gaatgttagc cgacatggca gctaaaatgc acacattagc attaccaaat gagtgagccg   240
attgagcaag tgagttctcc taccactacc tccccttagc attggctttg aagacggtaa   300
ccgggaaaac tcagactggg tcgccccatg ttattgcgcc aggactggag actctgagaa   360
gctggttgca acatttggcg tcttcgcttc ggatgctcta taagccttt  gagagatgag    420 cctgagtttg tggcggcagg ctccctttg aaagagccac ccaatctggc ctccccagac   480
atcttcctgg aggaggattg agcattattc caaaaagaa gggtggcctc gagctggccc   540
atcaggccct agcaataccc agctcctcat caggatgggt gcaatgtttg ttttggactt   600
t                                                                    601
```

<210> SEQ ID NO 43
<211> LENGTH: 601
<212> TYPE: DNA
<213> ORGANISM: Homo sapiens

<400> SEQUENCE: 43

```
atatattgcc acctgaagag ttggctttca gagctctttg gaatttggaa ttgtagatgg    60
agggtcatgg atgtgtacca aaaatgttct taacagccaa gaagtccaca gactaggcat   120
tgtgcaacag tcaaaagcaa ctctagacag ctccccagac cagcacagtg ctgcttgttc   180
```

```
atccttgctc ctaggaagca ggaagtacgt gatatcagct ctcttggaaa taactgtccc    240
tttaaggagt aattgtcttg agtaacccct aaggaagtat taagtattaa aattctaggg    300
ccggattcac catcccctaa ggattctgca tttctctctg aaaatcttaa gttcagaata    360
accaaccagt tccttctaaa catcaacaac cttatgttaa gttctctgac ccttccctgg    420
taattcgtaa gttatataaaa tctctcccct taacttaagc cttagtttcc cagatgccat   480
cactttgaaa atctgcctca gaaacatcag tacctcctaa tgggatgtga tagaacaccc    540
gaaaaactgc tgaatggtgt ggtgcttccc cagagcccag gggacagtgt ctggggtccc    600
a                                                                    601

<210> SEQ ID NO 44
<211> LENGTH: 601
<212> TYPE: DNA
<213> ORGANISM: Homo sapiens

<400> SEQUENCE: 44
gcagatggta tgccagggac aatatacaag acagaataga gttcattcaa gtattctatg     60
ttttgttatt tagttttcaa atatgaaccc tggatggaac caggctttgt tcccccaagt    120
tatcagctaa agagaaagag ctcagccaag tgacaaggtg ttgccgcagt gataactcaa    180
ttttgtggtt ttcagaaatg cagaagaaag aaggttggaa agaatgggct ggcactcccc    240
gaagagtggg gctcaaagtt ctggtctcag cagatctttg agggagacgt agggtctagg    300
ccggcaaaac cagagagaag gataggcttt tagatgctca tcccacccaa aaccatgaaa    360
taatctcccc tgtctcctga ttagtatttg tcagcctcat ttaccettaa gatttgtgca    420 aatgaaaaac gttaaatgca gttcctggat cagtaattaa acataattat ttcagtggaa    480
gagattttgt ttttcataat ctcctctttg tctgcataga gccagctctt ggttacatct    540
gccactgata gcctttgctc tgtttacttt aaagaataag ccactgtttg atttggtttc    600
t                                                                    601

<210> SEQ ID NO 45
<211> LENGTH: 601
<212> TYPE: DNA
<213> ORGANISM: Homo sapiens

<400> SEQUENCE: 45
tattcgcatg tgttttttgtg aatcattctg tcgaacaaga tagaaaaaga agggccagtt    60
cctaggttgc actgcgtgtc tgtgtgatgg aatgacccct gtaactcctt aggccttgat    120
gcttcctgtg ttgtgtggga tacacagaat ccacttgcct tcctcccagg gctgcagaga   180
tgaaaaacta tgacacacat tacaatgctc tgtaaactat gttattcta caaatgtgca    240 ttatgttatg aaagtggagt aactaataac tccacacttc tgccctcaga aaacttccaa    300
ccggatcatc tacctctttt tgaacgtgcc cagcaatgga aggttcctgc acggcctcat    360
gtgttgttgc ataaccctca acattaggaa agggttattt ttatccactc aaactttcat    420
atgttccagt ttaagtaatt tacccttccg ctgtgctcag aggggacagg gactgaggac    480
acgtggccag atctaattgc ttcctcccctt ccaggatgaa ggatcaaaat tctttaacct    540
ttctcaattt ccagtgtttt aggcctattt ttacttgata tattccttct tcaagggaca    600
g                                                                    601

<210> SEQ ID NO 46
<211> LENGTH: 601
```

```
<212> TYPE: DNA
<213> ORGANISM: Homo sapiens

<400> SEQUENCE: 46
aagaagctgg aagctgattt agtaacttta ttgtagtttg cttggaaggt aaatgtatta      60
ttgtatcctt ctgttcactt aaactgctga cctagagtag gtttgaataa cactttgttt     120
agtttggcca caaaatgcct gtgaaagggg aaattctttg ggcagccagg gcaatatcac     180
ttccttatct cccagtaccc aaacaccttt agtttctcct tccttccttc cagttgcttt     240
caaaaagtgg cgatgaactg cttgtatagt tgccatttag tatccaaggg ggattgattc     300
ccggacgccc acagatagca aaattcctgg gtgctcaagt ccctgatata gaatgacata     360
gtatttgcat agatcttata cacatcctcc tgtatacttt aaattatctc tagattactt     420
ataataccta atgcagtata agtgctttgt gaatagttgt tataatgtat ttttaatttg     480
tattacttct catttgttgt attgtcattt ttttcccctg aatatttcct acccatggtt     540
ggtcgaatcc ttgaatacag aacccaggga tacagaaggc tgactatgtg acatttcttc     600
c                                                                    601

<210> SEQ ID NO 47
<211> LENGTH: 601
<212> TYPE: DNA
<213> ORGANISM: Homo sapiens

<400> SEQUENCE: 47
agagcttacc agtgttattt tccttattac ttctgagtct ggcatgctag tttggttagt      60
gatatattat tatttaggcc aaagtcagat attttataac tacagaagcc agttagttac     120
cttcccttg tttcacaacc gaatactata ctatgcacct atggtcccat ctaaaagata     180
ttactggtca taagaatgtg gctgtctccg aaaaaattgt cactactaga aaacaactg     240
aaagaacata gtgtaattag aacaatatgg ccaaacacgt ttcgttaata ctgtgtgttt     300
ccggaggaaa gggaaattag caaatatttt cctccttttc aacatggcta tgttcctaag     360
caagatagcc ttatcctgct gaggagacag aggatgtggc ataagacata cagaaattga     420
caaacatatt aaccttgtat aactaggact tttttacaag gtatatttcc cttgtaaaac     480
taggacttta attttgagaa taggatggga cagagtcaag tgaaagaagc cttaggtatc     540
acatggcacc aaggaaaaac atcaaagatt tctgtctgct gccttttcca catagtcctt     600
t                                                                    601

<210> SEQ ID NO 48
<211> LENGTH: 601
<212> TYPE: DNA
<213> ORGANISM: Homo sapiens

<400> SEQUENCE: 48
cagtaaagag accagccaca gataagtaat tggcaaccag caaggtaata atctagtgt      60
gggggactgg ctgacgtttg gtcaatgtct ccttccgaag ctccacccaa atttctcctt     120
tttgcttctc agtcacagta tttccctcct gttaaatagc attagtctgg ggaataaatg     180
ctcttccctg tctactacac tgtgggaaac gtcagccaca gcctccagtt tgttaggtca     240
aaaaccttga agtcatcctc tcttcctgtc gtagccacgt tgatccattc accagaaaat     300
ccggctgggc ctacccaaat atgtagagag cccagcacgt ttttacctct tccgtcgcca     360
ttgccttgga ccaatgcctc tcacctggac tataggaagg tcctccagat ggcagccctg     420
actcttttcct gccccctctcc agccgcactc agcctcacag tatcgatgat gatttttcttc     480
```

| | |
|---|---|
| acagtcaagg aacagagctc ctgggctgga acctcacacc caggaatcag ggtctgagct | 540 |
| gaggtcctga cagtcaccta caggattctg agccttaccc cattgcacta acctttcgaa | 600 |
| a | 601 |

<210> SEQ ID NO 49
<211> LENGTH: 601
<212> TYPE: DNA
<213> ORGANISM: Homo sapiens

<400> SEQUENCE: 49

| | |
|---|---|
| tgtatagatg cagagttttta ctactgaaag gaggaatact actgttgatt tgttttttgtt | 60 |
| tctcggttgt tgtgcgtgtg ttttgttgtt gttgttgttg ttttaccatc ttggtcctaa | 120 |
| gtagctcgtt tgccggccca gccttaatgg ccagttggct ccaagtcaga agacatgatc | 180 |
| tcctccccca ttctccatgc cattgtttaa agccctcct gaggaatggg ctgccttggt | 240 |
| gttttgtcag ttcaaaccac atcctgcctg tttccacttt ccataagaca actcgcaaca | 300 |
| ccggtggttt tcagatgtgg ccggcttctt ggtgaagcga tagcagaggc cttgttcaca | 360 |
| gaagtgaaaa taattcaccc agtggttagc acatcaggtg tgggcattga gtgtaccccg | 420 |
| ctccctgctt gatcccaatc cctggttggg tttgggagtg gacggctgcc caacctcctg | 480 |
| gcactgtctt gacccacagc cttctctggg atgaggacta agccagaagc agtaaggaca | 540 |
| gaggtgtctc aggctgtcca ggcctggcct gaatcccatg acagcaaggg tgtggcctgc | 600 |
| a | 601 |

<210> SEQ ID NO 50
<211> LENGTH: 601
<212> TYPE: DNA
<213> ORGANISM: Homo sapiens

<400> SEQUENCE: 50

| | |
|---|---|
| gctgagggat ttggtcatat cattagccca gacatagcct gacaagacca gcccttgtgt | 60 |
| aatgagattg gtttgaggta ggaactgtac ttgcttctcta tgatgggcaa gaggagaccc | 120 |
| caggctctgg atgggaagct gaaggctgac caagggtgga tgaggcagag ggcctgcgaa | 180 |
| ggggactcca cagaggccac acgcaggaca agagcagcac tctactccag gcttcatcca | 240 |
| tcgtatggag gtctgtggtc atttcaccca ttcatcttgc tcctctggag aacccaaacc | 300 |
| ccggaaacca caaagggaat cgactgctgc ttcacaggaa gggtttcatt catgatcaca | 360 |
| tttctttact gaaaagatg ggtatattga agcgttgact gcctcctcaa gaagaaacag | 420 |
| gaagtgatca ttaccaaaca gaggctccct ttaaatttaa aatatgtagc caagaaagag | 480 |
| gctaacacta cctaagaaag accccaatta aatgtttaag ctaaaaaaag cagagggttg | 540 |
| gggatagggc atgttttttgt tttgtcttcc aatttcagtg ttttttaaagg ctgagcacca | 600 |
| a | 601 |

<210> SEQ ID NO 51
<211> LENGTH: 601
<212> TYPE: DNA
<213> ORGANISM: Homo sapiens

<400> SEQUENCE: 51

| | |
|---|---|
| gatttttgca gagttatttt taagcagtac aaagtagaaa cacacttctt gaaacaaaaa | 60 |
| tgctttgtca tttcttaatc tctacccttta aaaatagcaa gcagctatttt cactctgagg | 120 |
| agcgcttaca cagccatcac tgcccgcaac cctgggacct gaggggggaga tgggtgagtc | 180 |

```
tggagaaaag gctgtttcct aagagtctcg ttgctagtcc tgctcggtca catgacctca    240
cctgtggtcc cgagcgatag tgggcagcac gcagttttat tacatgaggc agtatgtctc    300
ccggttcacg cttattatag caataattcc agagcttctc actcttggtt aaaacagaac    360
agaaacacaa atgcaatacc aagcacaaaa ccacgaacat ctttgagtaa ctgggctctt    420
cctcctacac aaaacgtcct gacgggtccc tcagagtgaa tctatggtca cgacccggac    480
cccggaggcc tgtgcattga gtatgcgcta aggttttaa tacaactggc ttctttccat     540
tgtctcccaa atatcccacc ccaggtagtt gggtactgaa cacaaactgg tcattttgat    600
a                                                                    601

<210> SEQ ID NO 52
<211> LENGTH: 601
<212> TYPE: DNA
<213> ORGANISM: Homo sapiens

<400> SEQUENCE: 52
catggtgaga ccccatctct actaaaaata caaaaaatta gccaggcatg gtggcgggca     60
cctgtagtcc cagctacttg ggaggctgag gcaggagaat ggcgtgaacc cgggaggtgg    120
agcttgcagt gagccaagat cacgccactg cactccagcc tgggcaacgg agtgagactc    180
tgtctcaaaa aaaaaaaaaa ggggaagtca ccaagaaagg gatagaggtc agtgacatgg    240
tcatcacaca actcggtcat ttaatatggc aaaacacaat accaagaact gtgcattagc    300
ccggaaggca agagggttgg ttctgcccca gctctgctgc taatgagccc ctaccaggtt    360
gagcaagtct ttccccactc tccacctcca tttcttaatc agtttcatga cagggaagga    420
tttgaaagtc ctttccacct cagaagtgtt gattattctc tctctcctat aatctgatga    480
aatcagcatg acaacaagta atttaagtaa aggacagaag ggttacccaa gaagaggcag    540
gaaaatgtta acgttctata aagttttatt cttgagtcat aggaaaatgc tctccagacg    600
t                                                                    601

<210> SEQ ID NO 53
<211> LENGTH: 601
<212> TYPE: DNA
<213> ORGANISM: Homo sapiens

<400> SEQUENCE: 53
cttgtgttac agatggaaga taagattgga gaggaggaag agttagtttt gagtctctga     60
caacagggct gccactgcca gattgcatca aaccgtttta ggttttgtct tctgggaagc    120
accattgcat catagtcaaa cacgagggcc aggaagccca agaagtgtgg gtttcaattc    180
catctccact tatcagccac acttttgtgc ctcagttttc ttatacacaa gataaggctg    240
gtaatctggc caaactttca ggataagaat tatagacatt taagaaaccc aggaaactgt    300
ccggcacata ggaagcattg atattactga gtgatagcac tgagccagta aaacctagac    360
agaagttgga agatagggca cagtgttctt gtatcttctg agcagatggg taaagaaatt    420
ggataagaat tcaacgtggt ggctgttgaa agtcatcact gggtcttctt ggtccagcca    480
ttccctttgg tctctgtctt tggcctggac caccatctta cctccatcat tcttgaagga    540
cacacctgaa gcctcaccat tgcagcaggc ttatcatcag gaattaataa ggtgcaggga    600
a                                                                    601

<210> SEQ ID NO 54
<211> LENGTH: 601
```

<212> TYPE: DNA
<213> ORGANISM: Homo sapiens

<400> SEQUENCE: 54

```
aaaaaactgc tataattcaa ccagttctga cacaaatggt gggtttcaga gaacggagta    60
gagatgagag aagtggcttt tagcaagaaa ttacgcaggt gactttcaaa taaatcatct   120
acatagaagg cacgttttgc ctctaatgtg caaataattt agcatctgaa atggcatgta   180
aagatctcat tttagattca attccactct aattcatcaa aatgggaagt aaggcattgt   240
ggcataacaa ttgggatcag aagacctgtg gttacatctc agttcagccc acagaactaa   300
ccgggactga ggccattggt cttagacctc tcatctgtgg gatggggtta ctaagactga   360
tttcctatgt ttctttgcaa aacttgaaat aattgtgtga agagtacttt gcaaagagat   420
aagtgctaca gaactataaa gtactaaata aaagctaata tattaggcat ctaataggta   480
ttaatagcag caaggtctga ccacaagcaa acacctattt taggcactga cttctgccaa   540
aaatccggag ctagatggag aaggaaagg ctcataaatc agtctcctta agaggcctcc    600
t                                                                   601
```

<210> SEQ ID NO 55
<211> LENGTH: 601
<212> TYPE: DNA
<213> ORGANISM: Homo sapiens

<400> SEQUENCE: 55

```
cagctggggc aggaaaacaa cggtgctgcc tatttcttgg accccaactg tttctaattt    60
gagtcactct tcagcactcc gttaaacccc agtccccatc ctcagttccc aggtgggttt   120
gcataagggg tagtagacct gccaggagat gcagtgagaa gcactgagca ctgaggcagg   180
aggagcacag acagcacaga gaatcctcta aagtgaagtt tctctctttc tcactgttgt   240
tggggactca ccctgcacca caaagaagac tagataaaga aaccactaa ccagtaacat    300
ccggctcagt aggctgagca caaaagcaag gttttgctttt ggccctagac ctagaagcct   360
gctgagtgag cgccttggcc ctagaaaaga ggagcagggg gttgtccgga gcccctccga   420
ccacgctgct ctcagtcagg caccacagac acaggcagag ctggctagag gtcagaggca   480
tggccccagt gagaagcagc agctgtgccc tgtgagcagg taggatgggg ttaagggctg   540
gcctggaatg ggggcagaag gtggaagttg ggaaatggtg atgacagcag ttattgcaag   600
g                                                                   601
```

<210> SEQ ID NO 56
<211> LENGTH: 601
<212> TYPE: DNA
<213> ORGANISM: Homo sapiens

<400> SEQUENCE: 56

```
tggcttattt ttaactcact taatatttt ctcttgagaa atgttaagct aattttttttt     60
tttttaaagg gaagcaaaaa ggcctgtact actgtcaagg cagactgaac ttattttatt   120
gactgtgttt tcgttatgg aggactgtgt gtgacagtac ttcttttact tacaaagaat    180
tctttgtcac aaaagcctca ttcatccact gacattttgg ggttccttt tctgtaaaca    240
atcaatctaa aaaggaagtg cctaatcggg tgtttatgtt acaggtgtag cctggctggg   300
ccgggggtag ttggcttcct tctgtttttc ctatgctctc gggaacattt gacctttagt   360
tcctttctaa atgcctcagt tcattagaaa tgttttgtgc tcattcaata agtcatttat   420
ttgaggtcag atttatattt tgaaaaggtc atttttggcaa gttatttggt cttcccaaag   480
```

| | |
|---|---|
| tccagagtgt ccagtataaa atagggatat cattcctatc tgtttcctat aattgttgtg | 540 |
| aggatgaatg tgttaatgta agtgaaaatg cttggtaaac aagaaggaga tatatgtatt | 600 |
| a | 601 |

<210> SEQ ID NO 57
<211> LENGTH: 601
<212> TYPE: DNA
<213> ORGANISM: Homo sapiens

<400> SEQUENCE: 57

| | |
|---|---|
| gatgtaaaaa tgggatcctt gattttagt atctgttttg ccgtccagct gtgcttgctt | 60 |
| tttaggccct aaaaactgta tgttttcttg gccctgttac ttaaaaggct ctaccctgaa | 120 |
| gccagtaatc caattaactt acttctttaa ggaaatgttt atatgtaagg gtgtctgctt | 180 |
| ttcctctcca tctcacctga actttcactc acgccatttt tcctttgttt gcataaaata | 240 |
| taaattctat atcttgtttc acttaagttt gtctcttcag aaatgcagat ttagagttgc | 300 |
| ccggctagga actgtttatg gcaggaagca ggtattcaag agactgttgg tctaaaatgg | 360 |
| ggaagagaag cttaaaacta gcaattgaaa aatcttttgt ctgtctgtgt aggttgtgtg | 420 |
| tgtgatgttt ccctactgaa atatataaag gtgctctaat taattggctt taaaaaaata | 480 |
| agcacttaca taaatatttt tgtcagaaaa atagaaacta aaatgccttt tagctcaagt | 540 |
| gactttaata atctttagta aataaaaata gttttacaat tattgacaaa agtctttaaa | 600 |
| a | 601 |

<210> SEQ ID NO 58
<211> LENGTH: 601
<212> TYPE: DNA
<213> ORGANISM: Homo sapiens

<400> SEQUENCE: 58

| | |
|---|---|
| gacatagtga taggttagac tgtctattgt gagattcaca aaggggtttg gaacagaaat | 60 |
| ctagaccaag acctttttaca caagagattc tttgtggaat acttgctgga atattcccag | 120 |
| agtattttgg gatacccccag actcatacaa ggttgtataa cctctaacta acaagattct | 180 |
| aagcaaagga tgagacgtga tcatgctcag gtaacgaaaa cttagggtca attcatgttc | 240 |
| taattagttc tcttgatcta acagttacgg cttataaatc attccatgtc ggaagcccca | 300 |
| ccggaaatag ttgaggttca attcagttac agctcaatga agtctgaaaa caagtgtcca | 360 |
| acattttctg gttcatggtt taaaataggt ttcaaataaa caatgaggaa gccagtttcc | 420 |
| tgtttgggtt gggtccattg gatcctagcc catcaaagct ttgaattata ttacaatgac | 480 |
| aggcaaggac tagaggggga agaactgaaa cgcagagaaa agttggcaca gtgccaggaa | 540 |
| acctggctaa aattaagtcc ctcagtccaa agaaaacaat ggcagctagg acatgagtca | 600 |
| a | 601 |

<210> SEQ ID NO 59
<211> LENGTH: 601
<212> TYPE: DNA
<213> ORGANISM: Homo sapiens

<400> SEQUENCE: 59

| | |
|---|---|
| agacacactt aagctgagct tagagcaaag catgtccctc aaggtgacct tgccgcatgg | 60 |
| cctgaaccta gaattcccct gaccagggtg gacagccatc accatgggcc tttctgcctg | 120 |
| gcctagtatg gctctccttc gaactcacct agacccttgc atcaaaggac tcggggactc | 180 |

```
tgctgcagtc atcctagcac ggtcgagagg agtaggaagg tgcccagcgg ctcagccttt    240
aaggaggtct attggtcacc attgcttctg ccttcttgag aaccatcacc ctcggaggat    300
ccggtagtgt atcccagtca agtgtcaaat gcgttgttcc ctggagagga aggcttattt    360
ccagaaagta ctctgacgtt ttgtaatttg tgatttctat cactggctca gtggcctacc    420
cactgctcag ctcatgtggc atgaccaggc tggggcgtcg ggtcatcttg ttctctgggt    480
gtgtggcaac actggtttat ggcgtaattt ccttcctgag aagaaattca gtaatttcta    540
atattcaggg ctttaggtag aggcctgaaa atcactctcc atgcctcttt cagtatttta    600
t                                                                    601

<210> SEQ ID NO 60
<211> LENGTH: 601
<212> TYPE: DNA
<213> ORGANISM: Homo sapiens

<400> SEQUENCE: 60
tagtaagcaa acaactgagg gaccaaaaaa aaaaaacagg ttttaaagtg acaaggttca     60
aatctagggt aacaaatggc aagatgggag tactcacatg atcaaagaaa tgtaccactg    120
caagcttttt gctgcgcctg gtaaagatgc gctgcacttt agcaattttg ccaaaatggt    180
tctccagaat ggtcctgtcg ttgaggtagt cagggatgtt cttgcactgg atggctgtga    240
cttcagaggg agacaagccc caagactgt ctgtgctctc gcttctgtta ctctgacgcg     300
ccggagttcc tcttagagaa tctaggggtt cagagaatgg acacttaaac catcagatgt    360
ttccaacaac aggaggcacc aactgtgtcg aagcagagga aattttcaga tgtaagacct    420
gctccgatga catgttagaa tccctaatgt ttatgggaga tttatctgaa aaatcaagct    480
aacacccaga gaaacgtatt gaaaacctgc ctgcaggatt tactctatgt gctacatttt    540
cagagctcac cttcttttctt ctctctactt tcagtttctt cctctttatt cacacctgga    600
a                                                                    601

<210> SEQ ID NO 61
<211> LENGTH: 601
<212> TYPE: DNA
<213> ORGANISM: Homo sapiens

<400> SEQUENCE: 61
agaaggcgct tatacatcac ggccgttgct catgcttggg ttaaaaaagg tctcccttac     60
agccagggct caggatccct aggcagctgg gggttggccc ccggggctca gaggttaacc    120
ctcttcctct cacagatggg cctagcggtg ggagcgtttg tggcaagctg cagaaatgag    180
atgcgagaga gagagcccgt ccttcagagt ccacgacagc acaaaggaaa tggccgtggg    240
tgtttcgggt ttagctgtct ttgttcctac acgtttatgt tacctgcaag tggaaattca    300
ccggcacatc ctctcaaaaa ttatattttg tgtaaaaata tttaagcact aaatgaacct    360
ctgagagtcg ggatagcgct tccttggagg ggggaaagtt tggggaggag ggcacggggg    420
ctcccttcct tggagggggag aaagtttggg gaggagggca tggggctcc ctgagggcca    480 gtcatgctgt tcttggtgtg ggtggcagtg acacaggcgt ttgcttaggg acaactgtgc    540
tgttctgact taagtgccag cctgtggaag cgcccactga ctcaagatta gataatctcc    600
c                                                                    601

<210> SEQ ID NO 62
<211> LENGTH: 601
```

```
<212> TYPE: DNA
<213> ORGANISM: Homo sapiens

<400> SEQUENCE: 62
ggatacaact agcctagaaa aaagtcttca aagttcttct aagcattagt tctccaagtg      60
ctccaatgaa ggctaacaac ccaatccaaa gtgaaggctt cttttacttc ttataaacaa     120
tttcataaat ttttgtctta gtatataata aaggataat aagctacaag ataaatgatt      180
aaagattaac caaatttggt attcatgaac taaaacgaac acttttctag attttaaggt     240
gggctctact tcagctcatt actaagatga ctaagcacca tgcaaaattt ggcaatgctg     300
ccgggtctca agcatatata tgaaaaagtc tgcagccaca actaccctaa cagagatttc     360
agaaaggatg ctctaagtct atcatgagtg taaccttaaa tagattactt ttatactgtt     420
ttattcttcc ttttaaactg taaactatat tagtttaata tcatcaattt atagttaagt     480
tagttatttg gttaactcta cagtgtagag ctatgcatat ttgttgtctg cacctttaac     540
tttccagtaa ctaaatgtta cgcgttcggt gttggagaaa tgagacatct actcagtaac     600
t                                                                    601

<210> SEQ ID NO 63
<211> LENGTH: 601
<212> TYPE: DNA
<213> ORGANISM: Homo sapiens

<400> SEQUENCE: 63
aaacggacca caactttctt caaacttctt caaagtttgc atgtctggga gaccaataaa      60
gggcagggca tacgaagtaa gtctgtttag gtcagttgtt tatgggtagg tgcgacttca     120
ttcctgttcg ccctacttgc agacatggta acttagaaca gttcttcaga agctgttcga     180
tggcaacgtg gcggacatgg agctgtgagg ccaaagaatc ttttcttgc acttggtgag     240
ttaactcttc aaaaacttct gtaaaagatt taaaaacttt catttttagt atgcagaaag     300
ccggtgctat gatttatatt tcaagaactc taactgaaat ctatgcattg ggcaaagtgt     360
cacaatgaaa ctgatttgat accaaggaaa cagttctgtt ctctacaaag catatcagtt     420
ctgatcatcc taggcatctg tatactttac atagccaaat ggaatttggc tcttctccat     480
caagtgacta cagagataca cagcaaaaat ggtggttgct actgtagctg agctactttt     540
ctcaattaga atctataaac agattcaatt agtacataat gtgatttatg gacaagaagt     600
g                                                                    601

<210> SEQ ID NO 64
<211> LENGTH: 601
<212> TYPE: DNA
<213> ORGANISM: Homo sapiens

<400> SEQUENCE: 64
ctgcattttg tgtgagtata gctggatccg ctttgattct acaaattagg tgcccttctg      60
tttcttagta atgtcatatt ctctgaccac tgtagccact taagatagtc tcaaatatga     120
ataattttca gtggccatag tggagaagat gctgacccag gaggcttatt ctcacctcca     180
cctcttagac tcacatgtat gatttttttt tctccctacc aaagtggcta gttttgacag     240
cctttaggtt gcagaactgt ttatattcga aagaagacct taccttcata gagcattttc     300
ccgggcagtt gttctgcttt gtgtttttaa tatctactct tattcggagt cccaaaatga     360
gttagcttgg gtagctctca caatgaaaac tgatttcttc gcataaaact ttattctacc     420
tttttgaaaa ccagctggaa atgatgaatg gtggcttcaa cagtaatggt tcacgaagaa     480
```

```
ctgatcgtgt cccatcaat gaggtcttac ccatggcagg gcaatggcgg tctactgtaa    540
ttctgtgttg gttgtagtaa gttggggggaa tatcaggcca agaatcaaca gagctacgtg    600
g                                                                     601

<210> SEQ ID NO 65
<211> LENGTH: 601
<212> TYPE: DNA
<213> ORGANISM: Homo sapiens

<400> SEQUENCE: 65
taaccctatc tagtacaagt tcaattatgt taagctaaaa actttgctgt aaatatttaa     60
atgccaagct caaaaaatca taagggacat cctctcagcc ctaagttcta ttcaccctga    120
tactcaatac atttgaaagt aaaacctcac tttcgaagta acgctgatac tgaagcaagg    180
agatgttgaa tgactcaccc atttcatagc ttttccgtgg caaagcctca ctaaaaccta    240
tctaatccct agctccaatt ctttaatctc catggtgctt ctgattaata gttaaaccac    300
ccggaagtat gttaaggata ctaacatttt caccccgaag tattatcctt cgccatcctc    360
tagaatatgc tatgcaaaga ggcctaaaac aaaataaact gcgacttcag cagctgagaa    420
gtaatgattc ctttcccctc ccacacatca aaacttccta tcctatcccc tcactacttt    480
ttttccttt taaaagtaac aatggtcatt gagaactact aaatcctgca acactcacaa    540
ggtagtatgt acaaccacag ttttcccccg cgatacttca ctgaagtatt caatacagcc    600
a                                                                     601

<210> SEQ ID NO 66
<211> LENGTH: 601
<212> TYPE: DNA
<213> ORGANISM: Homo sapiens

<400> SEQUENCE: 66
cagagacgag agacactttc tttgtacatg tcccacaagc acagttccag gattttggca     60
ctaagtaaac aaataaaaat atgcaacaga cataagagat aatagtaatg tgtattgaga    120
aatataattt tatatagttg ttcctttttc ccaagattct ttattaatat caccaatagt    180
tattactaga aaaactttc agagctagaa agttgccaga acatttcta attgactact    240
gttataatta atattttgaa atgctgagac atttgctagg gtggacagct ccttcaaaac    300
ccggccgtta tctgacgaaa gagcctaggc tcaaataaga attaaacaca agttggaagt    360
aaggtgaggc acagtggaat ttttttagga tggatatagt tttcaataac cttaatttgg    420
aatttttcct ttgggataat gactttgagt ctatagaaat attgtatgca ttatagacga    480
attgatttt taactaaatt ctgaaaggct taagtaaaat gatttgatga tcaagtcaga    540
tgcatttcta aggaagtgag gatcacatta gacagaaagt ttgggtttgg tgtataataa    600
t                                                                     601

<210> SEQ ID NO 67
<211> LENGTH: 601
<212> TYPE: DNA
<213> ORGANISM: Homo sapiens

<400> SEQUENCE: 67
gcaaaccacc cacttctgcc ctctgcccctt cttcccttttt ctcgacaccc tgcggccccc     60
cagtttcagc agagtttatt tggggtgaaa aacaagagat gctcagcgcc tgtgggatgt    120
gtgggctgac tcgtacatta ggatgtgtgt caatctgaaa taacctggcc gttatatgga    180
```

```
tgccttgggg cttgggggt ttctggcagt ctgtcgagcc cgaggtgaat gtccccaagg    240
ctgctggtga atcagatccc tggcgttctc cgttggcagt tcagcccaac agtttctctg    300
ccggccgtgc ctctgcaggt ccctcctctg atctgattgg attaatattt gaatcaatag    360
actgagtcaa gcagaatgtg ggtgggcctc atgcaatcag ctgaagccct gaaaagagca    420
aaagggctgc cccttccccc gaggaggaga gaacccctcc tgccggacgg cctccgaact    480
ggaacatcag cttttttgctg cctttggact tgaactgaaa cattacctct ccctgggtct    540
tgagtctgcc tacgttggca cgggaactac acgttggctc tcttgggccc cagcttgctg    600
a                                                                  601
```

```
<210> SEQ ID NO 68
<211> LENGTH: 601
<212> TYPE: DNA
<213> ORGANISM: Homo sapiens

<400> SEQUENCE: 68
cctttgttct tgttggcatc tgtgtaagag aatccagggc ctgaaccatt gtccactcaa    60
acagaccata cacacctggt ccagttttgt gcatgcctcc cttttccaca gtgtgccact   120
tgctatagtt ctgaacaaaa actcccttgc ccttcggagc tttatttatt tttaatttgc   180
tctgtcattg cattgcatgc aatagaagct tcctggtgga agctcaatgt tctgctcagt   240
cccagacacg ttttcagcca ctgtatcatt gccttaggtt gtggtttccc caaagcagca   300
ccggaggtaa gggcttgtgt gcaggagttc acttgggagg tggctctagg aaatagaagc   360
gagtttccag gaagtgtggg atgaatacgg ggatggggtg ggggcgggg aggaatccaa    420 tatgaatata taatctcata ttgagtataa aaatccaata tgagtatgtt ttccagactg    480
ctgctaagga gaatggtgaa ttattctact gcgacctttt gagggtccac acaatgcctc    540
ccaaaactat ctaccagagg gtggatagga agcattgatc catggcttat attccccatt    600
g                                                                  601
```

```
<210> SEQ ID NO 69
<211> LENGTH: 33
<212> TYPE: DNA
<213> ORGANISM: Artificial Sequence
<220> FEATURE:
<223> OTHER INFORMATION: Synthetic oligodeoxynucleotide primer

<400> SEQUENCE: 69
acactctttc cctacacgac gctcttccga tct                                33
```

```
<210> SEQ ID NO 70
<211> LENGTH: 33
<212> TYPE: DNA
<213> ORGANISM: Artificial Sequence
<220> FEATURE:
<223> OTHER INFORMATION: Synthetic oligodeoxynucleotide primer

<400> SEQUENCE: 70
gatcggaaga gctcgtatgc cgtcttctgc ttg                                33
```

```
<210> SEQ ID NO 71
<211> LENGTH: 34
<212> TYPE: DNA
<213> ORGANISM: Artificial Sequence
<220> FEATURE:
<223> OTHER INFORMATION: Synthetic oligodeoxynucleotide primer

<400> SEQUENCE: 71
```

```
caagcagaag acggcatacg agctcttccg atct                            34

<210> SEQ ID NO 72
<211> LENGTH: 58
<212> TYPE: DNA
<213> ORGANISM: Artificial Sequence
<220> FEATURE:
<223> OTHER INFORMATION: Synthetic oligodeoxynucleotide primer

<400> SEQUENCE: 72
aatgatacgg cgaccaccga gatctacact ctttccctac acgacgctct tccgatct   58

<210> SEQ ID NO 73
<211> LENGTH: 33
<212> TYPE: DNA
<213> ORGANISM: Artificial Sequence
<220> FEATURE:
<223> OTHER INFORMATION: Synthetic oligodeoxynucleotide primer

<400> SEQUENCE: 73
acactctttc cctacacgac gctcttccga tct                             33

<210> SEQ ID NO 74
<211> LENGTH: 33
<212> TYPE: DNA
<213> ORGANISM: Artificial Sequence
<220> FEATURE:
<223> OTHER INFORMATION: Synthetic oligodeoxynucleotide primer

<400> SEQUENCE: 74
gatcggaaga gctcgtatgc cgtcttctgc ttg                             33

<210> SEQ ID NO 75
<211> LENGTH: 34
<212> TYPE: DNA
<213> ORGANISM: Artificial Sequence
<220> FEATURE:
<223> OTHER INFORMATION: Synthetic oligodeoxynucleotide primer

<400> SEQUENCE: 75
caagcagaag acggcatacg agctcttccg atct                            34

<210> SEQ ID NO 76
<211> LENGTH: 58
<212> TYPE: DNA
<213> ORGANISM: Artificial Sequence
<220> FEATURE:
<223> OTHER INFORMATION: Synthetic oligodeoxynucleotide primer

<400> SEQUENCE: 76
aatgatacgg cgaccaccga gatctacact ctttccctac acgacgctct tccgatct   58

<210> SEQ ID NO 77
<211> LENGTH: 20
<212> TYPE: DNA
<213> ORGANISM: Artificial Sequence
<220> FEATURE:
<223> OTHER INFORMATION: Synthetic oligodeoxynucleotide primer

<400> SEQUENCE: 77
cctcaaaaga aaccgtgcat                                            20

<210> SEQ ID NO 78
<211> LENGTH: 26
<212> TYPE: DNA
<213> ORGANISM: Artificial Sequence
```

```
<220> FEATURE:
<223> OTHER INFORMATION: Synthetic oligodeoxynucleotide primer

<400> SEQUENCE: 78
agattaatgg ttgctaagga ctggat                                          26

<210> SEQ ID NO 79
<211> LENGTH: 29
<212> TYPE: DNA
<213> ORGANISM: Artificial Sequence
<220> FEATURE:
<223> OTHER INFORMATION: Synthetic oligodeoxynucleotide probe

<400> SEQUENCE: 79
caccagcagt aactccccac aacctcttt                                       29

<210> SEQ ID NO 80
<211> LENGTH: 22
<212> TYPE: DNA
<213> ORGANISM: Artificial Sequence
<220> FEATURE:
<223> OTHER INFORMATION: Synthetic oligodeoxynucleotide primer

<400> SEQUENCE: 80
gtgcacctga ctcctgagga ga                                              22

<210> SEQ ID NO 81
<211> LENGTH: 20
<212> TYPE: DNA
<213> ORGANISM: Artificial Sequence
<220> FEATURE:
<223> OTHER INFORMATION: Synthetic oligodeoxynucleotide primer

<400> SEQUENCE: 81
cttgatacca acctgcccag                                                 20

<210> SEQ ID NO 82
<211> LENGTH: 25
<212> TYPE: DNA
<213> ORGANISM: Artificial Sequence
<220> FEATURE:
<223> OTHER INFORMATION: Synthetic oligodeoxynucleotide probe

<400> SEQUENCE: 82
aggtgaacgt ggatgaagtt ggtgg                                           25

<210> SEQ ID NO 83
<211> LENGTH: 601
<212> TYPE: DNA
<213> ORGANISM: Homo sapiens

<400> SEQUENCE: 83
caaattcttc ccaagtactg tttcctttcc tcaattcctg gcctagcaag tctagaaaga     60
aaacaaaaag aatgtaaaat gttcttggtt gactttactc ttaattacta aaaagcaaac    120
agagaaaatt aaaatcaaac acatgcaaaa aattcttcta gagccttgca cacaatgcca    180
gttcttgaaa tatttcataa agcaaagcta atgaaataaa caaagacgtg gctgaaagga    240
tatgcattgt actgtgctta tggagccaca ttgctcactg catctctcgc tccactgccg    300
ccgggctcat ctgccagaag cctgttcctg agctgattgg ggttctggtc cagggtccc    360 aaggagcgag gcccaagctc aggaggacaa agaacgacca cctggaaagt ggcaaaaatc    420
tgtaaaaaaa taaatctgat gtgggcccaa ggggcacctg tctcaagag caaacgctgt    480 gtccagagcc tcatgtccgg aggcccagcc cgactccctg gctcttacag ccccgaagcc    540
```

```
cagagaccac cccagcccga ctccctggct gagacttccc gcccggatgc cgtgagatcg    600
t                                                                   601
```

METHODS FOR THE DIAGNOSIS OF FETAL DISEASE

CROSS REFERENCE TO RELATED APPLICATIONS

This claims the benefit of U.S. Provisional Application No. 61/361,824, filed Jul. 6, 2010, which is incorporated by reference herein in its entirety.

FIELD

This related to the field of prenatal diagnosis, specifically to the diagnosis of fetal aneuploidy, such as an aneuploidy of chromosome 13, 18, 21, X or Y.

BACKGROUND

Definitive prenatal diagnosis of fetal aneuploidy is currently performed using chorionic villus sampling (CVS) or amniocentesis. These are invasive, expensive and somewhat risky approaches that must be performed by experienced clinicians and are generally only offered to expectant mothers considered to be at elevated risk of carrying a genetically abnormal fetus. Low cost minimally invasive screening is routinely used across the maternal age range but this is based upon the quantification of serum proteins that are surrogate markers of the underlying genetic abnormality and do not achieve desirable levels of sensitivity and specificity (Wapner et al., N. Eng J. Med. 349: 1405-13, 2003; Alfirevic and Neilson, BMJ 326: 811-2, 2004; Malone et al., N Engl. J. Med 353: 2001-11, 2005).

An attractive alternative involves the analysis of placentally-derived nucleic acids in maternal plasma to characterize specific features of the fetal genome (Lo, Ann. NY. Acad. Sci. 1137: 140-3, 2008). However, because of the technical challenge of distinguishing maternally inherited fetal alleles from endogenous maternal DNA this approach has largely been limited to the detection of paternally inherited disease-causing mutations (Zimmermann et al., Methods Mol Med 132: 43-49, 2007; Li et al., Prenat Diag 27: 11-7, 2007). Differential DNA methylation patterns between the placental and maternal leukocyte genomes at distinct loci have been used to determine the fetal genotype (Lo et al., PNAS 104: 13116-21, 2007; Lo et al., Nat Med 13:218-23, 2007). Specific polymerase chain reaction (PCR)-based assays were used that amplify a given methylated (placental), but not an unmethylated (maternal) locus (or visa versa) in DNA obtained from maternal plasma (Tsui et al., Prenat Diag 27: 1212-8, 2007; Tong et al., Clin Chem 53: 1906-14, 2007; Chan et al., Clin Chem 52: 2211-8, 2006; Tong et al., Clin Chem 52: 2194-202, 2006). However, a need remains for sensitive and specific non-invasive methods that can be used to diagnose fetal conditions, such as aneuploidy, using the placental methylome.

SUMMARY

Methods are provided for detecting a chromosome abnormality such as an aneuploidy in a fetus. These methods can be used to detect trisomy 13, 8, 21, X and/or Y, amongst other aneupoloidies. In some embodiments, the methods detect a trisomy of chromosome 13, 8, and/or 21. In other embodiments the methods detect Turner's Syndrome (XO).

In some embodiments, the methods include selectively purifying fetal DNA from a maternal biological sample using the methylation status of a CpG containing genomic sequence. The allele frequency is then determined in the purified fetal DNA, thereby detecting aneuploidy in the fetus.

In some embodiments, methods are provided for detecting an aneuploidy in a fetus. The methods include (a) selectively purifying fetal DNA from a maternal biological sample using the methylation status of a CpG containing genomic sequence, wherein the CpG-containing genomic sequence is at least 15 nucleotides in length, comprises at least one CpG dinucleotide, and is within a region on chromosome 13, 18 or 21, and wherein the CpG-containing genomic sequence comprises at least 15 nucleotides of at least one of the nucleic acid sequences set forth as any one of SEQ ID NOs: 1-68 or 83-85; and (b) genotyping the fetus using the purified fetal DNA, thereby detecting aneuploidy in the fetus.

In some, but not all, embodiments, the fetus is genotyped using a genetic marker, such as a single nucleotide polymorphism (SNP) that is genetically linked to any one of SEQ ID NOs: 1-68 or 83-85. In some examples, the SNP is within about 150 base pairs of at least one of SEQ ID NOs: 1-68 or 83-85. Other genetic markers are also of use, such as a short tandem repeat (STR).

In some embodiments, the allelic ratio is determined. In some examples, an allelic ratio of 1:2 or 2:1 indicates that the fetus is aneuploid. In other examples, an allelic ratio of 0:1 or 1:0 indicates that the fetus is aneuploidy.

The foregoing and other features and advantages will become more apparent from the following detailed description of several embodiments, which proceeds with reference to the accompanying figures.

BRIEF DESCRIPTION OF THE FIGURES

FIG. 2A is a summary of pyrosequencing analysis for four CpG sites across chromosomes 13, 18 and 21. Sample n=10 CVS and 10 MBC. FIG. 2b is a summary of Mass Array/Epityper analysis for CpG sites across chromosomes 13, 18 and 21. Sample n=23 CVS and 23 MBC. For both data sets, fully methylated control samples were obtained from Millipore (part number S7821). The Y axis is methylation rate, i.e., the proportion of CpG sites that are methylated. The whiskers above each bar are the upper boundaries of the confidence intervals of the estimated methylation rates.

SEQUENCE LISTING

Figure 1:
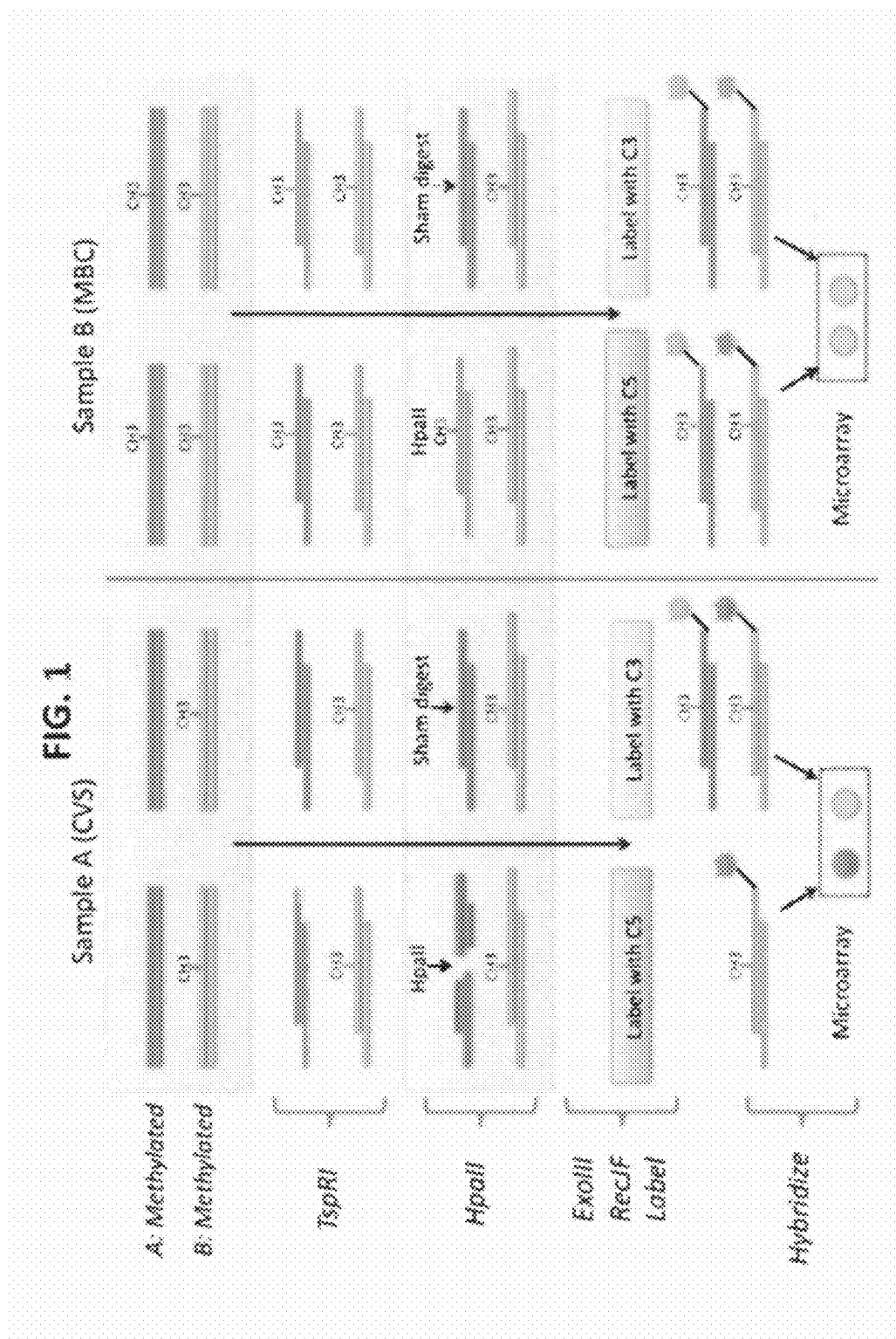
FIG. 1 is a schematic diagram of the reaction scheme used to prepare libraries of genomic DNA fragments that are depleted for hypomethylated CpG sites in either CVS or MBC tissues.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-83157-03sequence.txt, 64 kB, Jul. 5, 2011], and incorporated by reference herein. In the accompanying sequence listing:

SEQ ID NOs: 1-68 and 83 are nucleic acid sequences of regions of human chromosomal DNA that are methylated in a fetal genome as compared to a maternal genome.

SEQ ID NOs: 69-82 are primer sequences.

DETAILED DESCRIPTION

Methods are provided herein for detecting an aneuploidy in a fetus. These methods include selectively purifying fetal DNA from a maternal biological sample using the methylation status of a CpG containing genomic sequence. The copy number of a DNA sequence included in the fetal genome is then determined.

In some embodiments, the CpG-containing genomic sequence is at least 15 nucleotides in length. In some embodiments, the CpG containing sequence comprises at least one CpG dinucleotide, and is within a region on chromosome 13, 18, 21, X or Y. In specific examples, the CpG-containing genomic sequence comprises at least 15 nucleotides of at least one of the nucleic acid sequences set forth as SEQ ID NOs: 1-68 or 83-85. In other specific non-limiting examples, the methylation status of the entirety of one or more of SEQ ID NO:s: 1-68 or 83-85 can also be determined.

These methods can include genotyping the fetus using the purified fetal DNA, thereby detecting aneuploidy of chromosome 13, 18 or 21 in the fetus. However, these methods can be applied to other chromosomes, including the X chromosome.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Allelic ratio: An allele is one DNA sequence of a given genetic locus. The number of each alleles in an individual is an allelic ratio. Generally, an allelic ratio of 2:0 or 0:2 is a homozygote, and an allelic ratio of 1:1 is a heterozygote at the locus. An allelic ratio of 1:2 or 2:1 indicates that a subject, such as a fetus, is aneuploid. An allelic ratio of 1:0 or 0:1, such as for the X chromosome ratio in a subject that is phenotypically female, can also indicate that the subject is aneuploid.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881); repair chain reaction amplification (see PCT Publication No. WO 90/01069); ligase chain reaction amplification (see European patent publication No. EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134), amongst others.

Allele (Haplotype): A 5' to 3' sequence of nucleotides found at a set of one or more polymorphic sites in a locus on a single chromosome from a single individual. "Allelic pair" is the two alleles found for a locus in a single individual. With regard to a population, alleles are the ordered, linear combination of polymorphisms (e.g., single nucleotide polymorphisms (SNPs) in the sequence of each faun of a gene (on individual chromosomes) that exist in the population. "Haplotyping" is a process for determining one or more alleles in an individual and includes use of family pedigrees, molecular techniques and/or statistical inference. "Haplotype data" or "allele data" is the information concerning one or more of the following for a specific gene: a listing of the allelic pairs in an individual or in each individual in a population; a listing of the different alleles in a population; frequency of each allele in that or other populations, and any known associations between one or more alleles and a trait.

Aneuploidy: An abnormal number of chromosomes. Monosomy refers to the presence of only one chromosome, wherein two copies is normal. Monosomy of the X chromosome (45,X) causes Turner's syndrome. Trisomy refers to the presence of three copies (instead of the normal two) of specific chromosomes. Trisomy 21 causes Down's syndrome. Tripsome 10 and Trisomy 31, known as Edwards and Patau Syndrome, respectively, are two autosomal abnormalities. Trisomy X has also been observed in humans (47, XXX).

Germline aneuploidy can be detected through karyotyping, a process in which a sample of cells is fixed and stained to create the typical light and dark chromosomal banding pattern and a picture of the chromosomes is analyzed. Other techniques include Fluorescence In Situ Hybridization (FISH), Quantitative Polymerase Chain Reaction (PCR) of Short Tandem Repeats, Quantitative Fluorescence PCR (QF-PCR), Quantitative Real-time PCR(RT-PCR) dosage analysis, Quantitative Mass Spectrometry of Single Nucleotide Polymorphisms, and Comparative Genomic Hybridization (CGH).

Array: An arrangement of molecules, such as biological macromolecules (such as polypeptides or nucleic acids) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from a few (such as three) to at least six, at least 20, at least 25, or more. In particular examples, an array includes nucleic acid molecules, such as oligonucleotide sequences that are at least 15 nucleotides in length, such as about 15-40 nucleotides in length, such as at least 18 nucleotides in length, at least 21 nucleotides in length, or even at least 25 nucleotides in length. In one example, the molecule includes oligonucleotides attached to the array via their 5'- or 3'-end.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Bi-Allelic Single Nucleotide Polymorphism: A polymorphism (one nucleotide) that differs between the two alleles in an individual. Thus, the individual is heterozygous at this genetic loci.

Bisulfite: All types of bisulfites, such as sodium bisulfate, that are capable of chemically converting a cytosine (C) to a uracil (U) without chemically modifying a methylated cytosine and therefore can be used to differentially modify a DNA sequence based on the methylation status of the DNA.

Chromosomal abnormality: A chromosome with DNA deletions or duplications and chromosomal aneuploidy. The term also encompasses translocation of extra chromosomal sequences to other chromosomes.

Chromosomal aneuploidy or aneuploidy: The abnormal presence (hyperploidy) or absence (hypoploidy) of a chromosome, such as chromosome 13, 18 or 21. In some cases, the abnormality can involve more than one chromosome, or more than one portion of one or more chromosomes. The most common chromosome aneuploidy is trisomy, such as trisomy 21, where the genome of an afflicted patient has three chromosomes 21, as compared to two chromosomes 21. In rarer cases, the patient may have an extra piece of chromosome 21 (less than full length) in addition to the normal pair. In yet other cases, a portion of chromosome 21 may be translocated to another chromosome, such as chromosome 14. In this example, chromosome 21 is referred as the "chromosome relevant to the chromosomal aneuploidy" and a second, chromosome that is present in the normal pair in the patient's genome, for example chromosome 1, is a "reference chromosome." There are also cases where the number of a relevant chromosome is less than the normal number of 2. Turner syndrome is one example of a chromosomal aneuploidy where the number of X chromosome in a female subject has been reduced from two to one.

CpG-containing genomic sequence: A segment of DNA sequence at a defined location in the genome of an individual such as a human fetus or a pregnant woman. Typically, a "CpG-containing genomic sequence" is at least 15 nucleotides in length and contains at least one cytosine. In some embodiments, a CpG containing sequence can be at least 30, 50, 80, 100, 150, 200, 250, or 300 nucleotides in length and contains at least 2, 5, 10, 15, 20, 25, or 30 cytosines. For any specific "CpG-containing genomic sequence" at a given location, for example, within a region centering around a given genetic locus on chromosome 21 nucleotide sequence variations can exist from individual to individual and from allele to allele even for the same individual. Typically, such a region centering around a defined genetic locus (e.g., a CpG island) contains the locus as well as upstream and/or downstream sequences. Each of the upstream or downstream sequence (counting from the 5' or 3' boundary of the genetic locus, respectively) can be as long as 1 kb, in other cases may be as long as 5 kb, 2 kb, 750 bp, 500 bp, 200 bp, or 100 bp. A "CpG-containing genomic sequence" can encompass a coding or a non-coding, nucleic acid sequence, and thus can include a nucleotide sequence transcribed (or not transcribed) for protein production. Thus, a CpG containing genomic sequence can be a nucleotide sequence can be a protein-coding sequence, a non protein-coding sequence or a combination thereof.

CpG island: A segment of DNA sequence in which the frequency of CpG dinucleotide sequences is higher than other dinucleotide sequences. Generally, a CpG island is found in a genome that has a minimal length, a minimal GC content, and a minimal ratio of observed CpG frequency/expected CpG frequency (OCF/ECF).

In one embodiment, a CpG island has (1) at least 200 nucleotides in length, (2) has a greater than 50% GC content, and (3) an OCF/ECF ratio greater than 0.6 (see Takai et al., Proc. Natl. Acad. Sci. U.S.A. 99:3740-3745, 2002). In another embodiment, a CpG island has (1) at least 400 nucleotides in length; (2) a greater than 50% GC content; and (3) an OCF/ECF ratio greater than 0.6 (see Yamada et al. (Genome Research 14:247-266, 2004). A "CpG island" on chromosome 13, 18 or 21 can fits the CpG island profiles provided by any one of the currently available computational programs designed for scanning chromosomes based on the above stated criteria, encompassing results obtained when using window sizes of 100, 200, or 300 nucleotides and shift or step sizes of 1, 2, or 3 nucleotides in the screening process. The individual CpG islands named in this disclosure are further defined by including the sequence, but can also be identified by contig number, version and region at GENBANK®, chromosomal location relative to the chromosome 13, 18 or 21 sequence, respectively, of the Human May 2004 (hg17) assembly of the UCSC Genome Browser (See the UCSC website).

Control DNA: Genomic DNA obtained from an individual that is used for comparative purposes, such as DNA from a healthy individual who does not have a chromosomal abnormality. In some embodiments, a control DNA sample can be obtained from plasma of a female carrying a healthy fetus who does not have a chromosomal abnormality, which can serve as a negative control. When certain chromosome anomalies are known, the control can also be established standards that are indicative of a specific disease or condition.

To screen for three different chromosomal aneuploidies in a maternal plasma of a pregnant female, a panel of control DNAs that have been isolated from plasma of mothers who are known to carry a fetus with, for example, chromosome 13, 18, or 21 trisomy, and a mother who is pregnant with a fetus who does not have a chromosomal abnormality can be used as a positive control.

Copy number: The number of copies of a section of DNA in a genome. Copy number analysis usually refers to the process of analyzing data produced by a test for DNA copy number variation in patient's sample. Such analysis helps detect chromosomal copy number variation that may cause or may increase risks of various critical disorders. Copy number variation can be detected with various types of tests, including, but not limited to, such as methylation status, fluorescent in situ hybridization, comparative genomic hybridization high-resolution array-based tests based on array comparative genomic and SNP array technologies. The methods disclosed herein can be used to determine the copy number of a specific locus of interest.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal (termination codon). The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a protein, or a fragment thereof, encompasses both the sense strand and its reverse complement. Thus, for instance, it is appropriate to generate probes or primers from the reverse complement sequence of the disclosed nucleic acid molecules.

Differentially Modifies (methylated or non-methylated DNA): A reagent that modifies methylated or non-methylated DNA, respectively, in a process through which distinguishable products result from methylated and non-methylated DNA, thereby allowing the identification of the DNA methylation status. Such processes may include, but are not limited to, chemical reactions (such as conversion by bisulfate) and enzymatic treatment (such as cleavage by a methylation-dependent endonuclease), or an antibody that specifically binds a methylated (or non-methylated) DNA sequence. Thus, an enzyme that preferentially cleaves or digests methylated DNA is one capable of cleaving or digesting a DNA molecule at a significantly higher efficiency when the DNA is methylated, whereas an enzyme that preferentially cleaves or digests unmethylated DNA exhibits a significantly higher efficiency when the DNA is not methylated.

Epigenetic status: Any structural feature at the molecular level of a nucleic acid (e.g., DNA or RNA) other than the primary nucleotide sequence. For instance, the epigenetic state of a genomic DNA may include its secondary or tertiary structure determined or influenced by, for example, its methylation pattern or its association with cellular proteins, such as histones, and the modifications of such proteins, such as acetylation, deacetylation, and methylation.

Gene: A segment of DNA that contains the coding sequence for a protein, wherein the segment may include promoters, exons, introns, and other untranslated regions that control expression.

Genotype: An unphased 5' to 3' sequence of nucleotide pair(s) found at a set of one or more polymorphic sites in a locus on a pair of homologous chromosomes in an individual. "Genotyping" is a process for determining a genotype of an individual.

Genomic target sequence: A sequence of nucleotides located in a particular region in the human genome that corresponds to one or more specific genetic abnormalities, such as a nucleotide polymorphism, a deletion, an insertion, or an amplification. The target can be for instance a coding sequence; it can also be the non-coding strand that corresponds to a coding sequence. The target can also be a non-coding sequence, such as an intronic sequence.

Heterozygous: An organism is heterozygous for a particular allele when two different alleles occupy the gene's position (locus) on the homologous chromosomes. The cell or organism is called a heterozygote.

Hybridization: Oligonucleotides and their analogs hybridize by hydrogen bonding, which includes Watson-Crick, Hoogsteen or reversed Hoogsteen hydrogen bonding, between complementary bases. Generally, nucleic acids consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to a specific genetic locus, so it specifically hybridizes with a mutant allele (and not the reference allele) or so that it specifically hybridizes with a reference allele (and not the mutant allele).

"Specifically hybridizable" and "specifically complementary" are terms that indicate a sufficient degree of complementarity such that stable and specific binding occurs between the oligonucleotide (or its analog) and the DNA or RNA target, such that the target can be distinguished. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization. In one example, an oligonucleotide is specifically hybridizable to DNA or RNA nucleic acid sequences including an allele of a gene, wherein it will not hybridize to nucleic acid sequences containing a polymorphism.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though wash times Also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11.

The following is an exemplary set of hybridization conditions and is not limiting:

Very High Stringency (Detects Sequences that Share at Least 90% Identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Detects Sequences that Share at Least 80% Identity)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (Detects Sequences that Share at Least 50% Identity)

Hybridization: 6×SSC at RT to 55° C. for 16-20 hours

Wash at least twice: 2×-3×SSC at RT to 55° C. for 20-30 minutes each.

Increase or a Decrease: A significantly significant positive or negative change, respectively, in quantity from a control value. An increase is a positive change, such as a 50%, 100%, 200%, 300%, 400% or 500% increase as compared to the control value. A decrease is a negative change, such as a 50%, 100%, 200%, 300%, 400% or 500% decrease as compared to a control value.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Locus: A location on a chromosome or DNA molecule corresponding to a gene or a physical or phenotypic feature, where physical features include polymorphic sites.

Maternal allele frequency: The ratio, represented as a percent, of a maternal allele to the total amount of alleles present (both paternal and maternal). The term "paternal allele frequency" refers to the ratio, represented as a percent, of a paternal allele to the total amount of alleles present (both paternal and maternal).

Methylation status: The state of methylation of a genomic sequence. This refers to the characteristics of a DNA segment at a particular genomic locus relevant to methylation. Such characteristics include, but are not limited to, whether any of the cytosine (C) residues within this DNA sequence are methylated, location of methylated C residue(s), percentage of methylated C at any particular stretch of residues, and allelic differences in methylation. The methylation profile affects the relative or absolute concentration of methylated C or unmethylated C at any particular stretch of residues in a biological sample.

Methyl-sensitive enzymes: DNA restriction endonucleases that are dependent on the methylation state of their DNA recognition site for activity. For example, there are methyl-sensitive enzymes that cleave at their DNA recognition sequence only if it is not methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated. As used herein, the terms "cleave", "cut" and "digest" are used interchangeably.

Methyl-sensitive enzymes that digest unmethylated DNA suitable for use in methods of the invention include, but are not limited to, HpaII, HhaI, MaeII, BstUI and AciI. One enzyme is HpaII that cuts only the unmethylated sequence CCGG. Enzymes that digest only methylated DNA include, but are not limited to, DpnI, which cuts at a recognition sequence GATC, and McrBC, which belongs to the family of AAA proteins (New England BioLabs, Inc., Beverly, Mass.).

Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Promega Corporation, Boehringer-Mannheim, and the like. Sambrook et al. (See Sambrook et al., Molecular Biology: A Laboratory Approach, Cold Spring Harbor, N.Y. 1989) provide a general description of methods for using restriction enzymes and other enzymes.

Mutation: Any change of a nucleic acid sequence as a source of genetic variation. For example, mutations can occur within a gene or chromosome, including specific changes in non-coding regions of a chromosome, for instance changes in or near regulatory regions of genes. Types of mutations include, but are not limited to, base substitution point mutations (which are either transitions or transversions), deletions, and insertions. Missense mutations are those that introduce a different amino acid into the sequence of the encoded protein; nonsense mutations are those that introduce a new stop codon; and silent mutations are those that introduce the same amino acid often with a base change in the third position of the codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

In several examples, oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 70 bases, for example about 10-25 bases, such as 12, 15 or 20 bases.

Polymorphic marker: A segment of genomic DNA that exhibits heritable variation in a DNA sequence between individuals. Such markers include, but are not limited to, single nucleotide polymorphisms (SNPs), restriction fragment length polymorphisms (RFLPs), short tandem repeats, such as di-, tri- or tetra-nucleotide repeats (STRs), and the like. Polymorphic markers can be used to specifically differentiate between a maternal and paternal allele in the enriched fetal nucleic acid sample.

A "methyl-polymorphic marker" refers to a polymorphic marker that is adjacent to differentially methylated DNA regions of fetal and maternal DNA. The term adjacent refers to a marker that is within 1-3000 base pairs, preferably 1000 base pairs, such as 150 base pairs, 100 base pairs or 50 base pairs from a differentially methylated nucleotide.

Polymorphism: A variation in a gene sequence. The polymorphisms can be those variations (DNA sequence differences) which are generally found between individuals or different ethnic groups and geographic locations which, while having a different sequence, produce functionally equivalent gene products. Typically, the term can also refer to variants in the sequence which can lead to gene products that are not functionally equivalent. Polymorphisms also encompass variations which can be classified as alleles and/or mutations which can produce gene products which may have an altered function. Polymorphisms also encompass variations which can be classified as alleles and/or mutations which either produce no gene product or an inactive gene product or an active gene product produced at an abnormal rate or in an inappropriate tissue or in response to an inappropriate stimulus. Alleles are the alternate forms that occur at the polymorphism.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation.

Probes and primers: A probe comprises an isolated nucleic acid capable of hybridizing to a target nucleic acid. A detectable label or reporter molecule can be attached to a probe or primer. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 15 nucleotides in length, such as at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, or more contiguous nucleotides complementary to the target nucleic acid molecule, such as 20-70 nucleotides, 20-60 nucleotides, 20-50 nucleotides, 20-40 nucleotides, or 20-30 nucleotides.

Primers are short nucleic acid molecules, for instance DNA oligonucleotides are 10 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 55, 60, 65, 70 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, or more contiguous nucleotides complementary to the target nucleic acid molecule to be amplified, such as a primer of 15-70 nucleotides, 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein. It is also appropriate to generate probes and primers based on fragments or portions of these disclosed nucleic acid molecules, for instance regions that encompass the identified polymorphisms of interest. PCR primer pairs can be derived from a known sequence by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Sample: A sample, such as a biological sample, is a sample obtained from a subject. As used herein, biological samples include all clinical samples useful for detection of fetal aneuploidy, including, but not limited to, cells, tissues, and bodily fluids, such as: blood; derivatives and fractions of blood, such as serum; urine; sputum; or CVS samples. In a particular example, a sample includes blood obtained from a human subject, such as whole blood or serum.

Sequence identity/similarity: The identity/similarity between two or more nucleic acid sequences, or two or more amino acid sequences, is expressed in terms of the identity or similarity between the sequences. Sequence identity can be measured in Wilms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to -1; -r is set to 2; and all other options are left at their default setting. For example, the following command can be used to generate an output file containing a comparison between two sequences: C:\B12seq -i c:\seq1.txt -j c:\seq2.txt -p blastn -o c:\output.txt -q -1 -r 2.

To compare two amino acid sequences, the options of B12seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\B12seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, at least 70%, at least 80%, at least 90%, at least 95%, at least 98%, or at least 99% sequence identity determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid. One of skill in the art will appreciate that the particular sequence identity ranges are provided for guidance only.

Short Tandem Repeat: a pattern of two or more nucleotides are repeated and the repeated sequences are directly adjacent to each other. The pattern can range in length from 2 to 16 base pairs (bp) (for example $(CATG)_n$ in a genomic region) and is typically in the non-coding intron region. A short tandem repeat polymorphism (STRP) occurs when homologous STR loci differ in the number of repeats between individuals. By identifying repeats of a specific sequence at specific locations in the genome, it is possible to create a genetic profile of an individual. There are currently over 10,000 published STR sequences in the human genome.

Single nucleotide polymorphism (SNP): The polynucleotide sequence variation present at a single nucleotide residue within different alleles of the same genomic sequence. This variation may occur within the coding region or non-coding region (i.e., in the promoter region) or an intergenic (between genes) sequence of a genomic sequence. Detection of one or more SNP allows differentiation of different alleles of a single genomic sequence. All common SNPs have only two alleles.

SNPs within a coding sequence will not necessarily change the amino acid sequence of the protein that is produced, due to degeneracy of the genetic code. A SNP in which both forms lead to the same polypeptide sequence is termed "synonymous" (sometimes called a silent mutation)—if a different polypeptide sequence is produced they are "nonsynonymous". A nonsynonymous change may either be missense or "nonsense", where a missense change results in a different amino acid, while a nonsense change results in a premature stop codon.

Standard control: A value reflective of the ratio, or the amount or concentration of a fetal genomic sequence located on a chromosome relevant to a particular chromosomal aneuploidy (such as trisomy 13, 18, or 21) over the amount or concentration of a fetal genetic marker located on a reference chromosome, as the amounts or concentrations are found in a biological sample (for example, blood, plasma, or serum) from an average, healthy pregnant woman carrying a chromosomally normal fetus. A "standard control" can be determined differently and represent different value depending on the context in which it is used. For instance, when used in an epigenetic-genetic dosage method where an epigenetic marker is measured against a genetic marker, the "standard control" is a value reflective of the ratio, or the amount or concentration of a fetal genomic sequence located on a chromosome relevant to a particular chromosomal aneuploidy (for example, trisomy 13, 18, or 21) over the amount or concentration of a fetal genetic marker located on a reference chromosome, as the amounts or concentrations are found in a biological sample (such as blood, plasma, or serum) from an average, healthy pregnant woman carrying a chromosomally normal fetus. In some embodiments, a standard control is determined based on an average healthy pregnant woman at a certain gestational age.

Subject: Living multi-cellular vertebrate organisms, a category that includes human and non-human mammals (such as laboratory or veterinary subjects).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Assessing Fetal Aneuploidy Using a CpG-Containing Genomic Sequence

The present methods utilize an assessment of the methylation status of a CpG-containing genomic sequence in fetal DNA, in order to detect a fetal anuploidy. Basic texts disclosing the general methods of use include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994), which are incorporated herein by reference. Any one of the sequences identified herein, including SEQ ID NO: 1-68 and 83-85 and portions thereof, are examples of sequences that can be used to detect fetal aneuploidy.

In some embodiments, the methods include (a) selectively purifying fetal DNA from a maternal biological sample using the methylation status of a CpG containing genomic sequence, wherein the CpG-containing genomic sequence is at least 15 nucleotides in length, comprises at least one CpG dinucleotide, and is within a region on chromosome 13, 18 or 21. In some examples, the CpG-containing genomic sequence comprises at least 15 nucleotides of a nucleic acid sequence set forth as any one of SEQ ID NOs: 1-68. The fetus is genotyped using the purified fetal DNA to detect aneuploidy in the fetus. The methods can include the use of more than one of the CpG-containing genomic sequences. Thus, the method can in the use of 1, 2, 3, 4, 5, 6, 7, 8, 9, 10, 15, 20, 25, 30, 35, 40, 45, 50, 55, 60, 65 or all of SEQ ID NO: 1-68 and/or SEQ ID NO: 83 (or a portion thereof). Thus, the methods can utilize at least 15, at least 20, at least 30, at least 40, at least 50 or at least 60 nucleotides of one or more of SEQ ID NOs: 1-68 and 83.

In some embodiments, the method comprises (a) determining in a biological sample taken from the pregnant woman the amount of a methylation of a CpG containing DNA of fetal origin, wherein the CpG containing DNA is located on a chromosome relevant to the chromosomal aneuploidy or within a section of a chromosome relevant to the chromosomal aneuploidy, and wherein the methylation of the CpG containing DNA of fetal origin is distinguished from its counterpart CpG containing DNA of maternal origin due to differential DNA methylation; (b) determining the amount of a genetic marker of fetal origin in the sample, wherein the genetic marker is located on a reference chromosome, and wherein the genetic marker of fetal origin is distinguished from its counterpart of maternal origin in the sample due to difference in polynucleotide sequence, or the genetic marker does not exist in the maternal genome; (c) determining the ratio of the amounts from (a) and (b); and (d) comparing the ratio with a standard control, wherein the ratio higher or lower than the standard control indicates the presence of the chromosomal aneuploidy in the fetus. Typically, the standard control value approximates the expected gene or chromosome dosage or ratio in the human genome, although slight variations may exist depending on the specific methodology used in the detection method. In some cases, the sample is maternal whole blood, serum, plasma, urine, amniotic fluid, genital tract lavage fluid, placental-tissue sample, chorionic villus sample, or a sample containing fetal cells isolated from maternal blood. In other cases, the sample is any sample that contains fetal nucleic acids. In some embodiments, step (a) includes treating the sample with a reagent that differentially modifies methylated and unmethylated DNA. Such reagent may comprise bisulfite or a protein or chemical that binds to DNA based on methylation status; or the reagent may comprise a restriction enzyme that either preferentially cleaves methylated DNA or preferentially cleaves unmethylated DNA. In some embodiments, more than one methylation marker or more than one genetic marker may be used. Thus, in some specific non-limiting examples, 2, 3, 4, 5, 6, 7, 8, 9, 10, 11, 12, 13, 14 or 15 genetic markers can be utilized.

Fetal DNA co-exists with maternal DNA in the acellular portion of a pregnant woman's blood (for example, serum or plasma). DNA from fetal origin and maternal origin can be distinguished to ensure accurate results in fetal DNA-based diagnosis. U.S. Published Patent Application No. 2003/0044388, incorporated herein by reference discloses that fetal and maternal DNA can be distinguished by their different methylation profiles. U.S. Published Patent Application No. 2003/0211522, incorporated herein by reference provides methods wherein methylation markers can be used for prenatal diagnosis.

In additional embodiments, step (a) or step (b) may include the process of amplification of the methylation marker and/or the genetic marker, especially the methylation marker and the genetic marker of the fetal origin. As one example, the amplification is by a polymerase chain reaction (PCR), such as a methylation-specific PCR; or the amplification may be a nucleic acid sequence-specific amplification.

Fetal DNA can be hypomethylated relative to adult DNA reflecting transcriptional silencing of specific genes expressed early in development. One means of generating fetal-specific PCR products is to identify loci that are unmethylated in fetal DNA and methylated in adult/maternal DNA. Another means to detect fetal-specific DNA is to identify loci that are methylated in fetal DNA and unmethylated in adult/maternal DNA. Loci of this type are differentially reactive with bisulfite such that unmethylated Cs in DNA undergo oxidative deamination, resulting in C to U transitions. Methylated Cs are not reactive with bisulfite, and consequently, are unaffected. Bisulfite treatment of fetal and maternal DNA present in maternal serum will create primary sequence differences between fetal and maternal loci that exhibit differential methylation. However, restriction enzymes that differentially recognize and clear unmethylated DNA can also be used. In other embodiments, the method for selective enrichment of fetal DNA requires the use of the methyl-CpG binding domain of human MBD2 protein, which is coupled to paramagnetic beads, for example DYNABEADS® M-280 Streptavidin, via a biotin linker. Without being bound by theory, the high affinity of the MBD-biotin protein for CpG-methylated DNA provides greater sensitivity than antibody binding, while the use of the DYNABEADS® provides a simplified, streamlined workflow.

In one embodiment, the DNA is amplified using quantitative PCR and primers selected to amplify sequences on a potentially abnormal chromosome. Control quantitative PCR with a second pre-selected primer is conducted on a normal or control chromosome (i.e., a chromosome not having the suspected anomaly) and the ratio of the quantity of the two PCR products are determined, thereby detecting fetal aneuploidies. If the loci of interest are from chromosome 13, 18 or 21, and quantitative PCR strategies are employed. In some embodiments, real-time PCR is utilized and chromosome copy number are determined. If the loci are also highly polymorphic such that both alleles can be discerned, chromosome aneuploidy can be readily revealed. Other amplification methods can also be used, such as Loop Mediated Isothermal Amplification (LAMP).

In some embodiments, methods are provided for detecting fetal chromosome aneuploidies by treating DNA isolated from maternal serum with bisulfite or restriction enzymes and then performing quantitative PCR on the sample with a primer pair homologous to a test chromosome sequence that is differentially methylated in maternal DNA and in fetal DNA, where the primer pair only primes bisulfite treated unmethylated DNA or restriction enzyme treated unmethylated DNA. A "control" quantitative PCR is conducted with a primer pair homologous to a control chromosome sequence that is differentially methylated in maternal DNA and in fetal DNA, where the primer pair only primes bisulfate treated unmethylated DNA or restriction enzyme treated unmethylated DNA. The ratio of the quantity of PCR product produced for the test chromosome is compared with the control chromosome, thereby detecting fetal aneuploidies.

In some examples, the mother and the fetus are human. However, the methods can be used in other mammals, such as, but not limited to, non-human primates. In some examples, the subject is human and the fetus is between about 10 and about 14 weeks of age, such as between about 11 and about 13 weeks of age. Thus, the fetus can be 10-14 weeks of age, 11-13 weeks of age, or 10, 11, 12, 13 or 14 weeks of age. However, the fetus can be of any age. In some examples, the mother is in the first or second trimester of pregnancy.

The methods disclosed herein can utilize the following nucleic acid sequences, or a CpG containing nucleic acid sequence within 100 kilobases (kb), 50 kb, 25 kb, 10 kb, 5 kb or 1 kb of these sequences.

In some embodiments, the methods disclosed herein utilize at least 15, at least 20, at least 30, at least 40, at least 50 or at least 60 nucleotides or all nucleotides of at least one of the following nucleic acid sequences:

SEQ ID NO: 1
ACAATATGGAAAACACAGCTGTAACCCATACACATTCACACCAGCACAAG

CTTCTTCCATCCTTCCTGGAGAGAGACAAAAACAGAAGACACAGAAAGGA

AGGGCAGGATCAGGGACAGCAGGTTCGTGGGAGGGACTGTTCGTGGGGGA

ACCCGGCAGGGGAAGAAAGACAGGAAGGGGAAGAAGGGGAAAGAGAG

GAAGTGGGGTAGGGCAGAGGGCCCTGGGCTGTGCACTCCCATCTCACACT

TGTCCCCAGAGCAAGGTCTTTAAGGCCAGACTCCAACCCAGGAGCAGGGA

GGGGGGCAAACGCCCCTGTAGCCGCCCTGCACCCTCCCAGGAGGGGAGC

ACAGGCTGTC

SEQ ID NO: 2
CCACAACCTGTCAGAAATGCCCCCAAGCCCAAAGGCGTCGAGAGAATGGC

CAGGTTGTTTCAGATTGACACATATCCTAATGTACAAGTCAGCCCACACA

CCCCACGTGCACTGAGCGTCTCTTGTTGTTCACCCCAAATAAACTCTG

CGGAACTGGGGCGGGACTCGCAGGGGCGGAGAAGGGGGGAGACGGGC

AGAGGGCAGAAGTGGATGGTGAGAAGAGCCAATGGAGGGGCCCCGTGAG

AGTGAGCAAGGCTGCACCCCT

SEQ ID NO: 3
TGATAACACTGGGGAGAGTTAACTTTTTCACCTCTGTTTGTTGATATGC

CCCTTTGTGCTCCGTATTCACAAAGGGGCACCTCAACAAGCCCATCATT

TGTTAATGAATGCCTTTACTTTCATCGCCAGCAAGACATTTTCATAAAC

CCACCATCTACTTTGCAGTTCTCAAGAGTTGCTTCTCTTAAACTGGTGA

GGACGCGGCTAAGCCCTGGAAATGAGTCCAGATTCTCACGGTGGCCCAT

AAACACTGCTGTTTCCTCCCACCTAGGAAACCCGCAGACCTGCAGAACC

TGGCTCCCGGAACAAACCCTCCTTTCATGACTTTTGATGGTGAAGTCAA

GACGGATGTGAATAAGATCGAGGAGTTCTTAGAGGAGAAATTAGCTCCC

CCGAGGTAGGCCTCAGAAAACCAGTGTTCATAACTTGATTGTCACTTTC

CCCCACTAGTAGTCAGTTCTAAAGCTCTGGGCAGTGTGTGTGTGTGTGG

TTTTCTGCAGCCCACGGTGCTCACTTCCTTAATCATAACCCTGGTGTAA

CCAGATTAGAGTTCGGGGACCTGGGTTTCATTGTGCTGCACCTGCAGCT

TGGCAATCACAGT

SEQ ID NO: 68
CCTTTGTTCTTGTTGGCATCTGTGTAAGAGAATCCAGGGCCTGAACCAT

TGTCCACTCAAACAGACCATACACACCTGGTCCAGTTTTGTGCATGCCT

CCCTTTTCCACAGTGTGCCACTTGCTATAGTTCTGAACAAAAACTCCCT

TGCCCTTCGGAGCTTTATTTATTTTTAATTTGCTCTGTCATTGCATTGC

ATGCAATAGAAGCTTCCTGGTGGAAGCTCAATGTTCTGCTCAGTCCCAG

ACACGTTTTCAGCCACTGTATCATTGCCTTAGGTTGTGGTTTCCCCAAA

GCAGCACCGGAGGTAAGGGCTTGTGTGCAGGAGTTCACTTGGGAGGTGG

CTCTAGGAAATAGAAGCGAGTTTCCAGGAAGTGTGGGATGAATACGGGG

ATGGGGTGGGGGCGGGGAGGAATCCAATATGAATATATAATCTCATAT

TGAGTATAAAAATCCAATATGAGTATGTTTTCCAGACTGCTGCTAAGGA

GAATGGTGAATTATTCTACTGCGACCTTTTGAGGGTCCACACAATGCCT

CCCAAAACTATCTACCAGAGGGTGGATAGGAAGCATTGATCCATGGCTT

ATATTCCCCATTG

SEQ ID NO: 4
ATCAGAGTCGCCCTTGACCTCAACCCTGCCCGAGAAGGAAGTGCTGGTG
CAACCCCAGCCCAGCTGCAGGAAGTGGTACCTGTCACCAAGTCCCTGC
ACAGGGGAAGCAGGGGGCTGAGGGGGCAGGACCAGGGGGACGAGGTCAT
CCTTCCCCGGAGAACCCCTCAGGGGCCGGGCGCCCTTCCCTCCCGGGCA
CCAAATGGACACAGCTAACAAGAACCACACTTCACGGTGAGCAAAGCTC
TGAACATTCAGGCTCTGAGACACGAAAGCGGCGTCAGAAGAGACCTGCA
GCAGATCCGGGCCAAATCACACACACCCTTTCACAGAAGTCGAGGACAG
GAGAACAGGAGCAAACACAGGAAAGGAAGAGGCCAGCCTGGTGGCTGAC
GCCTGCAATCCCAGTGTTTTGAGAGGCCAAGGCAGGAGAATCACTTGAG
GCCAGGAGTTTGAGAGCAGCCTGGGCAACACAGTGAGACTCCTACCTCT
ACAAAAAATAAAAATAGAAAATAAATTAGCCAGACATGGTGGCATGCAT
CTCTAGTCCCAGTTACTCAGGAGGCTGAGGCAGGAGGATCACTCGCGCC
CAGGAGGGAGAGA

SEQ ID NO: 5
CTCTGAGATGCGTCGTGTAGTAAACTTCTCAATAAGGCGTAGTTTATGT
TCAAGAGAGAAATTCTCTTTGTCACTTAGCATAAACCTTGTAGCTAGCT
TTCTGAATATTTGTATCTCAGTAGAAGAGTTAAATGCCTCATTCAAGTA
TGTTTTCAAAATAAAAATTGTAAATAAAATCACGTGATGTTTATATATG
AGAAGTCACCAGCTTTTCATTCAGAGTTCCCCCGTTTCTAGAGGTTGGA
CCAGCCTCAATGATCGTGGGGAACCTGGTTGCTGGGAAGAGAATCGCTC
AGGCTTCCGGGAGAGAGCTCGCCCACCTGGAGGACAGCGACCAGGCACG
GAAGGTGACAGGCCAGTTCCGGGACGGGTGGACGGGTGTCTGTGCCCC
GGAGGCGCCAGTGAGCAAGTCGCCCTCTCGTGCAGTTCCTGTTCCTGGC
TGACGTGCTGCAGTGGCGTGCCCACACCACTCCTGACCACCCGCTGTTC
TTGCTGCTGAACGCCAAGGTGAGGCAGTGTCACGCCCACGGGGCTTGGA
AACACCTGTGGGCCGGTGGAGCCCTTTGCTTGTCTAGTTCATGGTGCCA
GTGTCCTGGTTGT

SEQ ID NO: 6
AAAATCTTTTTTTTTTTTTTTTTTTGAGATGGAGTCTCGCTTTTGT
TGCCCAGGCTGGAGCGAAGTCTCTTAGTTTCCTCCCCACGGTTTCGTGC
ACTAGACCCCGAAGCAGGCAAGCTGAGCATCTTTATCCCCATTTTTCAG
AGGAATGACTAGAAGTCAGGGTTTGCCCAAGGTCAAACAACTAGCTGGT
TGCAAAGTAAGAATTGGAAGCCACCCATGTTATTCCTTCCGCTACACCT
CCCTCCAGAGACAGGGCTGGCCAGCATCGCACGGAACAGGAAATTGAAA
TGGCTCCCGGTAAGGCAGCGAGCCTGCCAACCACCGAGAGAAGCTGACA
AGTGACCCAAACCCGCCCAGAATTTAAAATGCCTCCTCAGAGGAGTTGC
CGACTAACCTCCTCCCACCTGCTGCAGTGAAGAAATAAGTTCCAAGAGT
CTGCAACCCACCATGCCTGTTTTTCCACGGGAAGGACCAAGTTAGAAAG
GAAGCTTGAATAAGTGGGATGCTGTTGAAGAACTAAGATGTAGAAGCAG
TTTCCCAATATGAACTTACTAGCTTTTTTCCCACTCCTATCACATCGCC
ACTCCCCCCACAC

SEQ ID NO: 7
GCTCCTTTTTGGGTAAGGTCTGTTGCTTCTCTAGGAACAGTGACGGTGG
CAGAGCCCGTGGCCCCTCTCTCCTGTCCCAGAGCCAAGCTGTTTCCTCT
CCCCACTCCCGGGCACCCTGCGGGCAAGTGAGGGGGGCCCACTCTGCCC
TGGCCTGCCCCACCGCCCCATTTGCTGGGTTGTCCTCAAAGCACACGGT
AAGCACCCCCGCCCCCGCCCCCCACACACGTACCGCTGTCAGCCTTCTT
GCTCGTCACCTCCATCCAGGGCACATCCGCCCCTCTGGGTGCTGTGAGC
CTGTTGCCGGCGCGGTCCCGCTGCTCCTCCTTCTGCTGCCCTGCACTGC
CGTGGCACAACCCTCCCTCCGGGTCTCTGCTGAGCCCTCCAGGCGCTCA
GGTCTGCCGTCTGGTTGCAGGTGTTTTATAGAGTGCAGCTTTACGCTCC
CACTCCAGTCATCTCCACGTTGGTGTCCGTCTGTGTGTCCTCTCTGCCT
TTAAGTTCTGCCTCTGTGTGACACAGTTTCACAGTTTCTGTGACCAAAA
CACAGGTTTAGTCGCTTGCTGCTGGCAGAGTCCAATTAACAAGAGCACG
TCGGGTATAAAGA

SEQ ID NO: 66
CAGAGACGAGAGACACTTTCTTTGTACATGTCCCACAAGCACAGTTCCA
GGATTTTGGCACTAAGTAAACAAATAAAAATATGCAACAGACATAAGAG
ATAATAGTAATGTGTATTGAGAAATATAATTTTATATAGTTGTTCCTTT
TTCCCAAGATTCTTTATTAATATCACCAATAGTTATTACTAGAAAACAC
TTTCAGAGCTAGAAAGTTGCCAGAAACATTTCTAATTGACTACTGTTAT
AATTAATATTTTGAAATGCTGAGACATTTGCTAGGGTGGACAGCTCCTT
CAAAACCCGGCCGTTATCTGACGAAAGAGCCTAGGCTCAAATAAGAATT
AAACACAAGTTGGAAGTAAGGTGAGGCACAGTGGAATTTTTTTAGGATG
GATATAGTTTTCAATAACCTTAATTTGGAATTTTTCCTTTGGGATAATG
ACTTTGAGTCTATAGAAATATTGTATGCATTATAGACGAATTGATTTTT
TAACTAAATTCTGAAAGGCTTAAGTAAAATGATTTGATGATCAAGTCAG
ATGCATTTCTAAGGAAGTGAGGATCACATTAGACAGAAAGTTTGGGTTT
GGTGTATAATAAT

SEQ ID NO: 83
CAAATTCTTCCCAAGTACTGTTTCCTTTCCTCAATTCCTGGCCTAGCAA
GTCTAGAAAGAAAACAAAAAGAATGTAAAATGTTCTTGGTTGACTTTAC
TCTTAATTACTAAAAAGCAAACAGAGAAAATTAAAATCAAACACATGCA
AAAAATTCTTCTAGAGCCTTGCACACAATGCCAGTTCTTGAAATATTTC
ATAAAGCAAAGCTAATGAAATAAACAAAGACGTGGCTGAAAGGATATGC
ATTGTACTGTGCTTATGGAGCCACATTGCTCACTGCATCTCTCGCTCCA
CTGCCGCCGGGCTCATCTGCCAGAAGCCTGTTCCTGAGCTGATTGGGGT
TCTGGTCCAGGGGTCCCAAGGAGCGAGGCCCAAGCTCAGGAGGACAAAG
AACGACCACCTGGAAAGTGGCAAAAATCTGTAAAAAAATAAAATCTGAG
TGGGCCCAAGGGGCACCTGGTCTCAAGAGCAAACGCTGTGTCCAGAGCC
TCATGTCCGGAGGCCCAGCCCGACTCCCTGGCTCTTACAGCCCCGAAGC
CCAGAGACCACCCCAGCCCGACTCCCTGGCTGAGACTTCCCGCCCGGAT
GCCGTGAGATCGT

SEQ ID NO: 8
ATGTGAGAACCCAGCACCAAAACTGGGCTCACGGATCAACAAAAATAAC

CCGGGCCTCACCGACCAAAATCAAGTAGAATAGCGGTTGGGTCAAAGGA

GAGAAAAATAGGCTTGGTTGCTAACC

In some embodiments, the methods utilize one or more of SEQ ID 1-7, 66, 68 or 83. In additional embodiments, the methods utilize all of SEQ ID NO: 1-7, 66, 68 and 83.

These nucleic acid sequences can be used to purify fetal DNA and/or detect aneupolidy of chromosome 21 (SEQ ID NOs: 1-7, 66, 68 and 83) or chromosome 18 (SEQ ID NO: 8). In some embodiments, the methods disclosed herein utilize at least 15, at least 20, at least 30, at least 40, at least 50 or at least 60 nucleotides of these nucleic acid sequences.

The following nucleic acid sequences are less methylated in fetal DNA than maternal DNA, and can be used to detect fetal aneuploidy of chromosome 13. In some embodiments, the methods disclosed herein utilize at least 15, at least 20, at least 30, at least 40, at least 50 or at least 60 nucleotides or all nucleotides of at least one of the following nucleic acid sequences:

SEQ ID NO: 9
TAAATATCTGTGAGAAATATTTGTGAAAGTATATTATGGAAAAAATGGA

ATATGCATGTAAACTTAGGCTATGTTGAGTAAAATAAAACTAATGTTTT

AAATATGAAGAAATGAACAGTTGCTCAATGCTTGTTTCTCTACACATGT

GCAGGAAGTATATAATTCAGTGCTGTACACATATCACATTGGAGCATTA

ATCACAGCCGTGTCCCACTTTACCCAAACATGGCCACATAGTCTCTTAA

TCCAAGCATTTGGGAAACTACTAGCAATCATTTAGAGTGGAAACATAAT

TTGACACCGGTTTAGCATTCCATTTGTTTGCTACATCCCTCTTTATGAC

AAGAAAGGGAAAAATCATGTAATACTATAATTTGAGGAAATGTAATAAT

GCATTCAGGGAGACAGAAGCAGGAAAATTTTGCCTGTGTAGAATATTGT

CACACATACATGTATGTGTATGTGTATGTATATCAGAAAACATATTT

CAAAAATAAAAAGCTATGCTTAGTATACCCCATTGCAAAATCACTTCA

TAATGAAAGCACAGACCATGTACAACAAATAAGTGTGACAGAAATGAGT

TTGGCAACTACCC

SEQ ID NO: 10
ATTTACAACAGCAATAGGTAGCAATAGGTCTCATGACTTTACTTCTCTA

ATGGATTGAAGAAAAACCAGTGAATTTTAATTTGTCCTGCCTTTGCTTT

TTGTGAAATGAGAACAACTTACAAGCCCTTCAGATATTAGAGCTAATAC

TAGAAATCCTCTGGTGAGGTTTTATTACTTATGTTATATTTTACAATC

ACAAATTCTCTATTTGCCTCTTTTAAAAAAATGTTTTCTAGGTGGGAGT

CGGTGGCTCAGGTAAGAGATACTGCCTCATGTAACTCTCTGGGTATGAC

TTTCTCCCGGATTTAAGGGTAGCAATAGGTCTCATGACTTCAGTTCTCT

AATGGATTGAAGAAAAACCAGTGAATTTTAAATTGTCCTGCCTTTACTT

TTTGTGAAACGAGAACAACTTACAAGCCCTTCAGATGTTGGAGCTAAAA

CTAGAAATCCTCTGGTGAGATTTTTATTACTTCAGTTATATTTTACAAT

CACAAATTCTCTATTTGCCTCTTTTAAAAAAATATTTTCTAGGTGGGAGT

GGTGGCTCATGCCTGTAATCCCAGCACTTTGGGAGGCCGAGGCGTGCGG

ATCACCTGCCTGA

SEQ ID NO: 11
TTCTATTCCTTTCCTTATAAATCCAAGCAATAGTTTCATTCTTTAAAAA

TGCATAATGTGAAAATAGCATTAGGAAAGCTGCCTTGAAATATGGATAC

TAAATGCATCCCACTGGGCAACTTCAGCAAACCGCTGGGTCTTCCACCA

CAGTTAAAATAGCTCCTGCTGTCCCCGGGGCAGGAGTGGCTTAAGAAAG

CATTTAATCCAGGAGTGCGTGTCTGGAGCTTTGTGTTAATCAGATTCCA

TATGACTGAATGACCTTTGTTTTCCCTCTGGTGGAATCGTGAACATTTG

GGAAAACCGGTTTGCTTTTAGTGAGTGTTGCAGGGTGCAAATGAAACTG

TATTCAACCTAGGATTCGACTGGGAGAAAAACAGGAGAAAGGCCACAGG

ATTGGTGCAAGGACAGCAGGTCAGTGTCAGGGGCTAGGTGACTGGGGAG

AAAGCTTGCTGTCCCCTCTGAGTGTCCTCCCCCAAACCTCAGCGTCCCC

CCTTGGGAACCCATACCATGGCCCCGGGCAACAGAGGCAGCAACACAAA

TAAATAGAAGAACTGTTTCATTAAAACCTCCTCCAGACAAGGCCAGCTC

TGGATGCAGTCTT

SEQ ID NO: 12
GATGGTGAACTGTGTTCTGGCGGACTTATTTTTAATATACCAATTGTGT

GTAGCACAATAGTCATTTCATAAAAGGTCTTCAATGTGTTGTAATCACT

GAATGGGAAATAAATTTCCATCCTCTTTTGAAGGGTGCATTTGTGATGT

TATACTTGCTGCATATTGTGGTAACAAGCAGTCATTCCCAAAAATGAAC

ATGACCCTATTTCATAACAGGATATTGATTTTGCATGCTTAAATTAAGT

TTGTATTTATTATTACTATATATCTCTCCAGTTAGTTTCCATTTTTACT

TCTAATCCGGTTAAAAACTTACTATATTTTAAAAATACTCTCTGCTATA

GCCATCTAATTATTTAAAATAGAATCTCAGGTTATTAGGCAGTGCATTG

CTTCCTACATCCAAATTTGAGCTTGAACATTTTGCTAACTCTTTTGGAA

TTCAATTTCCAGTTTACTCACCTCTGAAGAAGTATGGATTACTTGACTT

GTTCACTAACTTTAGTAGAATTAGAACTCACACTCATGTGTCCTAACAT

CAAATTTTCATTGAAGATCATGTGCTGCATGACCTATACAGATGGTCCC

CAACTTGAGATGG

SEQ ID NO: 13
TTTGCAAAGAATTCTCTAAGAAAGACATTTTCCTGCTTTCGTTTCTGTT

TCATGCTGGGTAATGTTGGCAAGAATTATTCATGGCACATGTGAGCAAT

TCAAAGAAATATTGTAAAAAAAAAAAAAAAACAAGGCAGCTTTGCAGA

GGTGCGCTATCTGCTTGATGACTTGGCATGCTGCCTCTGGTGCTTGGCA

TAGCACCCTAGCTGCTGGCACAGGGGAAGTTACATATACTTGCCATTGG

GCCTCTACTATGCTACCTGCTGTGCACGATCAATATCAACCAACTGCAT

AAACAACCGGATGAACCTTGTATCTGAGGGACAGCAAATAGCATTTGAA

TTATTTTACATAAATCTGAAAATGTAATAGCGGTTGATGTTCCTATTAG

TATTATATCTGAGCACGATGATCATAATTGAGTAACATTAAATTTAGTT

TATTGAACAGCAGTCCACTGCCCGGTTTACTGTGACTACGATCTGTGTA

ATGAAACCAGCAATATGAAAAATTCTCTCAGTTGGTACACTTCCTGGAG

-continued
AGGAGCCAAAGTATTTATTGCTATTTGTGCAATTAATGGCCGTATCGAT

TTCTTTTTTTCT

SEQ ID NO: 14
TTACCAGGACCTCACTATAGGAAGAAAAAAAAAGTAAAGCAACCTCGCA

GGTATCTTTGCTGGTTAACATCATAGAGTATGAAGGGTATCTTGATGTG

ATCCATTTTAAGCTACAAAGTTTCTTACAGTCATACTCAAAACTGGCAA

AATACAGGACATCATACACATTTTCATATTTTATTCTAATGTTTATTCT

GAGGTCAACAATATAAATTAGTTTCTGAGATGCGCAGATAAATTAAAAT

TCCATGCAGGTGACCATAGACATACCCCTACTATGTGTATCTGTCTAAA

CTATAACCGGAGAGGACTACAATTAATCCCTTAAGCCCTTTATCTTCTT

TTCGTCTCCTGCTTGGTTCTACGTAAACACCTTTGCTGAACTGGAAGAT

CCAACCAACTTATACGAGCTTCTTGGATGCGAATGAAAACCTCGTGAAT

TGCCCAGCAAGTTGACATTCCTTTCTAGATCCAGCACATACAACTCTCT

CCAGGTGAGCACAAAGAAGAAGAGATTTGAAGTCAGCGAGGTGCGTTT

TATTGGTTCAAAAGGGGAGGTTATTTTTTAAAGGCTTATGGAAAAAGGT

AGCTATGTTTGTT

SEQ ID NO: 15
TTTGTTAGAAAGTGGCTGTGATCACAAATCAAAAAATACTAACTCATGT

ACAAGTGAAGGACCACTGGCCACTTTGGAGGTCTCTTGATCACTCTTGG

ATTCCCATCAACCTTAAATAGGATACCAGTCAGTCCCCTGCTGCCTATC

CTCAAGAATTCTTTCACTTTGAAGGATGTATAACACCCATAACAACTTA

TGAGGCAAACATGTTATACATGAAGGCAACTTTTCCAATATATCACCTC

CCCCCATACAACTTAACACATCTGAACTTTCATGGGATTCAAAATACAA

AAAAGTCCGGATTCTTTCATATGCACGCAGATCCAATAATAACAAATAA

TTAATGATTCTGAGTGTTATTTTATGAGGATGGCATTTTATATCCCTCA

TGCTTAGGGCAATTCTAGAAGGAGATATTATCACCATTTCACTGTTGAA

ACTGACTCAGAAGCTTATCCAAGAGCACAAATCAACATTAAGTAACAGA

GCTGGGATTTAAACGCTGCTGAGAAATCCGAGAGGCTCTGTATTTTTA

AAAACAACTTTTAGAGTAACCTTTTCTTTTCAGCCATGTTAATTATAGG

AAGAGACTACAAT

SEQ ID NO: 16
CGAGAGTCTGGCTTCCAGTGAAGAACACTTGACAAGGGAGAAAATCTGG

ACATTTCTGCCTTTGAGTTTTGCTTAGGCCAATCTTGCAATTCTCCCTC

AATCCACGTGGTCACCATCTTCCCACCTAAAGAGCACTCACCTCCTTTG

AGAAGCCTGTGCTTGTCCTGACCCCTCTGAGCACACTTTAAAGTTTATG

AATTCATTCCTTCCTTTGCCATTTCCAGAAGGTCTTTGTATTTTGCACA

AGGACTCTAGTTCTTTGTGCTGGCATCAATTAGAGACTGTTTGTTTTCT

GTTTTCCCGGGTTAATGGTAAATGTTTAAGGGTAAAGATCTTATCTTT

ACATAGCATTGATTTTTGAACATTTGATTACTTGCTTATTTATTAAGCC

TTTGCTCATTTGCCTTACCATAATCTTTTCTATACCTTCATGTTTGAAT

TGTTTTTATGGCTTAAGTATATACATATAATATGTATACATAATTATAT

AAAATATGTATATTCTCTTTTATACACTATGAAAACAATTCTTGGAAGC

-continued
ACATAAAATGTCTTTGCACAATAAAGAAATATTTTAATATTGATAATTC

ATAAATTATATTG

SEQ ID NO: 17
TGCTCACTTTTTCCTTAATGGAGATTTTGTTCCATGTATGGTAGGTAAT

GATCTGAGGCAGGAAGACAAAGAGCAGATAGCATTCAGGGCCTCAAAAG

ATTCCCCTAATGTGTACAAACATACTAGATCTGAAGTTCTGGTTCACCA

TGGTTCTTCCTCATTAAGCCGCAGATTTCCACTTGGAAAATTCATTGGT

AAAGTGCCATGCCTGCTTGCTGCTGATAGGATTTTCTTATTGTCCAGCA

GTATGCAAGTATTCAGCCCTCAGTCTCTCAGAAGAGGGGTCTGAATTCC

CTTGTTCCGGGGTTGTGACCTTAACCTTGTCCTGAGATTTATAGCCCCA

GAGAGGCTCTCCTCCTGATTTACATAGTTCCTGATGTCACTTTGAGCAG

ATTTAGTTCCAATCTCTGCAGAACTCTTGACTATGGAATGTGGGAACAC

GACGAGCTGTTTGTTTTATACTCCCAAATCCTTGAACAAAAGTTACAGA

GTGTTTTTCTATCTTCTCAGAGGAAGAAGGCCCCTCTCCCATTCCCATT

CAGTTCTACCAAGCAGCAGCTGTTGCTGTGTGTACTGTGTTTAAAATCC

CTTTGTTTTATGC

SEQ ID NO: 18
TTCTCTTTCTTAATGATAAAATTACCATAGTACCAAAGTAACTTAGCTT

TAGCCTTCTTCTAAAATAGGCATATTCAACCTCAGCAACTGGGCCAGAC

AAATTTTTGTTGAGGGAAATGTTCTTTGTGTTTTAGGATATTTAGAAGC

ACTTCTGGCCTCTGGCCAATAGCTGCCTAACACTCCTCTCCCTCTTTTC

TAGAGTTGCAATAAAAAAATATGTCTAGATGTTGTCAAATCTTTCTTGG

GGGGCAAAAGTGTCACCTCTTCAGAACTACCAGTTAGTAGATATGGTAA

AAAGAGCCGGGTTGCTTTTTAATTTTATTGCATATTGACAAATTATAAT

TGTATATAATTATGGGATACAAAGTGCAGGAGGCTGAATGAAATAGGAG

GGATCACCTGAGTCTGGGAGTTCGAGCTGCAGTGAGCTATGATCGCACA

GTGCACTCTAGCCTGGATGACAGAGTGAGACCCTGTCTCAAAAAAAAAA

AAAAAAGGATAAAAAAGGAATATGCGATAATTGCGTACCTGCGATAAT

ATGATGCAGGTACGCAATGTGGAATGATTAAATCAAGTTAATTAACATA

TCCATCATCCATC

In some embodiments, the methods disclosed herein utilize at least 15, at least 20, at least 30, at least 40, at least 50 or at least 60 nucleotides of these nucleic acid sequences.

In some embodiments, the methods utilize one or more of SEQ ID NO: 9-18. In additional embodiments, the methods utilize all of SEQ ID NO: 9-18 to detect an aneuploidy of chromosome 13.

The following nucleic acid sequences are less methylated in fetal DNA than maternal DNA, and can be used to detect fetal aneuploidy of chromosome 18, In some embodiments, the methods disclosed herein utilize at least 15, at least 20, at least 30, at least 40, at least 50 or at least 60 nucleotides or all nucleotides of at least one of the following nucleic acid sequences:

SEQ ID NO: 19
TGCTCACATCCCAATGTCTTAGTGACTTTAGGAAATAAAGCAGCTCTGT
AATTTTTTTTCTTACATCCTCGCTATTCAACACCATACTCAGTACATAA
ATCCAGATGGGATCCGGACAGTAAAATAAATCTGAATGACAGATAATGT
GCTGTCCTCAAAAATGACTCTCCTCCTTTTCAACTGAAAGAAGACATTT
GTTTATTTCAGTGAAAACGAGTTCATTATTATCTGTTCCTACTTCCTTG
GGAGTGATTATTCTGTCAGATACATGCTAAGTGCAAATTTTCTGCATAG
CAGAAACCGGGTCTTGAATCCAGGTGTTCTGATTCTGAGTTTATTTCTC
TAAACATTGGTAATGACCATAGAAAGTCTATTTTAAAAGGAAACACAAA
CCAAAGACTAATAAAACTATATGCAACTAGAGAGAATTGTATCATGATT
TAGATGAGCTCTGCTTTCTACCCTTCTCAATTTAAGTGGGGGTTCATGT
TATCCCTTACTTTCATTGTCATTTTCCTTGGTCCAGTGTTCTCCTAGGT
CTCCAAATGAAGCTATCACTTGCAGTCTGCAAAACACAACACTGCACTA
ATTTAATTCTGTT

SEQ ID NO: 20
AATGTTCCTTTTAGATTCCCTTCTTTCCTTTTCCTTCCTTCCTTCCTTC
CTTTTCCTCCCCTCCCTCCCTCCCTCCCTCCCTTCTTTCCATGTTGTTC
AGGTCACACTCTTCAGCTAGATTTGGGGGAGAAGTGGGCTCAGAAATGT
TGGGCATGTGTGGCAGCACCTAAAACGTTATGGAAGCAGGGTGAGTCCC
TGAGCATGAAGCAAAGGAGACATGTAAAGGAAGGAATATCCAGTTAGTA
TCTGAAGGTGGAACAAAATCATTTAGTTAGTTCTAGCCACACAATCTGG
TTTTACCCGGATTGAATAGTTATATGACTCAGGAATCAGAACCCAAACG
AATTAATAGGCAAGAAAATGGCATCCCAGAATCTGTGAAAACTCATAT
TGATTGAATTTTAAGAACAAAAAAGGACCTTAGACGTGTCAAAATCAAC
TATTCCAAGTCCCTCTGTGGTATTAATGACATCCTGTTAAAACAAAAAC
AAAAACAAAAACTTTCAGCAACATCACTTCAAAATTATCCTTTTTTATT
TTTGCATAATTTTAATTCATAGAATCTTTTATGAAAATATTTCTAAAAA
CTTTCTGCACTTA

SEQ ID NO: 21
TGACCTCATATGGCAGCAATCTGACTGGTGATTGCACTGAGAGACAATG
CACATGGCATAAGAACAGCTCCTTTACGCTCCTCTTGATGAAGAAGAAC
AGGTGGAATACTTCATATACTTTAGATATTGATGTCACTATAAGCAGCT
TTGACTTTGAGTTCAGAAAGCAATTGATGGGAATGCAGGCTTCTAGAAG
TATAGCTGTCACACAGATTTAGGGTCTGAAAGCAGTTTTCTGGTTTACC
TTTTGGCACACAAACCTTCTCTGGTAAGGGACTGAACTTAATTGGAGTC
TAAGATCCGGTAGAGAGAGCCATATTGATACTTATATGAATTCTAGAGT
TTTGGTGAAAAAAAATCAAAGGTAAGTAAGTGCAAAATAAATTGTTTTG
CAGGCATAAATATTCAAACATATAAATATATGTCAGGTATAAATATACA
TATTAATATGTGAATATATTATATATAAATATAGTCAGATATAAATATT
TAATCATCATAGATTTAGACCGAAGGAGGACAACATAAAGAACATTACT
CATTTCTTTGAGTTGCTGGGTATAGCTCAATGATGGTGGATCTTGGGTA
CCAGAAAAAAATG

SEQ ID NO: 22
TTTCACTAAACATTATGTTAAGTAATGTATGTAGGTTGATAGGTTTATA
TGGTACAGTAAGTCATTAATTTTAAACCTTCATATGAATTCAATCAAAT
CTTTCATGCTATCTCCTTAGACATTAGAATTATTTTAAATTTGTGTTTT
GTTCTGTTTTGTTACTACAAACATTGCTAGGATAAACATTTCGTGCATA
CGTGCAGACGTTTCTACACAGTTTATTTATGGTGGCCACAAAGTCTCTA
TATCCTAATTAGTGACCTCTGTGTTCTATTATTAGCACAAATGTATATT
TTCAAACCGGATCTTGTAGACAACTCCTTGGGAGTCATTAACAGGGAGG
GTACCTGATAGTTTTCTTCAGATCATTATTATAAGCAGGGATATCATGC
ATGGAGAATTTATAGCTGCTCTATAAGTGGAAGGGCATTGTTCCATTAT
TACTAAATATTGCCAAAGTGATCTTCACATAGGTTGCTTCTATGTATAT
CCCAACAAGAAATACACGGAAGTTCTCATTACTCCAGATTCTTGACAAG
AATTTATATTATCAGACTTTTAATTCTTTTACCAAATGAACAATAATGA
TTATATATCTTGT

SEQ ID NO: 23
TTTGCCAAAGAACTATGACTTTAGAATATGTGTTATTTACTCTTCCAAG
ATACAGCTGAATTGGAGGGGGATTGGGTTGTGCAGATGGCACTTTTTGC
ATGTCCCTTGCTCAGATAATTGGATTGTAGAAATAAAAGAAATAATCAG
GATGTCAAATTTTAACATTCCTTTTACTCATGGATACTTTGGTGTTGCT
CTTATTTCCATAGGCAGAGGGCAGATGATTTTCAGCCCCATAGAAATAG
CAGAATGTGCAGGCTACTAACTTCGCTTCCTTGAACTAACATTATGATA
TCATCACCGGATTCCTCAGCACAACAGCCTGTTCTTAACTCAGTTCCGA
ATGTTTTCTCTCACTATCATCTCGATCACTTCCAAATGTTTTCTCTCAC
TATCTTCTTGATCAGGCCATCCCATTCTTAGGTTCTTACTGTGCCTTCT
CACTTTGTCTTAAACAGATAAAGTCCTTCAGCTGATTACATTTCAAATG
CGTCACCAGGTTGGCCAGAACGCGTCGGTTTCTTCCTATCTTGTTTCTT
CCACTTTTTAAATAAAATAGATTTTTCTAGGAGGACACTATTTAACTT
TTCAGCACATATC

SEQ ID NO: 24
TTGCTGACGATTCACATTTTATTAGTTTGGTTATGTTTTGTCCTTTTAA
AACATTTTCTTTTGAGATGGGGTCTTGCTCTGTTGCCCACGCAGGAGT
GCAGTGGCATGCTCTCAGCTCACTGCAGCCCTGACTGCCTAGGCTCCAG
CAATCTTCTTACGTCAGCCTCCAGAGTAGCTGGGACCGCAGGCACTTGC
CACCACGCCCCACTAAAAATTTTTTAAATTGTTGCCTTTCTTGAAGTGT
TCTCTGCCTGTCTTTGTCACAAAATTTCATTTTTCTCATAGTTAATTTC
ATCTCTCCGGTAAGATTTTATTGGTGTTTCTTTTATAACTTTGCAGTTC
TTACACCGTTTGGTGATTTTCATGTTTCTTAGAAACTTTAAACCTTTAA
CTTCAAACATTAAAATACAAGTCTTTTAAGTACATGAGTGCTTAGAAAT
GTACATAATGTTTATATACACTTATGCCTTACATTAAAGTCCAATGA
GAAATACATGTTTAACATTCAATAATAATTTTAAAAATTTGAGAAATAA
ACTCTCATAAATGCACACATTTTTATAAACTTGCTACTTGTCTGCTGTT
GATTTTAACATTT

SEQ ID NO: 25
GCAGAAGCTTTTCCTCTCCTGCCCTGACGGCGAGTTTTCTCCATAACTT
GCTCCCGGGGTTCCCCTGCGGGTGTCCTCTCCCATCCAGACTGGCTGGC
CATTCCCGGGACTAGACGGTGCTTAGGGCGATCGGGAGCTCTGATCCGG
CCTGATTTTTCTGATCATCAGCTTCCTTTCTTTTTCATACTCTGATTCT
AAAGATAAAGATAGAGCCAGTTTCTCCCCCTTTGGTGTTTCAAATTCCT
TTCTCATGACTCTTCAGGCAGTACAGTGAAGAGATTAAGTGCACGACGT
GGAATTCCGGCCTGTCTCCTTAATAGCCTTACGATCTACCTCACGGAAG
TGTTATGAGGGTGGAATGAGTTAGTGCACATAAAGCCTGTAGCATGGTG
CTTGGCCCAGAATAGGCCCTCAGCGAATGTTAGTTATTATGGTGATGAT
TAATACTTCAGTTTCTCTGTGCTCAGCAAACACCACCTCCCTGTGTGGG
CACTGCATAATCCCCTCGCCACATATATTCAAGGTCCTACCCCTGTCTG
CTTATGCTATGGTCTCTAAGGAGGAGCAATGGGGGATGCCTGTCACCTT
CCAAGACTTTTAT

SEQ ID NO: 26
TTGTGTTATTAGTAGAGACGGGGTTTCACCATGTTGGCCAGGCCGGTCT
CGAACTCCTGACCTCAGGTGATCCACCCATCTTGGCCTCCCAAAGTGCT
AGGATTACAGGCATGAGCCACCATGCCCAGCCACATAGAAAGATTTTGA
TTAGATATTAGGAAGGATTTGGGCTACAACAAAAACTTGTTGAACGATT
AAGTCAAAGCATACTCCTTTGAATACTGAAAATGTTTGCTGAGGTTGTC
TCAGTTTTGAAGGACTGCTTTCCATTCCATTTTTCTTGTTATCTTCTGA
TCTAAACCGGTGATAAATTTTATGCTGTCCGATGACAGGCAGGAATGGT
AACAGAACTTGCAGATAATAGGTTGCTTACCAAAAGTTATAGATTGACC
AAATGAATTTGTTTTCTAAGAAAATGGAGGGCATTAATATAAAACTCAA
ATTCCTTGGAGTTACTCAAAGCCCTCAAGTATATTTGTCCTTGTCCATT
GCCATGGATGTTTCCAAAATGTAAGCTTTGATGAGAAGTGGTAAAGAAA
ATAAGGCATTCG

SEQ ID NO: 27
CCTTAGTTTTTTGCTGTAACCCAGCTCATGGCCAAGGCATCGTTGCATA
GATTTGAGACACTAGAAATCAAACCTGAACTGCCGGAAGTGCAGATGCC
GCAGCAGACCTCCTGGTCAGGCTTCAAATCCCACCTTCCACACCTGTTC
CTGGGAGATGAAGTTTGTACCCATGGTCATCTGTCCCTCTGCCACTCCA
TTCAGATGTGTCCACGTCTCCATGGCCCCTCCATCCAAGAGAAAGCAAC
ACACATGTGCAACCAGGAAACATACAAAAGTGCCTTGCAGCCTTGTGGA
TCCTTACCGGCCAGATAGCCATGGGCTGTGGAATGGAACATAAATATCA
CACAATGCAGTTTTCCTTGGCAGCAAAAATGAGCAAACAAATAACATAC
ATAATAAAATGAATAATTTCACAGGCACAATGAAGAGTGAACAAAACCA
GGCACAAATGAGAACACCCTGCGTGATTCTATTTATACAAAGTTCAAGA
ATACGCAAAATGAACCTGTTGTAATGGAAGGCAAAACAGTGTGATCTCC
CAATGAGATACCATCTCACACCAGTTAGAATGGCAATCATTAAAAAGTC
AGGAAACAACAGG

SEQ ID NO: 28
TTTTGCCTAGTTTTTCTGTAACCTGCATAGTTGTTTAAAGCTATAGATT
TTTAAAAAAATGTGTGCATTCAAGTTTGTTTAGAGTACAAATTAGAAAA
GAAGGGTGCTTTCCTTTCCCAGATAAAACCTTTGCGGATGTCTTGGGGG
TTGATACTGACCTCTAGTGAAACCAGTCTAGGTCAGTGCTGTAGCTGGA
AATTTAAAATCCCACTCAATTGATTGGAATCAGTGCTAAGAGTAAATTA
AGCTAATAACAACTCTCTTTCAATACAGGGAAAAGAAACAGAAAATTCT
GGACATCCGGAAAAATGTTAAAGATGCTATCGTGGTAAGGACTTTTTTA
AATGATTGTTTACTAGAAAGGTCAAGTGCTCTTCATTCTAAAACTGTGT
AGACAGAAATTACATATTGTAGATTATCATACATGGAGCCTAAATGTTT
ATCCATATTTTTTTTCTTATTCCATTTTAGACAATTGTTTCAGCAATGA
GTACTATAATACCTCCAGTTCCGCTGGCCAACCCTGAAAACCAATTTCG
ATCAGACTACATCAAGAGCATAGCCCCTATCACTGACTTTGAATATTCC
CAGGTAAGAAATGAAACAACAGACATGAGACTCTTGAGTGGCAGGAAAT
TTTCCATCTCACTT

In some embodiments, the methods disclosed herein utilize at least 15, at least 20, at least 30, at least 40, at least 50 or at least 60 nucleotides of these nucleic acid sequences.

In some embodiments, the methods utilize one or more of SEQ ID NO: 19-28. In additional embodiments, the methods utilize all of SEQ ID NO: 19-28 to detect an aneuploidy of chromosome 18.

The following nucleic acid sequences are less methylated in fetal DNA than maternal DNA, and can be used to detect fetal aneuploidy of chromosome 21. In some embodiments, the methods disclosed herein utilize at least 15, at least 20, at least 30, at least 40, at least 50 or at least 60 nucleotides or all nucleotides of at least one of the following nucleic acid sequences:

SEQ ID NO: 29
AACCATAAAAGGGGCAGAGATAGACTCTGTGGGTTGTCTTTGGAATATC
CCAAGGGATTTGCTCCTCTCTGATCATGTAGGTCTGCGGCTCCAAGGGC
AGTCCGTCACCACCCTATCTGGAGCACTCTTCTATCCTCCTCCCATCTC
TGTCCTCTGGCGATGACCACAGCCCCGGGCACTGCTAGTTGTGCCCCTT
GCTAAGCTCCCATATTTTGTGTTAAGGAGCAAGGATTTTCACAGGCTCA
TAGAGCATTTGCTTCCTTTCTAGGGTAATTAAGACTACACTAGAAACCA
TCTTGTCCGGTTCTCTTTTACAGATGTTGACATTAGGGCCCCAAGAAGA
TACGTAGCCTGCTGGTGTCACTTAGGGAATTAATTCCTGAGCAGGTGTC
TGGTGCCTGGGGCCCTGCTCAGACCCCATTCTCTCCTCTGGTTCTCGAT
GGCCCTCACCTCCCATTTCTTTCCATTTCCCAGAGGAGTCTGGTTGAAC
TTATGGCTTTTTTGCCTTGATTAATTGACTATGAATTTATGTCCCCTA
AAAAGGATTAAGTTGCATCATTTCTTCTTAGCATGCAGTGCTCAGAGA
CAACCCAGCAATT

SEQ ID NO: 30
GATAAAGAAAGTAATTTTATAAGAGAGGAAATAAAATGTAATGCTTTTT
CCAGCATAAGGTGAATGAGATCATCTGGGTTAGGAAGTTTTTCTATGCT
GGGAAGATATGATAAAGTAATTGAACATAAGTGCCTAGAATTTTATAGG
AAACTTCCAAAGTCACTTGATTTAGAAGGACAGATGAGGCTCAATATGG
CTTCTTCCCTCAGAAGTGGCATAGGTTACAGCAGTAGAAACTTAATCCA
GCCTCAGAAAGAGTTCCCAAAGCACTCAAAAGTTGTATGCAAAAGACTT
AGAAAAcCGGGCTGGAAATATTTTATACAGTAACCCTGAATGCTTTAGG
ATGGTTACTTTTTAATGTATTCCATGCTTGTCTAACACCTGCCCATTCC
AGGGGGTACATACGCAGGGGCCTCTCCAGGCGAGCATCTCAGTTATACT
TCCATCAGGTCCTGGCAGGAACACTGGATAGGGAGGCTAGATTCACTGC
ACATCGCCTCTACCATAGCTGCTCAGACCTTCATGTGCACACAAAACAC
CCAGAGATCTTGTTGGAACACAAATTGCCAGGGTACAACCCAGGGGAAT
TTGCATTTCTCAC

SEQ ID NO: 31
AAAAATTTTAAAAAGAAAAGTATGATGATGATAAAATGAACCACTAAAA
CTAAGAACAATAAGTGAAAAAAAATCACTTTTTTCTGAGTGGGAGAAAC
AAAGGTATAGAGACGGTCTTGCTAAAGGAAAATTGTAAATTTAAGTAGC
AATAAAGAACGTGGCATAATTTTCTCCAGCAGTATTCAGTGGCAGAGGA
AAAATATATGCATGCAAGTAGTTTGGTTGATTGAATCTGTGGACAGAAA
AAAATAAAAAGAAAACCAATTGATGAATTGTGGGAAACTATTTCAAGC
AATGGCcCGGGTCTTCTGGAGGTATTAGGGAATATTACAGCATGAAATG
ACATATCTTAATAAAGAAGTTTAGAGAGAATAAGAAAACAGTATAGTCG
AATATTGTTATAGTAACTACAATAATTAACTACAACAATTCATCATTAT
ATTCAAAGACAGAGACCAAAAGATCATATTGAAACCAACCCAATAGTCT
CATGGACAGTTGTTTTTGGATAAACATAGAAATTGCCCCTTTCTGGTCT
TAAAACTTGAAGCCGGCCAGGCGCGGTGGCTCACGCCTGTAATCCCAGC
ACTTTGGGAGGCC

SEQ ID NO: 32
TGGATTTAAAAAATATATATATCACGAGCCGAAGTATGAACCACGAGAG
ATTATCTCCACCCCCTGACTAAAATCTCCATTAATTAAACATGAATGCA
AAAGTAGCCTCTGCCTACAATTCATGTGTGCCATAAAGATGAATAAATA
ATCCTTACTGAGTGCTTTGAATCTCTGAAAAGAGAGCGAGCATACAATT
GTTAGACATCTTTACACCTGCCCTCATGTTATCTAATAAGCCCATTATG
GGAGTTTAATACAAAAATATATAACAAAATTGTAGAACGTAGAAATATA
TAAAATcCGGGATGAGCCAGAATTTACCTTGTAACTAGAATTACTTCAT
TTATAATCTATAATGCTACAGATGTATATTCTCAATAGTATCAAATAGG
TTTATTTTTTCCAACCCTTGGATTTCTTCTTGCATCTTCACCATCTCTA
AGCAAAGTGATTCCATAGCTAAAAGGCAGAAATGTGAATTCTTCTTCAA
ACTTGTTAATACATGTTGAACAAGATGCTGATAAACCCAATCTCTAAAA
ATATGAAATATCTGATATTTTGTAACTATAAAAAATCTTAAAAAGGGAA
ACAAATCCAAACT

SEQ ID NO: 33
ACTAGAAAGGAAAGAAACTGCCCTTCCTTTAAGGAATGTGGAATCTTTC
CTTTTGAAGATCAAGATTTGGAGCCCATAATCCTGTGGATGGATGACGC
CAACATTCAGCTCTGCTGCTTATTCCCCATAATTTCTCCGCTTGACCTG
TGACGAATCAGCTTCTGCCTTTCCAGGGACTTAGAACCTTTCTTATGGG
ACTCCTCTCACTCTGAATGATGGTGATTAATTACCAGTGTACTTTAAAA
GTCTCCTCTATTTAATTACATCCTCCTGAGTATTTGGACTAATTCCTCT
TAGTTTcCGGTGCAGATCGGAATGTTGCCTTGAGCAAGTCTCATGTTTC
TTTCTCCCGCTTACGCAGTCAAGCACATACATAGATACGTAATAAATAT
TGATTAAGGTTCTGTATTAGGCTGTGTTTTTATCAGTAAGGATTAATAG
GCATAAATGAGAGACATGATCCCTACCCTGGAGCCTAAATGGCATGTGT
TATAAAGACGCTTTCAGGCTGACCAGTTCTTCTAGTGCAGCTGAGAAGA
CAGCCATGCCTCCTCATTAGCCCACTTTATAGGGAAGAAATGGAGACTC
AAAGTATCTAAAT

SEQ ID NO: 34
TTTTAGCATCATCTGGTGAGGCTAAGGATTTTCAGAATCATCAGATACT
GGTTCTTTTTTGTTCGATGTTCTTCCCTCAATTTATCTCTTTCCTCTCC
CGCTTCACTATAAATAACATGAAGAAACCAGGTGATACACTTAACACTT
TGTTTGGAAATAGCCTTAGCTATGTGACCAACATCATCGCTTACAAGTC
CTGCTCTCCATGGACAATTTCATTAAACTCTCTGGCACACATGGGAAGG
ATCCTCCTTGCTCCGATTTCCTGGAACACCTGTCACATTCCTTTCTGAG
TTCTCCcCGGAGGATTCACCTTTAGCATCCCTATTTCCTCTAGCAGTCT
GTTCATGGTGATTTGGGCTTTCTCTGCTGTGCTACTCAAAAGTCTCTTA
GCCTCTACTCGCTGCCAAGTCCCAAAGTTGTTTCCACATTTTAAGTTCA
GAAGGTTTCCAACTTACAATGGTTTGGCTTAGGATTTCATAATGTTACG
AAAGTGATATGGGTTCAATAGAAACTGTACTTCAAGTGCCCATACAATC
ATTCTGTGCTACATTTTCAGTACAACATTCAACGAATTACATGAGATAC
TCAACACTTGATT

SEQ ID NO: 35
AATAAAATAGAAGGAACTTTGATATATGAATCAATATGGATAATCCTTA
CTCTTATCGAAATCCTTACTCTGAGTCAAAAAATCCAGGCAAGAATGCA
TACACAGTATATCCCATTTATATAAGTTTTTTAAAATGCAAAATACTTG
GATGAAAGGTGGTCAGTAACTAAGTTGTTGCCTGAAGATGGGCATAGAG
GGAGCCTTGGATTAAGCAAGACAGTAGGACACTTTGGGTGGTAATGAAA
ATGTCGGTTTTCTTGATTATAATGATGGCTTCAAGCACAGATACAGATA
TTAAAAcCGGTAAATTTTTCAAATATGTGCAGTTTATTTTAATTAAATT
ATTCATCAATAGAGTTTAAGACACAAACAACTGGATTCCACCAGAAAAC
TAAATATATTACCTTGTTAAATTGATGCCTAAGTGAAGCATAGTGCCTC
ATAGCAGAAAGGGTTAAATTTATTTCATTAATCCTCTGTTTTGAAAAAG
TGATCACTAGATAAGTTTGTTCAAAAAGAGACAAAAATAATAACAAAAA
CAACTAGGCTTTGACTGAAAATCCAGTGCCTTAAAAAACTGTAGAGAATT
TCTACACTGTTTC

-continued

SEQ ID NO: 36
ACACCAGCATGGCACATGCATACATATATAACTAACCTACACATTGTGC
ACATGTACCCTAAAACTTAAAGTATAATAATAATAAAAAAAGAATGCT
TGCTTACAAATTGTGTTTCTTTAGCACTTAATGTTGTTTTGTGTTTTTC
AAAAAAACAGCATCCAAATATACTGGTTGACAATTTGTTTCCAGTTTTT
TTCTATAAATGACAAATAGGATATTTAATTTTTGTCTAGCGTAGAGAAG
AAACATTATAATTTTGACAAAAATATGGTTTCACCTTTCATATAAAATT
CTAAAC<u>CC</u>GGTAGCACACTTACCTGAAAGGTGAGAAATATGACATTGCC
CCAGTAAGTGACAACATCTGTGGTGCTATCACAAGGCTAAATTCCTTTA
TTGTGTCTTTTATAAGATACTGTTAAGTCTAGCAAAATACCATTTTGAG
ATGCTACTTAAACGTGGCTCAGAATAAATAAAAAATTGTCAAAGAAACG
TTTTAAATTAACACTTCTGATTTTAAAATATAAAGCAATCAAAGACAGT
GGTTTTCCAACGTGAACACACCGGGTATCAGAGGAGTATTATTGAGGCA
ATGTAAAGAGTAT

SEQ ID NO: 37
AGGCAAGTAGGCGTTGGATGGCAATCCTCTCCCATGTAACCGTGCTACC
CCATGGTATGTCAATAATGAAAACAAGTTATATAACAGATTAAGATTGT
CTAAAATGTATTAACAAGAAGCAAAAATAGTCACATCAACTGCTCTTGT
AAGCTTAGAATACTAAGGCTGTTCAGACATTCTGAAAGCAGGATAAGCC
AACCTTCTAGTTTGGGTCAAGCAACATTGTCATCTCTGAAATGAAAGTG
TGTGGCCAAATGGAGATGTGAACCTACCATGCTGCTCCAGAGATATTAG
TTTCTG<u>CC</u>GGATTTGCATATCTTTACATCGAGTTCATACATGGGTGTTG
GTGCCTGTACACTCATTCTATCCAGTCATGTAACTCAAGCACAGCTCAT
TTTACTAATGTTTGTATGCTAATTAAAAACTCTTAGGTATAGATTCCTA
TAATAATATTTAAAGTTATTATGTAGCTACTTCTGAAGTGTGAATACCT
GAGTAGGGTACTTCAGATGTTCAATACTCCCTTAGAACAGTGAATATAG
TAAGCACTCAAATGTTACTTACTACTTTTCTTGTACTTATCTTGGTTGT
CATCTTCATTAGT

SEQ ID NO: 38
GCCTCATCAAAGCATTGTAAGAACTGATAACCATCTTCTAGAAGTATCA
TAGTGATATTAAGAACACACATCACAGATCATAGTAAATGGCTTTAATT
TTTTAGCGAAATCTCACTACTGCAAATGCATTGTTGTCCTAGCTAATGA
ATGCATAGAGTATTGCCTGCAAAATAATAATTGAGATTCTATTTTTAAG
AAGCTTAGAACAGTACATGGTGCATAGCAAAGACTCTGTGTATGTGAAG
CCAGATTTTAAAATATGGTAACAAGTGTCTGAAAATATGTGGCTCAATT
TGTCTC<u>C</u>CGGTTACTTTTCCCTCTCCCCCTTTAAAATGTAGAGGAAGGA
GAAGAAGAGATAAGAGGTTTGTGAGTGAAGACAAGGGCCCTTTAAGGCC
TGGGAAGACTAACGCCATAGGGATCTCCCTCTGCCTTAAAAGGCACAGG
AATCTTAGTGGGAAAAAGAAGTGGTGATAAATAGCCAGTCCGTGTGCC
TGGAATATCAAAGTCAGTGCGTGCCAGGGATCACACTGCGGGTCACGTG
CACTCTGGGTCTCTCTCTGCAAACCTGCCCTGCCTCAGTCTGGGAATAT
GCAACTGCCTAAG

In some embodiments, the methods disclosed herein utilize at least 15, at least 20, at least 30, at least 40, at least 50 or at least 60 nucleotides of these nucleic acid sequences.

The following nucleic acid sequences are more methylated in fetal DNA than maternal DNA, and can be used to detect fetal aneuploidy of chromosome 13. In some embodiments, the methods disclosed herein utilize at least 15, at least 20, at least 30, at least 40, at least 50 or at least 60 nucleotides or all nucleotides of at least one of the following nucleic acid sequences:

SEQ ID NO: 39
ACCCACCTGGTCGCATCCTGCGTTCACCAGTTCCTGCAGCATTTGCCGG
TTCACTTCTGCAGCTGCAGAGGTGCCCGATTCATTAGCAAAAGGCAACA
AGGAATATCTGATTTCCCTCAAGGCTTTCTGATAAGGTCCGAACTTTGG
GGTGGCTCTCATCTGCTGCTGCTGCCTGGTGGCATCTTTGCTCCCCAGG
ACTTTGGCATCCAGGGAAGTGTCACTGTTTGGTCCTGCGGGTAGCCCCT
GAACCGAAGACTTGGATGGCTGTTTTAACCCCTCACGAATCTCTTGCAG
TCGCTG<u>C</u>CGGCTATTTCCAGAATAAGTCGTGGCAGGAAAAGTCTTTGGC
CTCATTGTTAGTCCAGTTTCCTTTTACCATAAATACAATCTTCTTAAAG
TGTTTTATTATTTAAAAAAAAAAAACTGTCAATAGTATCAGTTTGTTGTA
AACATACTTTCAAAATAATTTCCTTTTGAAAATGTTCTTTCCTTCCATT
TTTGTAGTTCCTATAGAGAACCTAAAATTTTCCAAAGTCTTCATTTTGA
AGATTATCACTCTCTGAAAAAGAAAATAAATGGGAGAGAAATGTTCATT
TGTCATTTTCACG

SEQ ID NO: 40
GGGTGCCCGTAGTCGCCGCTGACCTTCTCGTAGTGAGGGCAGAAGACGC
TGTCCGCAGTCCTTAGCGGGATGATAATGTCACTGGGCTCTGAGCCGTT
GTTGTTGCCGCTGCGCTTGGGTGTGGCCAGTGTGCTGAGCGACAGCGTG
GTCGTGTGCTGCGGCGAGTGCTTCCTGTGTCTCCTCCGGTACTTCAGCA
AGAGGACCACCAGCGTGATGATGATGACGATGAAGATGATGCATCCTGA
AGCAATCCCTGCAAATAAGGCCACTTCGGAACCGAGGATGTTGTTCCCC
GAATGT<u>C</u>CGGCGCTGTTGCCGTCTGTGCTAGAACCTGCAGACGCGGAGA
CAGAAAAGGTCAGAGATAGTTACTGCTGTCCCAGTGCAGACGGACTGCT
TTTATGACCCTTAAAAATGTGAAAAATAAGCCAGGCTTATTACTAACTA
GAAGCTGGACTTTGCCTCGCCAATACCTCGTCTAAGAGCTCAACGCAAA
AGGAAATGAGAGGTATCTCTAGGAGGGACTTCCCTACCCTCCCAAGCCA
CAGGGTTTCCTTTGTATCATTATCCAGCAAGAGCACAGACTGTCGGTGA
CAGCCAGCCCTTG

SEQ ID NO: 41
TTTTTTACGTAATGCTCAAATAGACCTGGGAGATAAGCACTGCTATGAA
TCCCCAATCCCCATGTTACAGACAAAGAAATTAGGGCCAACGAGTGGTA
CAACTGGATTAAAACCTAGGCTTCTGGCCCCAGAGCCGCACACTAAACT
GCTGTGCTTGAGCGCTATAAAATAACCACATTTATTTATGTATTTTCTC
TAGTGATACTTATTTGCAATTTTCCATATCATGAACAAATTTCAGTGAA
CTTCCTTATGCCTACCTCTTGTGTGTATGTGGACATTTCCTGGGGATAT

ATACCT<u>C</u>CGGTGGCATACCTGTGAAATCCTTTGCTTATTTTTTGAGAGA
ACAGAGCAGAGCAGATGCTAAAATTGCCTTTTTTCCTTGAGAATTTTTT
TTCTCTGATAGAATACATGTTCCATGAAGGCAGGGATTTTTGTCTCCTT
TGTCCACTGCTCCATTCTGAGCATCTAGAAGAATGCCAGGCACATGGGA
GATGCTCAGTAAATATCTGTGAATGTATTAATGGCTCCTGAATACGACG
CTCTTTTAGCCTAATTATGCGAACTCTTTTTTTTTGTTCCCCGCCCCA
CCCCCCTCCAGAC

SEQ ID NO: 42
ATATAAATCTTCTTTAATAAAACAATTCTGTGGGACAGATCTGCTACCA
AGGCTCAGAGAAGTTGAGTGGCCTGACCACAGTCACACAGCTGATAGGT
AGCAGGATTGGGACTAGAGCCTGGGGCTCCTGCGCCCCAGGTCAGTTAC
TAGGCATGAATAGAAACACCGCACTGCAACACTGAATGTTAGCCGACAT
GGCAGCTAAAATGCACACATTAGCATTACCAAATGAGTGAGCCGATTGA
GCAAGTGAGTTCTCCTACCACTACCTCCCCTTAGCATTGGCTTTGAAGA
CGGTAA<u>CC</u>GGGAAAACTCAGACTGGGTCGCCCCATGTTATTGCGCCAGG
ACTGGAGACTCTGAGAAGCTGGTTGCAACATTTGGCGTCTTCGCTTCGG
ATGCTCTATAAGCCTTTTGAGAGATGAGCCTGAGTTTGTGGCGGCAGGC
TCCCTTTTGAAAGAGCCACCCAATCTGGCCTCCCCAGACATCTTCCTGG
AGGAGGATTGAGCATTATTCCAAAAAGAAGGGTGGCCTCGAGCTGGCC
CATCAGGCCCTAGCAATACCCAGCTCCTCATCAGGATGGGTGCAATGTT
TGTTTTGGACTTT

SEQ ID NO: 43
ATATATTGCCACCTGAAGAGTTGGCTTTCAGAGCTCTTTGGAATTTGGA
ATTGTAGATGGAGGGTCATGGATGTGTACCAAAAATGTTCTTAACAGCC
AAGAAGTCCACAGACTAGGCATTGTGCAACAGTCAAAAGCAACTCTAGA
CAGCTCCCCAGACCAGCACAGTGCTGCTTGTTCATCCTTGCTCCTAGGA
AGCAGGAAGTACGTGATATCAGCTCTCTTGGAAATAACTGTCCCTTTAA
GGAGTAATTGTCTTGAGTAACCCCTAAGGAAGTATTAAGTATTAAAATT
CTAGGG<u>C</u>CGGATTCACCATCCCCTAAGGATTCTGCATTTCTCTCTGAAA
ATCTTAAGTTCAGAATAACCAACCAGTTCCTTCTAAACATCAACAACCT
TATGTTAAGTTCTCTGACCCTTCCCTGGTAATTCGTAAGTTTATAAAAT
CTCTCCCCTTAACTTAAGCCTTAGTTTCCCAGATGCCATCACTTTGAAA
ATCTGCCTCAGAAACATCAGTACCTCCTAATGGGATGTGATAGAACACC
CGAAAAACTGCTGAATGGTGTGGTGCTTCCCCAGAGCCCAGGGGACAGT
GTCTGGGGTCCCA

SEQ ID NO: 44
GCAGATGGTATGCCAGGGACAATATACAAGACAGAATAGAGTTCATTCA
AGTATTCTATGTTTTGTTATTTAGTTTTCAAATATGAACCCTGGATGGA
ACCAGGCTTTGTTCCCCAAGTTATCAGCTAAAGAGAAAGAGCTCAGCC
AAGTGACAAGGTGTTGCCGCAGTGATAACTCAATTTTGTGGTTTTCAGA
AATGCAGAAGAAAGAAGGTTGGAAAGAATGGGCTGGCACTCCCCGAAGA
GTGGGGCTCAAAGTTCTGGTCTCAGCAGATCTTTGAGGGAGACGTAGGG

TCTAGG<u>C</u>CGGCAAAACCAGAGAGAAGGATAGGCTTTTAGATGCTCATCC
CACCCAAAACCATGAAATAATCTCCCCTGTCTCCTGATTAGTATTTGTC
AGCCTCATTTACCCTTAAGATTTGTGCAAATGAAAAACGTTAAATGCAG
TTCCTGGATCAGTAATTAAACATAATTATTTCAGTGGAAGAGATTTTTG
TTTTCATAATCTCCTCTTTGTCTGCATAGAGCCAGCTCTTGGTTACATC
TGCCACTGATAGCCTTTGCTCTGTTTACTTTAAAGAATAAGCCACTGTT
TGATTTGGTTTCT

SEQ ID NO: 45
TATTCGCATGTGTTTTGTGAATCATTCTGTCGAACAAGATAGAAAAG
AAGGGCCAGTTCCTAGGTTGCACTGCGTGTCTGTGTGATGGAATGACCC
CTGTAACTCCTTAGGCCTTGATGCTTCCTGTGTTGTGTGGGATACACAG
AATCCACTTGCCTTCCTCCCAGGGCTGCAGAGATGAAAAACTATGACAC
ACATTACAATGCTCTGTAAACTATGTTTATTCTACAAATGTGCATTATG
TTATGAAAGTGGAGTAACTAATAACTCCACACTTCTGCCCTCAGAAAAC
TTCCAA<u>CC</u>GGATCATCTACCTCTTTTTGAACGTGCCCAGCAATGGAAGG
TTCCTGCACGGCCTCATGTGTTGTTGCATAACCCTCAACATTAGGAAAG
GGTTATTTTTATCCACTCAAACTTTCATATGTTCCAGTTTAAGTAATTT
ACCCTTTCGCTGTGCTCAGAGGGGACAGGGACTGAGGACACGTGGCCAG
ATCTAATTGCTTCCTCCCCTTCCAGGATGAAGGATCAAAATTCTTTAACC
TTTCTCAATTTCCAGTGTTTTAGGCCTATTTTTACTTGATATATTCCTT
CTTCAAGGGACAG

SEQ ID NO: 46
AAGAAGCTGGAAGCTGATTTAGTAACTTTATTGTAGTTTGCTTGGAAGG
TAAATGTATTATTGTATCCTTCTGTTCACTTAAACTGCTGACCTAGAGT
AGGTTTGAATAACACTTTGTTTAGTTTGGCCACAAAATGCCTGTGAAAG
GGGAAATTCTTTGGGCAGCCAGGGCAATATCACTTCCTTATCTCCCAGT
ACCCAAACACCTTTAGTTTCTCCTTCCTTCCTTCCAGTTGCTTTCAAAA
AGTGGCGATGAACTGCTTGTATAGTTGCCATTTAGTATCCAAGGGGGAT
TGATTC<u>C</u>CGGACGCCCACAGATAGCAAAATTCCTGGGTGCTCAAGTCCC
TGATATAGAATGACATAGTATTTGCATAGATCTTATACACATCCTCCTG
TATACTTTAAATTATCTCTAGATTACTTATAATACCTAATGCAGTATAA
GTGCTTTGTGAATAGTTGTTATAATGTATTTTTAATTTGTATTACTTCT
CATTTGTTGTATTGTCATTTTTTTCCCCTGAATATTTCCTACCCATGGT
TGGTCGAATCCTTGAATACAGAACCCAGGGATACAGAAGGCTGACTATG
TGACATTTCTTCC

SEQ ID NO: 47
AGAGCTTACCAGTGTTATTTTCCTTATTACTTCTGAGTCTGGCATGCTA
GTTTGGTTAGTGATATATTATTATTTAGGCCAAAGTCAGATATTTTATA
ACTACAGAAGCCAGTTAGTTACCTTCCCTTTGTTTCACAACCGAATACT
ATACTATGCACCTATGGTCCCATCTAAAAGATATTACTGGTCATAAGAA
TGTGGCTGTCTCCGAAAAAATTGTCACTACTAGAAAAACAACTGAAAGA
ACATAGTGTAATTAGAACAATATGGCCAAACACGTTTCGTTAATACTGT

-continued

GTGTTTCCGGAGGAAAGGGAAATTAGCAAATATTTTCCTCCTTTTCAAC

ATGGCTATGTTCCTAAGCAAGATAGCCTTATCCTGCTGAGGAGACAGAG

GATGTGGCATAAGACATACAGAAATTGACAAACATATTAACCTTGTATA

ACTAGGACTTTTTTACAAGGTATATTTCCCTTGTAAAACTAGGACTTTA

ATTTTGAGAATAGGATGGGACAGAGTCAAGTGAAAGAAGCCTTAGGTAT

CACATGGCACCAAGGAAAAACATCAAAGATTTCTGTCTGCTGCCTTTTC

CACATAGTCCTTT

SEQ ID NO: 48
CAGTAAAGAGACCAGCCACAGATAAGTAATTGGCAACCAGCAAGGTAAT

AAATCTAGTGTGGGGGACTGGCTGACGTTTGGTCAATGTCTCCTTCCGA

AGCTCCACCCAAATTTCTCCTTTTTGCTTCTCAGTCACAGTATTTCCCT

CCTGTTAAATAGCATTAGTCTGGGGAATAAATGCTCTTCCCTGTCTACT

ACACTGTGGGAAACGTCAGCCACAGCCTCCAGTTTGTTAGGTCAAAAAC

CTTGAAGTCATCCTCTCTTCCTGTCGTAGCCACGTTGATCCATTCACCA

GAAAATCCGGCTGGGCCTACCCAAATATGTAGAGAGCCCAGCACGTTTT

TACCTCTTCCGTCGCCATTGCCTTGGACCAATGCCTCTCACCTGGACTA

TAGGAAGGTCCTCCAGATGGCAGCCCTGACTCTTTCCTGCCCCTCTCCA

GCCGCACTCAGCCTCACAGTATCGATGATGATTTTCTTCACAGTCAAGG

AACAGAGCTCCTGGGCTGGAACCTCACACCCAGGAATCAGGGTCTGAGC

TGAGGTCCTGACAGTCACCTACAGGATTCTGAGCCTTACCCCATTGCAC

TAACCTTTCGAAA

In some embodiments, the methods disclosed herein utilize at least 15, at least 20, at least 30, at least 40, at least 50 or at least 60 nucleotides of these nucleic acid sequences.

The following nucleic acid sequences are more methylated in fetal DNA than maternal DNA, and can be used to detect fetal aneuploidy of chromosome 18:

SEQ ID NO: 49
TGTATAGATGCAGAGTTTTACTACTGAAAGGAGGAATACTACTGTTGAT

TTGTTTTTGTTTCTCGGTTGTTGTGCGTGTGTTTTGTTGTTGTTGTTGT

TGTTTTACCATCTTGGTCCTAAGTAGCTCGTTTGCCGGCCCAGCCTTAA

TGGCCAGTTGGCTCCAAGTCAGAAGACATGATCTCCTCCCCCATTCTCC

ATGCCATTGTTTAAAGCCCCTCCTGAGGAATGGGCTGCCTTGGTGTTTT

GTCAGTTCAAACCACATCCTGCCTGTTTCCACTTTCCATAAGACAACTC

GCAACACCGGTGGTTTTCAGATGTGGCCGGCTTCTTGGTGAAGCGATAG

CAGAGGCCTTGTTCACAGAAGTGAAAATAATTCACCCAGTGGTTAGCAC

ATCAGGTGTGGGCATTGAGTGTACCCCGCTCCCTGCTTGATCCCAATCC

CTGGTTGGGTTTGGGAGTGGACGGCTGCCCAACCTCCTGGCACTGTCTT

GACCCACAGCCTTCTCTGGGATGAGGACTAAGCCAGAAGCAGTAAGGAC

AGAGGTGTCTCAGGCTGTCCAGGCCTGGCCTGAATCCCATGACAGCAAG

GGTGTGGCCTGCA

SEQ ID NO: 50
GCTGAGGGATTTGGTCATATCATTAGCCCAGACATAGCCTGACAAGACC

AGCCCTTGTGTAATGAGATTGGTTTGAGGTAGGAACTGTACTTGCTTTC

TATGATGGGCAAGAGGAGACCCCAGGCTCTGGATGGGAAGCTGAAGGCT

GACCAAGGGTGGATGAGGCAGAGGGCCTGCGAAGGGGACTCCACAGAGG

CCACACGCAGGACAAGAGCAGCACTCTACTCCAGGCTTCATCCATCGTA

TGGAGGTCTGTGGTCATTTCACCCATTCATCTTGCTCCTCTGGAGAACC

CAAACCCCGGAAACCACAAAGGGAATCGACTGCTGCTTCACAGGAAGGG

TTTCATTCATGATCACATTTCTTTACTGAAAAAGATGGGTATATTGAAG

CGTTGACTGCCTCCTCAAGAAGAAACAGGAAGTGATCATTACCAAACAG

AGGCTCCCTTTAAATTTAAAATATGTAGCCAAGAAAGAGGCTAACACTA

CCTAAGAAAGACCCCAATTAAATGTTTAAGCTAAAAAAAGCAGAGGGTT

GGGGATAGGGCATGTTTTTGTTTTGTCTTCCAATTTCAGTGTTTTTAAA

GGCTGAGCACCAA

SEQ ID NO: 51
GATTTTTGCAGAGTTATTTTTAAGCAGTACAAAGTAGAAACACACTTCT

TGAAACAAAAATGCTTTGTCATTTCTTAATCTCTACCTTTAAAAATAGC

AAGCAGCTATTTCACTCTGAGGAGCGCTTACACAGCCATCACTGCCCGC

AACCCTGGGACCTGAGGGGGAGATGGGTGAGTCTGGAGAAAAGGCTGTT

TCCTAAGAGTCTCGTTGCTAGTCCTGCTCGGTCACATGACCTCACCTGT

GGTCCCGAGCGATAGTGGGCAGCACGCAGTTTTATTACATGAGGCAGTA

TGTCTCCCGGTTCACGCTTATTATAGCAATAATTCCAGAGCTTCTCACT

CTTGGTTAAAACAGAACAGAAACACAAATGCAATACCAAGCACAAAACC

ACGAACATCTTTGAGTAACTGGGCTCTTCCTCCTACACAAAACGTCCTG

ACGGGTCCCTCAGAGTGAATCTATGGTCACGACCCGGACCCCGGAGGCC

TGTGCATTGAGTATGCGCTAAGGTTTTTAATACAACTGGCTTCTTTCCA

TTGTCTCCCAAATATCCCACCCCAGGTAGTTGGGTACTGAACACAAACT

GGTCATTTTGATA

SEQ ID NO: 52
CATGGTGAGACCCCATCTCTACTAAAAATACAAAAAATTAGCCAGGCAT

GGTGGCGGGCACCTGTAGTCCCAGCTACTTGGGAGGCTGAGGCAGGAGA

ATGGCGTGAACCCGGGAGGTGGAGCTTGCAGTGAGCCAAGATCACGCCA

CTGCACTCCAGCCTGGGCAACGGAGTGAGACTCTGTCTCAAAAAAAAAA

AAAAGGGGAAGTCACCAAGAAAGGGATAGAGGTCAGTGACATGGTCATC

ACACAACTCGGTCATTTAATATGGCAAAACACAATACCAAGAACTGTGC

ATTAGCCCGGAAGGCAAGAGGGTTGGTTCTGCCCCAGCTCTGCTGCTAA

TGAGCCCCTACCAGGTTGAGCAAGTCTTTCCCCACTCTCCACCTCCATT

TCTTAATCAGTTTCATGACAGGGAAGGATTTGAAAGTCCTTTCCACCTC

AGAAGTGTTGATTATTCTCTCTCCTATAATCTGATGAAATCAGCATG

ACAACAAGTAATTTAAGTAAAGGACAGAAGGGTTACCCAAGAAGAGGCA

GGAAAATGTTAACGTTCTATAAAGTTTTATTCTTGAGTCATAGGAAAAT

GCTCTCCAGACGT

SEQ ID NO: 53
CTTGTGTTACAGATGGAAGATAAGATTGGAGAGGAGGAAGAGTTAGTTT
TGAGTCTCTGACAACAGGGCTGCCACTGCCAGATTGCATCAAACCGTTT
TAGGTTTTGTCTTCTGGGAAGCACCATTGCATCATAGTCAAACACGAGG
GCCAGGAAGCCCAAGAAGTGTGGGTTTCAATTCCATCTCCACTTATCAG
CCACACTTTTGTGCCTCAGTTTTCTTATACACAAGATAAGGCTGGTAAT
CTGGCCAAACTTTCAGGATAAGAATTATAGACATTTAAGAAACCCAGGA
AACTGTCCGGCACATAGGAAGCATTGATATTACTGAGTGATAGCACTGA
GCCAGTAAAACCTAGACAGAAGTTGGAAGATAGGGCACAGTGTTCTTGT
ATCTTCTGAGCAGATGGGTAAAGAAATTGGATAAGAATTCAACGTGGTG
GCTGTTGAAAGTCATCACTGGGTCTTCTTGGTCCAGCCATTCCCTTTGG
TCTCTGTCTTTGGCCTGGACCACCATCTTACCTCCATCATTCTTGAAGG
ACACACCTGAAGCCTCACCATTGCAGCAGGCTTATCATCAGGAATTAAT
AAGGTGCAGGGAA

SEQ ID NO: 54
AAAAAACTGCTATAATTCAACCAGTTCTGACACAAATGGTGGGTTTCAG
AGAACGGAGTAGAGATGAGAGAAGTGGCTTTTAGCAAGAAATTACGCAG
GTGACTTTCAAATAAATCATCTACATAGAAGGCACGTTTTGCCTCTAAT
GTGCAAATAATTTAGCATCTGAAATGGCATGTAAAGATCTCATTTTAGA
TTCAATTCCACTCTAATTCATCAAAATGGGAAGTAAGGCATTGTGGCAT
AACAATTGGGATCAGAAGACCTGTGGTTACATCTCAGTTCAGCCCACAG
AACTAACCGGGACTGAGGCCATTGGTCTTAGACCTCTCATCTGTGGGAT
GGGGTTACTAAGACTGATTTCCTATGTTTCTTTGCAAAACTTGAAATAA
TTGTGTGAAGAGTACTTTGCAAAGAGATAAGTGCTACAGAACTATAAAG
TACTAAATAAAAGCTAATATATTAGGCATCTAATAGGTATTAATAGCAG
CAAGGTCTGACCACAAGCAAACACCTATTTTAGGCACTGACTTCTGCCA
AAAATCCGGAGCTAGATGGAGGAAGGAAAGGCTCATAAATCAGTCTCCT
TAAGAGGCCTCCT

SEQ ID NO: 55
CAGCTGGGGCAGGAAAACAACGGTGCTGCCTATTCTTGGACCCCAACT
GTTTCTAATTTGAGTCACTCTTCAGCACTCCGTTAAACCCCAGTCCCCA
TCCTCAGTTCCCAGGTGGGTTTGCATAAGGGGTAGTAGACCTGCCAGGA
GATGCAGTGAGAAGCACTGAGCACTGAGGCAGGAGGAGCACAGACAGCA
CAGAGAATCCTCTAAAGTGAAGTTTCTCTCTTTCTCACTGTTGTTGGGG
ACTCACCCTGCACCACAAAGAAGACTAGATAAAGAAAACCACTAACCAG
TAACATCCGGCTCAGTAGGCTGAGCACAAAAGCAAGGTTTTGCTTTGGC
CCTAGACCTAGAAGCCTGCTGAGTGAGCGCCTTGGCCCTAGAAAAGAGG
AGCAGGGGTTGTCCGGAGCCCCTCCGACCACGCTGCTCTCAGTCAGGC
ACCACAGACACAGGCAGAGCTGGCTAGAGGTCAGAGGCATGGCCCCAGT
GAGAAGCAGCAGCTGTGCCCTGTGAGCAGGTAGGATGGGGTTAAGGGCT
GGCCTGGAATGGGGCAGAAGGTGGAAGTTGGGAAATGGTGATGACAGC
AGTTATTGCAAGG

SEQ ID NO: 56
TGGCTTATTTTTAACTCACTTAATATTTTTCTCTTGAGAAATGTTAAGC
TAATTTTTTTTTTTTAAAGGGAAGCAAAAAGGCCTGTACTACTGTCAA
GGCAGACTGAACTTATTTTATTGACTGTGTTTTTCGTTATGGAGGACTG
TGTGTGACAGTACTTCTTTTACTTACAAAGAATTCTTTGTCACAAAAGC
CTCATTCATCCACTGACATTTTGGGGTTCCTTTTTCTGTAAACAATCAA
TCTAAAAGGAAGTGCCTAATCGGGTGTTTATGTTACAGGTGTAGCCTG
GCTGGGCCGGGGGTAGTTGGCTTCCTTCTGTTTTTCCTATGCTCTCGGG
AACATTTGACCTTTAGTTCCTTTCTAAATGCCTCAGTTCATTAGAAATG
TTTTGTGCTCATTCAATAAGTCATTTATTTGAGGTCAGATTTATATTTT
GAAAAGGTCATTTTGGCAAGTTATTTGGTCTTCCCAAAGTCCAGAGTGT
CCAGTATAAAATAGGGATATCATTCCTATCTGTTTCCTATAATTGTTGT
GAGGATGAATGTGTTAATGTAAGTGAAATGCTTGGTAAACAAGAAGGA
GATATATGTATTA

SEQ ID NO: 57
GATGTAAAAATGGGATCCTTGATTTTTAGTATCTGTTTTGCCGTCCAGC
TGTGCTTGCTTTTTAGGCCCTAAAAACTGTATGTTTTCTTGGCCCTGTT
ACTTAAAAGGCTCTACCCTGAAGCCAGTAATCCAATTAACTTACTTCTT
TAAGGAAATGTTTATATGTAAGGGTGTCTGCTTTTCCTCTCCATCTCAC
CTGAACTTTCACTCACGCCATTTTTCCTTTGTTTGCATAAAATATAAAT
TCTATATCTTGTTTCACTTAAGTTTGTCTCTTCAGAAATGCAGATTTAG
AGTTGCCCGGCTAGGAACTGTTTATGGCAGGAAGCAGGTATTCAAGAGA
CTGTTGGTCTAAAATGGGAAGAGAAGCTTAAAACTAGCAATTGAAAAA
TCTTTTGTCTGTCTGTGTAGGTTGTGTGTGTGATGTTTCCCTACTGAAA
TATATAAAGGTGCTCTAATTAATTGGCTTTAAAAAAAATAAGCACTTACA
TAAAATATTTTGTCAGAAAAATAGAAACTAAAATGCCTTTTAGCTCAAG
TGACTTTAATAATCTTTAGTAAATAAAAATAGTTTTACAATTATTGACA
AAAGTCTTTAAAA

SEQ ID NO: 58
GACATAGTGATAGGTTAGACTGTCTATTGTGAGATTCACAAAGGGGTTT
GGAACAGAAATCTAGACCAAGACCTTTTACACAAGAGATTCTTTGTGGA
ATACTTGCTGGAATATTCCCAGAGTATTTTGGGATACCCCAGACTCATA
CAAGGTTGTATAACCTCTAACTAACAAGATTCTAAGCAAAGGATGAGAC
GTGATCATGCTCAGGTAACGAAAACTTAGGGTCAATTCATGTTCTAATT
AGTTCTCTTGATCTAACAGTTACGGCTTATAAATCATTCCATGTCGGAA
GCCCCACCGGAAATAGTTGAGGTTCAATTCAGTTACAGCTCAATGAAGT
CTGAAAACAAGTGTCCAACATTTTCTGGTTCATGGTTTAAAATAGGTTT
CAAATAAACAATGAGGAAGCCAGTTTCCTGTTTGGGTTGGGTCCATTGG
ATCCTAGCCCATCAAAGCTTTGAATTATATTACAATGACAGGCAAGGAC
TAGAGGGGAAGAACTGAAACGCAGAGAAAAGTTGGCACAGTGCCAGGA
AACCTGGCTAAAATTAAGTCCCTCAGTCCAAAGAAAACAATGGCAGCTA
GGACATGAGTCAA

In some embodiments, the methods disclosed herein utilize at least 15, at least 20, at least 30, at least 40, at least 50 or at least 60 nucleotides of these nucleic acid sequences.

The following nucleic acid sequences are more methylated in fetal DNA than maternal DNA, and can be used to detect fetal aneuploidy of chromosome 21. In some embodiments, the methods disclosed herein utilize at least 15, at least 20, at least 30, at least 40, at least 50 or at least 60 nucleotides or all nucleotides of at least one of the following nucleic acid sequences:

SEQ ID NO: 59
AGACACACTTAAGCTGAGCTTAGAGCAAAGCATGTCCCTCAAGGTGACC
TTGCCGCATGGCCTGAACCTAGAATTCCCCTGACCAGGGTGGACAGCCA
TCACCATGGCCTTTCTGCCTGGCCTAGTATGGCTCTCCTTCGAACTCA
CCTAGACCCTTGCATCAAAGGACTCGGGGACTCTGCTGCAGTCATCCTA
GCACGGTCGAGAGGAGTAGGAAGGTGCCCAGCGGCTCAGCCTTTAAGGA
GGTCTATTGGTCACCATTGCTTCTGCCTTCTTGAGAACCATCACCCTCG
GAGGATCCGGTAGTGTATCCCAGTCAAGTGTCAAATGCGTTGTTCCCTG
GAGAGGAAGGCTTATTTCCAGAAAGTACTCTGACGTTTTGTAATTTGTG
ATTTCTATCACTGGCTCAGTGGCCTACCCACTGCTCAGCTCATGTGGCA
TGACCAGGCTGGGGCGTCGGGTCATCTTGTTCTCTGGGTGTGTGGCAAC
ACTGGTTTATGGCGTAATTTCCTTCCTGAGAAGAAATTCAGTAATTTCT
AATATTCAGGGCTTTAGGTAGAGGCCTGAAAATCACTCTCCATGCCTCT
TTCAGTATTTTAT

SEQ ID NO: 60
TAGTAAGCAAACAACTGAGGGACCAAAAAAAAAAAACAGGTTTTAAAGT
GACAAGGTTCAAATCTAGGGTAACAAATGGCAAGATGGGAGTACTCACA
TGATCAAAGAAATGTACCACTGCAAGCTTTTTGCTGCGCCTGGTAAAGA
TGCGCTGCACTTTAGCAATTTTGCCAAAATGGTTCTCCAGAATGGTCCT
GTCGTTGAGGTAGTCAGGGATGTTCTTGCACTGGATGGCTGTGACTTCA
GAGGGAGACAAGCCCCCAAGACTGTCTGTGCTCTCGCTTCTGTTACTCT
GACGCGCCGGAGTTCCTCTTAGAGAATCTAGGGGTTCAGAGAATGGACA
CTTAAACCATCAGATGTTTCCAACAACAGGAGGCACCAACTGTGTCGAA
GCAGAGGAAATTTTCAGATGTAAGACCTGCTCCGATGACATGTTAGAAT
CCCTAATGTTTATGGGAGATTTATCTGAAAAATCAAGCTAACACCCAGA
GAAACGTATTGAAAACCTGCCTGCAGGATTTACTCTATGTGCTACATTT
TCAGAGCTCACCTTCTTTCTTCTCTACTTTCAGTTTCTTCCTCTTTA
TTCACACCTGGAA

SEQ ID NO: 61
AGAAGGCGCTTATACATCACGGCCGTTGCTCATGCTTGGGTTAAAAAAG
GTCTCCCTTACAGCCAGGGCTCAGGATCCCTAGGCAGCTGGGGGTTGGC
CCCCGGGGCTCAGAGGTTAACCCTCTTCCTCTCACAGATGGGCCTAGCG
GTGGGAGCGTTTGTGGCAAGCTGCAGAAATGAGATGCGAGAGAGAGAGC
CCGTCCTTCAGAGTCCACGACAGCACAAAGGAAATGGCCGTGGGTGTTT
CGGGTTTAGCTGTCTTTGTTCCTACACGTTTATGTTACCTGCAAGTGGA
AATTCACCGGCACATCCTCTCAAAAATTATATTTTGTGTAAAAATATTT
AAGCACTAAATGAACCTCTGAGAGTCGGGATAGCGCTTCCTTGGAGGGG
GGAAAGTTTGGGGAGGAGGGCACGGGGGCTCCCTTCCTTGGAGGGGAGA
AAGTTTGGGGAGGAGGGCATGGGGGCTCCCTGAGGGCCAGTCATGCTGT
TCTTGGTGTGGGTGGCAGTGACACAGGCGTTTGCTTAGGGACAACTGTG
CTGTTCTGACTTAAGTGCCAGCCTGTGGAAGCGCCCACTGACTCAAGAT
TAGATAATCTCCC

SEQ ID NO: 62
GGATACAACTAGCCTAGAAAAAAGTCTTCAAAGTTCTTCTAAGCATTAG
TTCTCCAAGTGCTCCAATGAAGGCTAACAACCCAATCCAAAGTGAAGGC
TTCTTTTACTTCTTTATAAACAATTTCATAAATTTTTGTCTTAGTATATA
ATAAAAGGATAATAAGCTACAAGATAAATGATTAAAGATTAACCAAATT
TGGTATTCATGAACTAAAACGAACACTTTTCTAGATTTTAAGGTGGGCT
CTACTTCAGCTCATTACTAAGATGACTAAGCACCATGCAAAATTTGGCA
ATGCTGCCGGGTCTCAAGCATATATATGAAAAAGTCTGCAGCCACAACT
ACCCTAACAGAGATTTCAGAAAGGATGCTCTAAGTCTATCATGAGTGTA
ACCTTAAATAGATTACTTTTATACTGTTTTATTCTTCCTTTTAAACTGT
AAACTATATTAGTTTAATATCATCAATTTATAGTTAAGTTAGTTATTTG
GTTAACTCTACAGTGTAGAGCTATGCATATTTGTTGTCTGCACCTTTAA
CTTTCCAGTAACTAAATGTTACGCGTTCGGTGTTGGAGAAATGAGACAT
CTACTCAGTAACT

SEQ ID NO: 63
AAACGGACCACAACTTTCTTCAAACTTCTTCAAAGTTTGCATGTCTGGG
AGACCAATAAAGGGCAGGGCATACGAAGTAAGTCTGTTTAGGTCAGTTG
TTTATGGGTAGGTGCGACTTCATTCCTGTTCGCCCTACTTGCAGACATG
GTAACTTAGAACAGTTCTTCAGAAGCTGTTCGATGGCAACGTGGCGGAC
ATGGAGCTGTGAGGCCAAAGAATCTTTTTCTTGCACTTGGTGAGTTAAC
TCTTCAAAAACTTCTGTAAAAGATTTAAAAACTTTCATTTTTAGTATGC
AGAAAGCCGGTGCTATGATTTATATTTCAAGAACTCTAACTGAAATCTA
TGCATTGGGCAAAGTGTCACAATGAAACTGATTTGATACCAAGGAAACA
GTTCTGTTCTCTACAAAGCATATCAGTTCTGATCATCCTAGGCATCTGT
ATACTTTACATAGCCAAATGGAATTTGGCTCTTCTCCATCAAGTGACTA
CAGAGATACACAGCAAAAATGGTGGTTGCTACTGTAGCTGAGCTACTTT
TCTCAATTAGAATCTATAAACAGATTCAATTAGTACATAATGTGATTTA
TGGACAAGAAGTG

SEQ ID NO: 64
CTGCATTTTGTGTGAGTATAGCTGGATCCGCTTTGATTCTACAAATTAG
GTGCCCTTCTGTTTCTTAGTAATGTCATATTCTCTGACCACTGTAGCCA
CTTAAGATAGTCTCAAATATGAATAATTTTCAGTGGCCATAGTGGAGAA
GATGCTGACCCAGGAGGCTTATTCTCACCTCCACCTCTTAGACTCACAT
GTATGATTTTTTTTCTCCCTACCAAAGTGGCTAGTTTTGACAGCCTTT
AGGTTGCAGAACTGTTTATATTCGAAAGAAGACCTTACCTTCATAGAGC

-continued
ATTTTCCCGGGCAGTTGTTCTGCTTTGTGTTTTTAATATCTACTCTTAT

TCGGAGTCCCAAAATGAGTTAGCTTGGGTAGCTCTCACAATGAAAACTG

ATTTCTTCGCATAAAACTTTATTCTACCTTTTTGAAAACCAGCTGGAAA

TGATGAATGGTGGCTTCAACAGTAATGGTTCACGAAGAACTGATCGTGT

CCCCATCAATGAGGTCTTACCCATGGCAGGGCAATGGCGGTCTACTGTA

ATTCTGTGTTGGTTGTAGTAAGTTGGGGGAATATCAGGCCAAGAATCAA

CAGAGCTACGTGG

SEQ ID NO: 65
TAACCCTATCTAGTACAAGTTCAATTATGTTAAGCTAAAAACTTTGCTG

TAAAATATTAAATGCCAAGCTCAAAAAATCATAAGGGACATCCTCTCAG

CCCTAAGTTCTATTCACCCTGATACTCAATACATTTGAAAGTAAAACCT

CACTTTCGAAGTAACGCTGATACTGAAGCAAGGAGATGTTGAATGACTC

ACCCATTTCATAGCTTTTCCGTGGCAAAGCCTCACTAAAACCTATCTAA

TCCCTAGCTCCAATTCTTTAATCTCCATGGTGCTTCTGATTAATAGTTA

AACCACCCGGAAGTATGTTAAGGATACTAACATTTTCACCCCGAAGTAT

TATCCTTCGCCATCCTCTAGAATATGCTATGCAAAGAGGCCTAAAACAA

AATAAACTGCGACTTCAGCAGCTGAGAAGTAATGATTCCTTTCCCCTCC

CACACATCAAAACTTCCTATCCTATCCCCTCACTACTTTTTTCCTTTT

TAAAAGTAACAATGGTCATTGAGAACTACTAAATCCTGCAACACTCACA

AGGTAGTATGTACAACCACAGTTTTCCCCCGCGATACTTCACTGAAGTA

TTCAATACAGCCA

SEQ ID NO: 3
TGATAACACTGGGGAGAGTTAACTTTTTCACCTCTGTTTGTTGATATGC

CCCTTTGTGCTCCGTATTCACAAAGGGGCACCTCAACAAGCCCATCATT

TGTTAATGAATGCCTTTACTTTCATCGCCAGCAAGACATTTTCATAAAC

CCACCATCTACTTTGCAGTTCTCAAGAGTTGCTTCTCTTAAACTGGTGA

GGACGCGGCTAAGCCCTGGAAATGAGTCCAGATTCTCACGGTGGCCCAT

AAACACTGCTGTTTCCTCCCACCTAGGAAACCCGCAGACCTGCAGAACC

TGGCTCCCGGAACAAACCCTCCTTTCATGACTTTTGATGGTGAAGTCAA

GACGGATGTGAATAAGATCGAGGAGTTCTTAGAGGAGAAATTAGCTCCC

CCGAGGTAGGCCTCAGAAAACCAGTGTTCATAACTTGATTGTCACTTTC

CCCCACTAGTAGTCAGTTCTAAAGCTCTGGGCAGTGTGTGTGTGTGTGG

TTTTCTGCAGCCCACGGTGCTCACTTCCTTAATCATAACCCTGGTGTAA

CCAGATTAGAGTTCGGGGACCTGGGTTTCATTGTGCTGCACCTGCAGCT

TGGCAATCACAGT

SEQ ID NO: 67
GCAAACCACCCACTTCTGCCCTCTGCCCTTCTTCCCTTTTCTCGACACC

CTGCGGCCCCCCAGTTTCAGCAGAGTTTATTTGGGGTGAAAAACAAGAG

ATGCTCAGCGCCTGTGGGATGTGTGGGCTGACTCGTACATTAGGATGTG

TGTCAATCTGAAATAACCTGGCCGTTATATGGATGCCTTGGGGCTTGGG

GGGTTTCTGGCAGTCTGTCGAGCCCGAGGTGAATGTCCCCAAGGCTGCT

GGTGAATCAGATCCCTGGCGTTCTCCGTTGGCAGTTCAGCCCAACAGTT

-continued
TCTCTGCCCGGCCGTGCCTCTGCAGGTCCCTCCTCTGATCTGATTGGATT

AATATTTGAATCAATAGACTGAGTCAAGCAGAATGTGGGTGGGCCTCAT

GCAATCAGCTGAAGCCCTGAAAAGAGCAAAAGGGCTGCCCCTTCCCCCG

AGGAGGAGAGAACCCCTCCTGCCGGACGGCCTCCGAACTGGAACATCAG

CTTTTTGCTGCCTTTGGACTTGAACTGAAACATTACCTCTCCCTGGGTC

TTGAGTCTGCCTACGTTGGCACGGGAACTACACGTTGGCTCTCTTGGGC

CCCAGCTTGCTGA

SEQ ID NO: 68
CCTTTGTTCTTGTTGGCATCTGTGTAAGAGAATCCAGGGCCTGAACCAT

TGTCCACTCAAACAGACCATACACACCTGGTCCAGTTTTGTGCATGCCT

CCCTTTTCCACAGTGTGCCACTTGCTATAGTTCTGAACAAAAACTCCCT

TGCCCTTCGGAGCTTTATTTATTTTTAATTTGCTCTGTCATTGCATTGC

ATGCAATAGAAGCTTCCTGGTGGAAGCTCAATGTTCTGCTCAGTCCCAG

ACACGTTTTCAGCCACTGTATCATTGCCTTAGGTTGTGGTTTCCCCAAA

GCAGCACCGGAGGTAAGGGCTTGTGTGCAGGAGTTCACTTGGGAGGTGG

CTCTAGGAAATAGAAGCGAGTTTCCAGGAAGTGTGGGATGAATACGGGG

ATGGGGTGGGGGCGGGGAGGAATCCAATATGAATATATAATCTCATAT

TGAGTATAAAAATCCAATATGAGTATGTTTTCCAGACTGCTGCTAAGGA

GAATGGTGAATTATTCTACTGCGACCTTTTGAGGGTCCACACAATGCCT

CCCAAAACTATCTACCAGAGGGTGGATAGGAAGCATTGATCCATGGCTT

ATATTCCCCATTG

In some embodiments, the methods disclosed herein utilize at least 15, at least 20, at least 30, at least 40, at least 50 or at least 60 nucleotides of these nucleic acid sequences.

All nucleic acid sequences from U.S. Provisional Application No. 61/361,824 are incorporated by reference herein in their entirety.

In some embodiments, the methods disclosed herein use a portion, or the entirety, of one, more than one, such as 2, 3, 4, 5, 6, 7, 8, 9, 10 or all of SEQ ID NOs: 1-7, 29-38 and 59-68, and 83 to detect aneuploidy of chromosome 21. In additional embodiments, the methods disclosed herein use a portion, or the entirety, of one, more than one, such as 2, 3, 4, 5, 6, 7, 8, 9, 10 or all of SEQ ID NOs: 8, 19-28 and 49-58 to detect aneuploidy of chromosome 18. In some embodiments, the methods disclosed herein use a portion, or the entirety, of one, more than one, such as 2, 3, 4, 5, 6, 7, 8, 9, 10 or all of SEQ ID NOs: 9-18 and 39-48 to detect aneuploidy of chromosome 13.

In some embodiments, multiple selected loci are analyzed in parallel. Without being bound by theory, this can be to reduce the negative effect of inter-individual variation in absolute DNA methylation level at any given locus. The resulting test can provide highly accurate determination of the copy number of a particular chromosome or region of that chromosome relative to the other chromosomes tested. Biomarkers specific to chromosomes 13, 18 and 21, enable the test to define a normal range of inter-chromosomal count ratios between chromosomes 13, 18 and 21 for euploid fetuses and thereby determine deviation from this normal variation in when a fetus is tested that has aneuploidy on either chromosome 13, 18 or 21. A copy number ratio of 1:2 or 2:1 indicates the fetus has aneuploidy.

In some embodiments, fetal DNA is isolated from a maternal sample, such as, but not limited to, blood, serum or plasma. In addition to the acellular portion of the whole blood, DNA can also be recovered from the cellular fraction, enriched in the buffy coat portion, which can be obtained following centrifugation of a whole blood sample from the woman and removal of the plasma. There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as the QIAamp DNA Mini Kit or QIAamp DNA Blood Mini Kit (Qiagen, Hilden, Germany), GENOMICPREP™. Blood DNA Isolation Kit (Promega, Madison, Wis.), and GFX™. Genomic Blood DNA Purification Kit (Amersham, Piscataway, N.J.), may also be used to obtain DNA from a blood sample from a pregnant woman. Combinations of more than one of these methods may also be used. The methods disclosed herein use the methylation status of fetal DNA to isolate fetal DNA from maternal DNA. Once the fetal DNA is isolated, the copy number of an allele on a chromosome of interest can be determined.

In some examples, a sample, such as a blood, serum or plasma sample, is obtained from a pregnant woman at a suitable gestational age, such as 10 to 14 weeks, or 11 to 13 weeks for a human subject.

The gestational age may vary depending on the disorder to be assessed and the mammalian species. In some embodiments, a sample from the first or second trimester of pregnancy is utilized. Collection of blood from a pregnant female is performed in accordance with the standard protocol hospitals or clinics generally follow. For a pregnant woman, an appropriate amount of peripheral blood, such as between 5-50 ml, can be collected and may be stored according to standard procedures.

The analysis of fetal DNA found in maternal blood can performed using, for example, whole blood, serum, or plasma. The methods for preparing serum or plasma from maternal blood are well known among those of skill in the art. For example, a pregnant woman's blood can be placed in a tube containing EDTA or a specialized commercial product such as VACUTAINER® SST (Becton Dickinson, Franklin Lakes, N.J.) to prevent blood clotting, and plasma can then be obtained from whole blood through centrifugation.

Serum can be obtained with or without centrifugation following blood clotting. If centrifugation is used then it is typically, though not exclusively, conducted at an appropriate speed, such as 1,500-3,000 time gravity. Plasma or serum may be subjected to additional centrifugation steps or purification steps before being transferred to a fresh tube for DNA extraction.

There are numerous known methods for extracting DNA from a biological sample. General methods of DNA preparation (see, for example, Sambrook and Russell, Molecular Cloning: A Laboratory Manual 3d ed., 2001) can be followed; various commercially available reagents or kits, such as QIAAMP™ DNA Mini Kit or QIAAMP™ DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), can also be used to obtain DNA from a sample, such as a blood, serum or plasma sample, from a pregnant woman. Combinations of more than one of these methods may also be used.

The DNA present in a sample from a pregnant woman, whether or not extracted from the sample, is then treated with an agent capable of preferentially modifying DNA depending on whether the DNA sequence is methylated. For instance, this agent can be an enzyme that digests DNA in a methylation sensitive manner, for example only unmethylated DNA will be digested while methylated DNA remains unchanged. Another method includes the utilization of an agent that selectively converts a polynucleotide sequence depending on the methylation status. Typically, such an agent reacts with the unmethylated C residue(s) in a DNA molecule and converts each unmethylated C residue to a uracil (U) residue, whereas the methylated C residues remain unchanged. This C to U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., Proc. Natl. Acad. Sci. USA 93:9821-9826, 1996). These methods can be used to selectively purify fetal DNA from maternal DNA.

Additional methods for identifying and/or purifying regions of differential methylation and for determining the allelic ratio, are described in, for example, U.S. Pat. No. 5,871,917; U.S. Pat. No. 5,436,142; and U.S. Patent Application No. US20020155451A1, U.S. Patent Application No. US20030022215A1, U.S. Patent Application No. US20030099997, and U.S. Patent Application No. 2009/0019278, the contents of which are herein incorporated by reference in their entirety.

In one embodiment, the method utilizes a restriction enzyme. Examples of suitable restriction enzymes for use include, but are not limited to BsiSI, Hin2I, MseI, Sau3A, RsaI, TspEI, MaeI, NiaIII, DpnI and the like. One methyl-sensitive enzyme is Hpa II that recognizes and cleaves at nonmethylated CCGG sequences but not at CCGG sequences where the outer cytosine is methylated. In this manner, a restriction enzyme can be selected that cleaves maternal, but not fetal DNA, or that cleaves fetal, but not maternal DNA. The difference in methylation between maternal and fetal DNA can be assessed and used to isolate fetal DNA by bisulfide treatment followed by either 1) sequencing, or 2) base-specific cleavage followed by mass spectrometric analysis as described in von Wintzingerode et al., 2002, PNAS, 99:7039-44, herein incorporated by reference in its entirety. These methods generally allow the detection and/or amplification of fetal DNA. Thus, in some embodiments, the methylation status of the maternal DNA is used to selectively degrade maternal DNA. For example, maternal DNA can be restricted by an appropriate enzyme and degraded, or bisulfite treatment can be utilized. Any method that selects for fetal DNA can be utilized.

Following the methylation-dependent isolation of fetal DNA, one or more of the relevant nucleic acid sequences (such as at least 15, 20, 25, 30, 40, 50, 60 or all of the nucleotides of at least one of the nucleic acid sequences set forth as SEQ ID NO: 1-68 or 83) from the fetal source may be distinguished from their counterparts from the maternal source. In some embodiments, the allelic ratio is determined.

In some examples, a single nucleotide polymorphism (SNP) that is located adjacent to the CpG containing sequence, is utilized. For example, the SNP can be at most 1,000, at most 150, at most 100 or at most 50 base pairs from the CpG containing genomic sequence in the maternal (and/or fetal) genome. In other embodiments, a STR that is located adjacent to the CpG containing sequence is utilized. For example, the SNP can be at most 1,000, at most 150, at most 100 or at most 50 base pairs from the CpG containing genomic sequence in the maternal (and/or fetal) genome.

In additional embodiments, a nucleic acid including a SNP, such as a bi-allelic (heterozygous SNP) can be used to detect the copy number of chromosome 13, 18 or 21 in the fetus. In some embodiments, the SNP is a bi-allelic SNP that is within 150 base pairs, within 140 base pairs, within 130 base pairs, with 120 base pairs, within 110 base pairs, within 100 base pairs, within 75 base pairs, within 50 base pairs or within 25 base pairs of at least one of SEQ ID NOs: 1-68 or 83, and can be used to detect the copy number of chromosome 13, 18 or 21 in the fetus. Generally, the number of base pairs is measured from the 5' end of SEQ ID NO: 1-68 or SEQ ID NO: 83, or the 3' end of SEQ ID NO: 1-68 or SEQ ID NO: 83, depending on whether the bi-allelic SNP is located 5' or 3' of SEQ ID NO: 1-68 or SEQ ID NO: 83, respectively. In additional embodiments, the bi-allelic SNP is identified using a heterozygosity cut-off of about 0.25, such as 0.25.

In further embodiments, the copy number of a short tandem repeat is determined in order to detect fetal anueploidy. Short tandem repeats (STR) are also bi-allelic in karyotypically normal individuals and may or may not be tri-allelic or mono-allelic in individuals with aneuploidy. Thus, the disclosed methods can also determine the copy number of short tandem repeats. In additional embodiments, a nucleic acid including a STR, such as a bi-allelic, tri-allelic or mon-allelic (heterozygous STR) can be used to detect the copy number of chromosome 13, 18 or 21 in the fetus. In some embodiments, the STR is within 150 base pairs, within 140 base pairs, within 130 base pairs, with 120 base pairs, within 110 base pairs, within 100 base pairs, within 75 base pairs, within 50 base pairs or within 25 base pairs of at least one of SEQ ID NOs: 1-68 or 83, and can be used to detect the copy number of chromosome 13, 18 or 21 in the fetus. Generally, the number of base pairs is measured from the 5' end of SEQ ID NO: 1-68 or SEQ ID NO: 83, or the 3' end of SEQ ID NO: 1-68 or SEQ ID NO: 83, depending on whether the STR is located 5' or 3' of SEQ ID NO: 1-68 or SEQ ID NO: 83, respectively. In additional embodiments, the bi-allelic, tri-allelic or mono-allelic STR is identified using a heterozygosity cut-off of about 0.25, such as 0.25.

An amplification reaction is optional prior to another analysis, such as a copy number and/or sequenced based analysis for a fetal marker (including, but not limited to, a single nucleotide polymorphism, as described above, or one or more of SEQ ID NOs: 1-68 and 83), after treatment by the methylation-dependent differential modification process. In some embodiments, the amplification is performed to preferentially amplify a fetal marker such as such as at least 15, 20, 25, 30, 40, 50, 60 or all of the nucleotides of at least one of the nucleic acid sequences set forth as SEQ ID NO: 1-68 and 83, or a nucleic acid including a SNP, such as a bi-allelic SNP that is within 150 base pairs, within 140 base pairs, within 130 base pairs, with 120 base pairs, within 110 base pairs, within 100 base pairs, within 75 base pairs, within 50 base pairs or within 25 base pairs of at least one of SEQ ID NOs: 1-68 and 83, or a short tandem repeat.

A variety of polynucleotide amplification methods are well established and frequently used in research. For instance, the general methods of polymerase chain reaction (PCR) for polynucleotide sequence amplification are well known in the art. Reviews of PCR methods, protocols, and principles in designing primers, are provided for example, in Innis, et al., PCR Protocols: A Guide to Methods and Applications, Academic Press, Inc. N.Y., 1990, which is incorporated herein by reference. PCR reagents and protocols are also available from commercial vendors, such as Roche Molecular Systems.

PCR can be carried out as an automated process with a thermostable enzyme. In this process, the temperature of the reaction mixture is cycled through a denaturing region, a primer annealing region, and an extension reaction region automatically. Machines specifically adapted for this purpose are commercially available. Although PCR amplification of a target polynucleotide sequence (e.g., that of such as at least 15, 20, 25, 30, 40, 50, 60 or all of the nucleotides of at least one of the nucleic acid sequences set forth as SEQ ID NO: 1-68 or 83, or a SNP or short tandem repeat within a certain distance of at least one of these sequences) is typically used in practicing the present invention, one of skill in the art will recognize that the amplification of a genomic sequence can be accomplished by any known method, such as ligase chain reaction (LCR), transcription-mediated amplification, and self-sustained sequence replication or nucleic acid sequence-based amplification (NASBA), each of which provides sufficient amplification. Branched-DNA technology can also be used to qualitatively demonstrate the presence of a particular genomic sequence (see Nolte, Adv. Clin. Chem. 33:201-235, 1998).

In some embodiments, the fetal DNA is sequenced. Techniques for polynucleotide sequence determination are also well established and widely practiced in the relevant research field. DNA sequencing methods are routinely practiced in research laboratories, either manual or automated, and can be used in the methods disclosed herein (see for example, Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)). However, there are additional protocols suitable for detecting changes in a polynucleotide sequence, or for determining copy number, that are of use. These methods include, but are not limited to, mass spectrometry, primer extension, polynucleotide hybridization, real-time PCR, and electrophoresis. The methods can include short read DNA sequencing, pyrosequencing, real time PCR or single molecule sequencing (for example, Pacific Biosciences methodology).

The presence and quantity of the fetal nucleic acids can be determined and compared to a standard control, such as the presence and quantity in a maternal sample, the presence and quantity in a fetal sample from a fetus known not to have aneuploidy, the presence and quantity in a fetal sample from a fetus known to have aneuploidy, or a standard value. Furthermore, once it is determined that one or more of these nucleic acids is of fetal origin that is indeed present in the sample, particularly when the amount of the gene(s) is greater than (or less than) a pre-determined threshold, the sample and its equivalents are deemed to contain a sufficient amount of fetal DNA for further analyses. The quantity of these particular nucleic acid sequences can be measured as fetal markers indicative of certain conditions.

In several embodiments, an aneuploidy of a chromosome, such as chromosomes 13, 18 or 21, is determined by assessing the copy number of the target polynucleotide sequence. This can be done using any method that quantifies changes in the allelic ratio. In several examples, MASSARRAY® by Sequenome, pyrosequencing and TAQMAN® (digital format), sequencing, hybridization, padlock (inversion) probes can be utilized. A copy number that is significantly different from 1:1, such as a copy number of 1:2 or 2:1 indicates that the fetus is anuepolid. In some examples, the target polynucleotide sequence is a 15, 20, 20, 40, 50 or 60 nucleotide sequences located within any one of SEQ ID NOs: 1-68 or 83. In other examples, the target polynucleotide sequence is SEQ ID NO: 1-68 or 83. In further examples, the target polynucleotide sequence includes a target SNP, such as a bi-allelic SNP that is within 150 base pairs, within 140 base pairs, within 130 base pairs, with 120 base pairs, within 110 base pairs, within 100 base pairs, within 75 base pairs, within 50 base pairs or within 25 base pairs of at least one of SEQ ID NOs: 1-68 or 83. Thus, the SNP can be at most 150 base pairs, within 140 base pairs, within 130 base pairs, with 120 base pairs, within 110 base pairs, within 100 base pairs, within 75 base pairs, within 50 base pairs or within 25 base pairs from one of SEQ ID NOs: 1-68 or 83. In more examples, the target polynucleotide sequence is a short tandem repeat that is within 150 base pairs, within 140 base pairs, within 130 base pairs, with 120 base pairs, within 110 base pairs, within 100 base pairs, within 75 base pairs, within 50 base pairs or within 25 base pairs of at least one of SEQ ID NOs: 1-68 or 83.

Exemplary SNPs are provided below. The Rs. Id number and position information is provided; sequence information for these SNPs is incorporated by reference herein as available on Jun. 30, 2010. Information can also be found at the NCBI Single Nucleotide Polymorphism website. The SEQ ID NO: 2 that can be used with each SNP (see above) is indicated.

The following exemplary SNPs can be used to detect fetal aneuploidy of chromosome 21:
Sequence 42 chromosome 21 (SEQ ID NO: 1)
Rs.id 914232, snp.pos 45777178 (snp150_c21_mc_flank.csv)
Sequence 45 chromosome 21(SEQ ID NO: 2)
Rs.id 12627387, snp.pos 42355995 (snp150_c21_mc_flank.csv)
Sequence 16 chromosome 21(SEQ ID NO: 3)
Rs.id 225395, no snp.pos (snp150_c21_cm_flank.csv)
Sequence 69 chromosome 21 (SEQ ID NO: 4)
Rs.id 2013275, snp.pos 45158900 (snp150_c21_mc_flank.csv)
Sequence 76 chromosome 21(SEQ ID NO: 5)
Rs.id 2255526, snp.pos 46795967 (snp_150_c21_mc_flank.csv)
Sequence 88 chromosome 21 (SEQ ID NO: 6)
Rs.id 1539757, snp.pos 31559784 (snp150_c21_mc_flank.csv)
Sequence 99 chromosome 21 (SEQ ID NO: 7)
Rs.id 2838434, snp.pos 44161580 (snp150_c21_mc_flank.csv)
The following exemplary SNPs can be used to detect fetal aneuploidy of chromosome 13:
Row 2 (SEQ ID NO: 9)
Rs.id 9542537, no snp.pos (snp150_c13_cm_flank.csv)
Row 4 (SEQ ID NO: 10)
Rs.id 7983181, no snp.pos (snp150 c13_cm_flank.csv)
Row 6 (SEQ ID NO: 11)
Rs.id 166710, no snp.pos (snp150_c13_cm_flank.csv)
Row 8 (SEQ ID NO: 12)
Rs.id 9301803 or 9301804, no snp.pos (snp150_c13_cm_flank.csv)
Row 12 (SEQ ID NO: 13)
Rs.id 2025675, no snp.pos (snp150_c13_cm_flank.csv)
Row 14 (SEQ ID NO: 14)
Rs.id 11617606, no snp.pos (snp150_c13_cm_flank.csv)
Row 16 (SEQ ID NO: 15)
Rs.id 9535813 or 9316563, no snp.pos (snp150_c13_cm_flank.csv)
Row 20(SEQ ID NO: 16)
Rs.id 980094 or 2389355, no snp.pos (snp150_c13_cm_flank.csv)
Row 24 (SEQ ID NO: 17)
Rs.id 9536376, no snp.pos (snp150_c13_cm_flank.csv)
Row 26 (SEQ ID NO: 18)
Rs.id 9572623, no snp.pos (snp150_c13_cm_flank.csv)

The following exemplary SNPs can be used to detect aneuploidy of chromosome 18:
Row 2 (SEQ ID NO: 19)
Rs.id 12955286 or 1852531, no snp.pos (snp150_c18_cm_flank.csv)
Row 6 (SEQ ID NO: 20)
Rs.id 1244833, no snp.pos (snp150_c18_cm_flank.csv)
Row 8 (SEQ ID NO: 21)
Rs.id 2923220, no snp.pos (snp150_c18_cm_flank.csv)
Row 10 (SEQ ID NO: 22)
Rs.id 16977803, no snp.pos (snp150_c18_cm_flank.csv)
Row 12 9(SEQ ID NO: 23)
Rs.id 603884, no snp.pos (snp150_c18_cm_flank.csv)
Row 14 (SEQ ID NO: 24)
Rs.id 4800573, no snp.pos (snp150_c18_cm_flank.csv)
Row 16 (SEQ ID NO: 25)
Rs.id 12970409 (snp150_c18_cm_flank.csv)
Row 18 (SEQ ID NO: 26)
Rs.id 11663168 or 11663172 (snp150_c18_cm_flank.csv)
Row 22 (SEQ ID NO: 27)
Rs.id 7505859 (snp150_c18_cm_flank.csv)
Row 24 (SEQ ID NO: 28)
Rs.id 8095592 (snp150_c18_cm_flank.csv)
The following exemplary SNPs can be used to detect aneuploidy of chromosome 21:
Row 2 (SEQ ID NO: 29)
Rs.id 225395 (snp150_c21_cm_flank.csv)
Row 4 (SEQ ID NO: 30)
Rs.id 2837528 (snp150_c21_cm_flank.csv)
Row 6 (SEQ ID NO: 31)
Rs.id 2827557 (snp150_c21_cm_flank.csv)
Row 8 (SEQ ID NO: 32)
Rs.id 2822564 (snp150_c21_cm_flank.csv)
Row 10 (SEQ ID NO: 33)
Rs.id 233895 (snp150_c21_cm_flank.csv)
Row 12(SEQ ID NO: 34)
Rs.id 9980448 (snp150_c21_cm_flank.csv)
Row 14 (SEQ ID NO: 35)
Rs.id 2827384 (snp150_c21_cm_flank.csv)
Row 16 (SEQ ID NO: 36)
Rs.id 20457173 (snp150_c21_cm_flank.csv)
Row 18 (SEQ ID NO: 37)
Rs.id 9977149 (snp150_c21_cm_flank.csv)
Row 20 (SEQ ID NO: 38)
Rs.id 3453 (snp150_c21_cm flank. Csv)
The following exemplary SNPs can be used to detect fetal aneuploidy of chromosome 13:
Row 2 (SEQ ID NO: 39)
Rs.id 7317471, snp.pos 20518084 (snp150_c13_mc_flank.csv)
Row 4 (SEQ ID NO: 40)
Rs.id 3742160, snp.pos 105943830 (snp150_c13_mc_flank.csv)
Row 6 (SEQ ID NO: 41)
Rs.id 206321, snp.pos 31888780 (snp150_c13_mc_flank.csv)
Row 8 (SEQ ID NO: 42)
Rs.id 9579199 or 9578047, snp.pos 28062783 or 28062731 (snp150_c13_mc_flank.csv)
Row 12 (SEQ ID NO: 43)
Rs.id 9506534, snp.pos 20145165 (snp150_c13 mc_flank.csv)
Row 14 (SEQ ID NO: 44)
Rs.id 1411551, snp.pos 109171036 (snp150_c13_mc_flank.csv)
Row 17 (SEQ ID NO: 45)

Rs.id 9515119, snp.pos 109207337 (snp150_c13_mc_flank.csv)
Row 19 (SEQ ID NO: 46)
Rs.id 9551454, snp.pos 27730987 (snp150_c13_mc_flank.csv)
Row 21 (SEQ ID NO: 47)
Rs.id 17593586, snp.pos 40693966 (snp150_c13_mc_flank.csv)
Row 23 (SEQ ID NO: 48)
Rs.id 166753, snp.pos 108544047 (snp150_c13_mc_flank.csv)

The following exemplary SNPs can be used to detect fetal aneuploidy of chromosome 18:
Row 2 (SEQ ID NO: 49)
Rs.id 8083921, snp.pos 58917082 (snp150 c18_mc_flank.csv)
Row 4 (SEQ ID NO: 50)
Rs.id 546680, snp.pos 30988098 (snp150_c18_mc_flank.csv)
Row 6 (SEQ ID NO: 51)
Rs.id 4891159, snp.pos 72230929 (snp150_c18_mc_flank.csv)
Row 8 (SEQ ID NO: 52)
Rs.id 16978450, snp.pos 41517284 (snp150 c 8 flank.csv)
Row 10 (SEQ ID NO: 53)
Rs.id 7245283, snp.pos 957483 (snp150_c18_mc_flank.csv)
Row 12 (SEQ ID NO: 54)
Rs.id 9945379, snp.pos 10928309 (snp150_c18_mc_flank.csv)
Row 14 (SEQ ID NO: 55)
Rs.id 12958513 or 16978452 or 7228161, snp.pos 41520914 or 41521069 or 41520883 (snp150_c18_mc_flank.csv)
Row 21 (SEQ ID NO: 56)
Rs.id 11152348, snp.pos 58349472 (snp150 c18 mc_flank.csv)
Row 23 (SEQ ID NO: 57)
Rs.id 528129, snp.pos 24748157 (snp150_c18_mc_flank.csv)
Row 25 (SEQ ID NO: 58)
Rs.id 16978485 or 9966818, snp.pos 41589920 or 41589897 (snp150 c18_mc_flank.csv)

The following exemplary SNPs can be used to detect fetal aneuploidy of chromosome 21:
Row 2 (SEQ ID NO: 59)
Rs.id 11702354, snp.pos 34806395 (snp150_c21_mc_flank.csv)
Row 4 (SEQ ID NO: 60)
Rs.id 11702450, snp.pos 46528077 (snp150_c21_mc_flank.csv)
Row 6 (SEQ ID NO: 61)
Rs.id 2839418, snp.pos 42192853 (snp150_c21_mc_flank.csv)
Row 8 (SEQ ID NO: 62)
Rs.id 6517531, snp.pos 39559517 (snp150_c21_mc_flank.csv)
Row 10 (SEQ ID NO: 63)
Rs.id 2824493, snp.pos 18087813 (snp150_c21_mc_flank.csv)
Row 12 (SEQ ID NO: 64)
Rs.id 2835676, snp.pos 37513181 (snp150_c21 mc_flank.csv)
Row 14 (SEQ ID NO: 65)
Rs.id 2823026, snp.pos 15346340 (snp150_c21_mc_flank.csv)
Row 16 (SEQ ID NO: 66)
Rs.id 6517254 or 2070368, snp.pos 35002160 or 35002268 (snp150_c21_mc_flank.csv)
Row 20 (SEQ ID NO: 67)
Rs.id 220269, snp.pos 42357265 (snp150_c21_mc_flank.csv)
Row 22 (SEQ ID NO: 68)
Rs.id 2823304, snp.pos 15784966 (snp150_c21_mc_flank.csv)

In some embodiments, the methods disclosed herein utilize at least 1, at least 5, at least 10, at least 15, at least 20, at least 30, at least 40, at least 50 or at least 60 nucleotides of these SNPs.

In some embodiments, once a the fetus is diagnosed with aneuploidy, such as a trisomy or a monosomy, an indication of that diagnosis can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, voltammetric trace, or other diagram), or an audible output.

Molecular Methods for Detection of Nucleic Acids

Polymorphisms, such as SNPs, also can be used to detect the allele frequency both in the maternal sample and the fetal sample. Generally, the methods disclosed herein involve an assessment of nucleic acid sequence. Molecular techniques of use in all of these methods are disclosed below.

Preparation of Nucleic Acids for Analysis:

Nucleic Acid Molecules can be prepared for analysis using any technique known to those skilled in the art. Generally, such techniques result in the production of a nucleic acid molecule sufficiently pure to determine the presence or absence of one or more variations at one or more locations in the nucleic acid molecule. Such techniques are described for example, in Sambrook, et al., Molecular Cloning: A Laboratory Manual (Cold Spring Harbor Laboratory, New York) (1989), and Ausubel, et al., Current Protocols in Molecular Biology (John Wiley and Sons, New York) (1997), incorporated herein by reference.

When the nucleic acid of interest is present in a cell, it can be necessary to first prepare an extract of the cell and then perform further steps, such as differential precipitation, column chromatography, extraction with organic solvents and the like, in order to obtain a sufficiently pure preparation of nucleic acid. Extracts can be prepared using standard techniques in the art, for example, by chemical or mechanical lysis of the cell. Extracts then can be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. When chaotropic salts are used, it can be desirable to remove the salts from the nucleic acid-containing sample. This can be accomplished using standard techniques in the art such as precipitation, filtration, size exclusion chromatography and the like.

Amplification of Nucleic Acid Molecules:

Optionally, the nucleic acid samples obtained from the subject are amplified prior to detection. Target nucleic acids are amplified to obtain amplification products, including a DNA that includes a SNP, from the sample prior to detection.

Any nucleic acid amplification method can be used. An example of in vitro amplification is the polymerase chain reaction (PCR), in which a biological sample obtained from a subject is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see PCT Publication NO. WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

In specific examples, the target sequences to be amplified from the subject include a nucleotide sequence of interest including the SNP. In certain embodiments, target sequences containing one or more of SEQ ID NOs: 1-68, or genetic region within, for example, 150 base pairs of one of SEQ ID NO: 1-68 are amplified. In an embodiment, a single SNP with exceptionally high predictive value is amplified.

A pair of primers can be utilized in the amplification reaction. One or both of the primers can be labeled, for example with a detectable radiolabel, fluorophore, or biotin molecule. The pair of primers includes an upstream primer (which binds 5' to the downstream primer) and a downstream primer (which binds 3' to the upstream primer). The pair of primers used in the amplification reactions are selective primers which permit amplification of a size related marker locus. Primers can be selected to amplify a DNA including a SNP. Numerous primers can be designed by those of skill in the art simply by determining the sequence of the desired target region, for example, using well known computer assisted algorithms that select primers within desired parameters suitable for annealing and amplification.

If desired, an additional pair of primers can be included in the amplification reaction as an internal control. For example, these primers can be used to amplify a "housekeeping" nucleic acid molecule, and serve to provide confirmation of appropriate amplification. In another example, a target nucleic acid molecule including primer hybridization sites can be constructed and included in the amplification reactor. One of skill in the art will readily be able to identify primer pairs to serve as internal control primers.

Primer Design Strategy:

Increased use of polymerase chain reaction (PCR) methods has stimulated the development of many programs to aid in the design or selection of oligonucleotides used as primers for PCR. Four examples of such programs that are freely available via the Internet are: PRIMER™ by Mark Daly and Steve Lincoln of the Whitehead Institute (UNIX, VMS, DOS, and Macintosh), Oligonucleotide Selection Program by Phil Green and LaDeana Hiller of Washington University in St. Louis (UNIX, VMS, DOS, and Macintosh), PGEN™ by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Designing oligonucleotides for use as either sequencing or PCR primers to detect requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding programs. If a possible stem structure is observed, the sequence of the primer can be shifted a few nucleotides in either direction to minimize the predicted secondary structure. When the amplified sequence is intended for subsequence cloning, the sequence of the oligonucleotide can also be compared with the sequences of both strands of the appropriate vector and insert DNA. A sequencing primer only has a single match to the target DNA. It is also advisable to exclude primers that have only a single mismatch with an undesired target DNA sequence. For PCR primers used to amplify genomic DNA, the primer sequence can be compared to the sequences in the GENBANK™ database to determine if any significant matches occur. If the oligonucleotide sequence is present in any known DNA sequence or, more importantly, in any known repetitive elements, the primer sequence should be changed.

Detection of Alleles:

The nucleic acids obtained from the sample can be genotyped to identify the particular allele present for a marker locus. A sample of sufficient quantity to permit direct detection of marker alleles from the sample can be obtained from the subject. Alternatively, a smaller sample is obtained from the subject and the nucleic acids are amplified prior to detection. Any target nucleic acid that is informative for a chromosome haplotype can be detected. Generally, the target nucleic acid corresponds to a SNP. Any method of detecting a nucleic acid molecule can be used, such as hybridization and/or sequencing assays.

Hybridization is the binding of complementary strands of DNA, DNA/RNA, or RNA. Hybridization can occur when primers or probes bind to target sequences such as target sequences within genomic DNA. Probes and primers that are useful generally include nucleic acid sequences that hybridize (for example under high stringency conditions) with a nucleic acid sequence including the SNP of interest, but do not hybridize to a reference allele, or that hybridize to the reference allele, but do not hybridize to the SNP. Physical methods of detecting hybridization or binding of complementary strands of nucleic acid molecules, include but are not limited to, such methods as DNase I or chemical footprinting, gel shift and affinity cleavage assays, Southern and Northern blotting, dot blotting and light absorption detection procedures. The binding between a nucleic acid primer or probe and its target nucleic acid is frequently characterized by the temperature ($T_m$) at which 50% of the nucleic acid probe is melted from its target. A higher ($T_m$) means a stronger or more stable complex relative to a complex with a lower (Tm).

Generally, complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide faun base pairs with a targeted region of a DNA molecule, that oligonucleotide is said to have 66.67% complementarity to the region of DNA targeted.

In the present disclosure, "sufficient complementarity" means that a sufficient number of base pairs exist between an oligonucleotide molecule and a target nucleic acid sequence (such as a SNP) to achieve detectable and specific binding.

When expressed or measured by percentage of base pairs formed, the percentage complementarity that fulfills this goal can range from as little as about 50% complementarity to full (100%) complementarity. In general, sufficient complementarity is at least about 50%, for example at least about 75% complementarity, at least about 90% complementarity, at least about 95% complementarity, at least about 98% complementarity, or even at least about 100% complementarity. The qualitative and quantitative considerations involved in establishing binding conditions that allow one skilled in the art to design appropriate oligonucleotides for use under the desired conditions is provided by Beltz et al. *Methods Enzymol* 100: 266-285, 1983, and by Sambrook et al. (ed.), *Molecular Cloning: A Laboratory Manual*, 2nd ed., vol. 1-3, Cold Spring Harbor Laboratory Press, Cold Spring Harbor, N.Y., 1989.

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning: a laboratory manual*, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Complementarity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Complementarity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 50% Complementarity)
Hybridization: 6×SSC at RT to 55° C. for 16-20 hours
Wash at least twice: 2×-3×SSC at RT to 55° C. for 20-30 minutes each.

Methods for labeling nucleic acid molecules so they can be detected are well known. Examples of such labels include non-radiolabels and radiolabels. Non-radiolabels include, but are not limited to an enzyme, chemiluminescent compound, fluorescent compound (such as FITC, Cy3, and Cy5), metal complex, hapten, enzyme, colorimetric agent, a dye, or combinations thereof. Radiolabels include, but are not limited to, $^{125}I$, $^{32}P$ and $^{35}S$. For example, radioactive and fluorescent labeling methods, as well as other methods known in the art, are suitable for use with the present disclosure. In one example, primers used to amplify the subject's nucleic acids are labeled (such as with biotin, a radiolabel, or a fluorophore). In another example, amplified target nucleic acid samples are end-labeled to form labeled amplified material. For example, amplified nucleic acid molecules can be labeled by including labeled nucleotides in the amplification reactions.

Nucleic acid molecules corresponding to one or more SNPs or alleles including the SNP can also be detected by hybridization procedures using a labeled nucleic acid probe, such as a probe that detects only one alternative allele at a marker locus. Most commonly, the target nucleic acid (or amplified target nucleic acid) is separated based on size or charge and transferred to a solid support. The solid support (such as membrane made of nylon or nitrocellulose) is contacted with a labeled nucleic acid probe, which hybridizes to it complementary target under suitable hybridization conditions to form a hybridization complex.

Hybridization conditions for a given combination of array and target material can be optimized routinely in an empirical manner close to the $T_m$ of the expected duplexes, thereby maximizing the discriminating power of the method. For example, the hybridization conditions can be selected to permit discrimination between matched and mismatched oligonucleotides. Hybridization conditions can be chosen to correspond to those known to be suitable in standard procedures for hybridization to filters (and optionally for hybridization to arrays). In particular, temperature is controlled to substantially eliminate formation of duplexes between sequences other than an exactly complementary allele of the selected marker. A variety of known hybridization solvents can be employed, the choice being dependent on considerations known to one of skill in the art (see U.S. Pat. No. 5,981,185).

Once the target nucleic acid molecules have been hybridized with the labeled probes, the presence of the hybridization complex can be analyzed, for example by detecting the complexes.

Methods for detecting hybridized nucleic acid complexes are well known in the art. In one example, detection includes detecting one or more labels present on the oligonucleotides, the target (e.g., amplified) sequences, or both. Detection can include treating the hybridized complex with a buffer and/or a conjugating solution to effect conjugation or coupling of the hybridized complex with the detection label, and treating the conjugated, hybridized complex with a detection reagent. In one example, the conjugating solution includes streptavidin alkaline phosphatase, avidin alkaline phosphatase, or horseradish peroxidase. Specific, non-limiting examples of conjugating solutions include streptavidin alkaline phosphatase, avidin alkaline phosphatase, or horseradish peroxidase. The conjugated, hybridized complex can be treated with a detection reagent. In one example, the detection reagent includes enzyme-labeled fluorescence reagents or calorimetric reagents. In one specific non-limiting example, the detection reagent is enzyme-labeled fluorescence reagent (ELF) from Molecular Probes, Inc. (Eugene, Oreg.). The hybridized complex can then be placed on a detection device, such as an ultraviolet (UV) transilluminator (manufactured by UVP, Inc. of Upland, Calif.). The signal is developed and the increased signal intensity can be recorded with a recording device, such as a charge coupled device (CCD) camera (manufactured by Photometrics, Inc. of Tucson, Ariz.). In particular examples, these steps are not performed when radiolabels are used. In particular examples, the method further includes quantification, for instance by determining the amount of hybridization.

Allele Specific PCR:

Allele-specific PCR differentiates between target regions differing in the presence of absence of a variation or polymorphism. PCR amplification primers are chosen based upon their complementarity to the target sequence, such as nucleic acid sequence in a DNA including a SNP, a specified region of an allele including a SNP, or to the SNP itself. The primers bind only to certain alleles of the target sequence. This method is described by Gibbs, *Nucleic Acid Res.* 17:12427 2448, 1989, herein incorporated by reference.

Allele Specific Oligonucleotide Screening Methods:

Further screening methods employ the allele-specific oligonucleotide (ASO) screening methods (e.g. see Saiki et al., *Nature* 324:163-166, 1986). Oligonucleotides with one or more base pair mismatches are generated for any particular allele or haplotype block. ASO screening methods detect mismatches between one allele (or haplotype block) in the target genomic or PCR amplified DNA and the other allele (or haplotype block), showing decreased binding of the oligonucleotide relative to the second allele (i.e. the other allele) oligonucleotide. Oligonucleotide probes can be designed that under low stringency will bind to both polymorphic forms of the allele, but which at high stringency, only bind to the allele to which they correspond. Alternatively, stringency conditions can be devised in which an essentially binary response is obtained, i.e., an ASO corresponding to a variant form of the target gene will hybridize to that allele (haplotype block), and not to the reference allele (haplotype block).

Ligase Mediated Allele Detection Method:

Ligase can also be used to detect point mutations, such as the tag SNPs disclosed herein, in a ligation amplification reaction (e.g. as described in Wu et al., *Genomics* 4:560-569, 1989). The ligation amplification reaction (LAR) utilizes amplification of specific DNA sequence using sequential rounds of template dependent ligation (e.g. as described in Wu, supra, and Barany, *Proc. Nat. Acad. Sci.* 88:189-193, 1990).

Denaturing Gradient Gel Electrophoresis:

Amplification products generated using the polymerase chain reaction can be analyzed by the use of denaturing gradient gel electrophoresis. Different alleles (haplotype blocks) can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_M$). Melting domains are at least 20 base pairs in length, and can be up to several hundred base pairs in length.

Differentiation between alleles (haplotype blocks) based on sequence specific melting domain differences can be assessed using polyacrylamide gel electrophoresis, as described in Chapter 7 of Erlich, ed., PCR Technology, Principles and Applications for DNA Amplification, W. H. Freeman and Co., New York (1992).

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501-527, 1986, and Myers et al., in Genomic Analysis, A Practical Approach, K. Davies Ed. IRL Press Limited, Oxford, pp. 95 139, 1988. The electrophoresis system is maintained at a temperature slightly below the Tm of the melting domains of the target sequences.

In an alternative method of denaturing gradient gel electrophoresis, the target sequences can be initially attached to a stretch of GC nucleotides, termed a GC clamp, as described in Chapter 7 of Erlich, supra. In one example, at least 80% of the nucleotides in the GC clamp are either guanine or cytosine. In another example, the GC clamp is at least 30 bases long. This method is particularly suited to target sequences with high $T_m$'s.

Generally, the target region is amplified by polymerase chain reaction. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions. DNA fragments differing by a single base change will migrate through the gel to different positions, which can be visualized by ethidium bromide staining.

Temperature Gradient Gel Electrophoresis:

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis. *Single-Strand Conformation Polymorphism Analysis*: Target sequences, such as alleles can be differentiated using single-strand conformation polymorphism analysis, which identifies base differences by alteration in electrophoretic migration of single stranded PCR products, for example as described in Orita et al., *Proc. Nat. Acad. Sci.* 85:2766-2770, 1989. Amplified PCR products can be generated as described above, and heated or otherwise denatured, to form single stranded amplification products. Single-stranded nucleic acids can refold or form secondary structures which are partially dependent on the base sequence. Thus, electrophoretic mobility of single-stranded amplification products can detect base-sequence difference between alleles.

Chemical or Enzymatic Cleavage of Mismatches:

Quantitative differences between target sequences, such as alleles, can also be detected by differential chemical cleavage of mismatched base pairs, for example as described in Grompe et al., *Am. J. Hum. Genet.* 48:212-222, 1991. In another method, differences between target sequences, such as alleles, can be detected by enzymatic cleavage of mismatched base pairs, as described in Nelson et al., Nature Genetics 4:11-18, 1993. Briefly, genetic material from an animal and an affected family member can be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms.

Non-Gel Systems:

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete (there is a mismatch of some form) the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Non-PCR Based Allele Detection:

The identification of a DNA sequence can be made without an amplification step, based on polymorphisms including restriction fragment length polymorphisms in a subject and a control, such as a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes can be labeled directly or indirectly, such that by assaying for the presence or absence of the probe, one can detect the presence or absence of the target sequence. Direct labeling methods include radioisotope labeling, such as with $^{32}P$ or $^{35}S$. Indirect labeling methods include fluorescent tags, biotin complexes which can be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to a nucleic acid sequence wherein a polymorphism, such as a tag SNP, and thus defining a genetic marker, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Exemplary tandem repeat hybridization probes for use in the methods disclosed are those that recognize a small number of fragments at a specific locus at high stringency hybridization conditions, or that recognize a larger number of fragments at that locus when the stringency conditions are lowered.

The present methods can also be embodied in a device or a system comprising one or more such devices, which is capable of carrying out all or some of the method steps described herein.

The disclosure is illustrated by the following non-limiting Examples.

EXAMPLES

Prenatal screening for Down's Syndrome and other chromosomal abnormalities is most effectively achieved using interventional procedures such as amniocentesis and chorionic villus sampling (CVS) that obtain fetal or placental cells (respectively) for karyotype analysis. Unfortunately, these procedures involve a risk of spontaneous abortion that has been reported to be as high as 1% (Mujezinovic and Alfirevic, Obst. Gyn. 110: 687-694, 2007) (although complication rates have fallen recently) and are generally only routinely offered to expectant mothers who have an elevated risk of carrying an aneuploid fetus. Minimally invasive screening protocols utilizing specific protein markers detectable in maternal serum in combination with ultrasound have been in use for a number of years but these do not achieve desirable levels of sensitivity and specificity and so are not definitive (Summers et al., J. Med. Screen. 10: 107-11, 2003a, Meier et al., Prenat. Diagn. 23: 443-446, 2003, Summers et al., Obstet. Bynecol. 101: 1301-1308, 2003b). Furthermore, these markers are only surrogates of the underlying genetic abnormality.

As described herein, a high-throughput approach was used to characterize DNA methylation patterns of CVS and MBCs obtained during the first trimester of pregnancy. The biomarker discovery efforts on chromosomes 13, 18 and 21, which are frequently found to be aneuploid in live births. A list of epigenetic biomarkers was established, wherein these biomarkers each display differential methylation patterns between these tissues on human chromosomes 13, 18 and 21. A custom microarray is also disclosed. The data presented herein provide a useful and unique catalogue of tissue-specific methylation patterns that can be used for fetal diagnosis.

Human chromosomal abnormalities are relatively common, occurring in approximately 10-30% of conceptions. It has been estimated that 1 in 300 live-born infants are aneuploid and that this figure rises to 1 in 25 for stillborn infants. By far the commonest form of aneuploidy is trisomy 21 resulting in Down syndrome, which occurs at an average rate of approximately 1 of 500 live births and 1 of 250 conceptions (Hook, Lancet 340: 1109, 1992, Crotty et al., May Clin. Proc. 67: 373-378, 1992). Other common autosomal trisomies including trisomy 18 (Edward syndrome) and trisomy 13 (Patau syndrome) occur with birth incidences of 11n 6,500 and 1 in 12,500 (Spencer, Am. J. Med. Med. Genet. C. Semin. Med. GEnet. 145C: 18-32, 2007, Hassold et al., Environ. Mol. Mutagen. 28: 167-175, 1996).

Example 1

Materials and Methods

Tissue Handling and DNA Extraction:

All samples used in the studies described below were de-identified discarded tissues. CVS samples were obtained between gestational weeks 11 and 13. Samples were dissected under a microscope and separated from any decidua or flecks of blood. The culture media was removed and the tissue placed in 1.5-2.0 mL microcentrifuge tubes before freezing at −80° C. until DNA was extracted. To extract the DNA, one 5 mm stainless steel bead and 180 µL buffer ATL (from Qiagen's DNEASY® Blood and Tissue kit) were added to each CVS sample. The samples were placed in the TIS-SUELYSER® (Qiagen) Adaptor set 2×24, and the TIS-SUELYSER® was operated for 20 seconds at 30 Hz. The DNA was then purified using the DNEASY® Blood and Tissue kit as per the manufacturer's protocol. MBCs were obtained between gestational weeks 11 and 13. DNA was extracted from the MBC's using a modified protocol previously described by Iovannisci, et al., 2006 (Iovannisci et al., 2006), using reagents from the MASTUREPURE® DNA Purification Kit (Epincentre Technologies, Madison, Wis., Cat. No. MCD85201). Briefly, clotted blood (approximately 1 mL) was mixed with an equal volume (1 mL) of 2× Tissue and Cell Lysis Solution, votexed for 10 s and combined with 2 mL Tissue and Cell Lysis Solution (MASTUREPURE® kit) containing 25 ng/µL proteinase K. 2 mL of MPC Protein Precipitation Reagent was added to the total volume (4 mL) of the lysed sample and vortex vigorously for 10-15 sec, after which samples were cooled on ice for 1 hour. Cell debris were then pelleted by centrifugation (×2) for at least 30 min at 2000 g and supernatants transferred to a new 50 mL conical tube.

DNA was precipitated in 2 volumes of isoproponal, purified by phenol/chloroform extraction and resuspended in 504 DNAse/RNAse free water.

Target DNA Preparation for Microarray Analysis:

Genomic DNA samples (3 µg) were digested for 2 hours at 37° C. with 50 U HpaII (New England Biolabs [NEB]) in 90 µL total reaction volume using NEB buffer 4. A second aliquot of 50 U, 1 µL of buffer 4, and 4 µL water were added and digestion continued overnight (total reaction volume was 100 µL). Mock digestion controls were included to monitor digestion efficiency. Following overnight digestion, reactions were digested further with 5 uL (50 U) of TspRI (NEB) at 65° C. for three hours. Reactions were then incubated further with 75 U (0.75 µl) Exonuclease III (NEB) and incubated at 30° C. for 1 hour. Enzymatic activity was then nullified by heating at 70° C. for 20 min after which 50 U of RecJF (NEB) were added to remove single stranded DNA. Reactions were incubated for 30 min at 37° C. and inactivated at 65° C. for 20 min. Reactions were then phenol-chloroform extracted and the DNA precipitated and resuspended in 21.2 µL nuclease-free deionized water. Finally, extracted genomic DNA was quantified and assessed for purity using a NanoDrop ND-1000 UV-VIS Spectrophotometer.

CGH Target Labeling and Hybridization:

Experimental and reference DNA were labeled with Cy3-dUTP and Cy5-dUTP respectively, and vice versa for dye-swaps, using a BioPrime CGH Genomic Labeling kit per the manufacturer's protocol (Agilent). Hybridization was performed in a mix containing 50 µL of human Cot-1, 52 µL of Agilent 10× blocking agent, 260 µL of Agilent 2× HiRPM hybridization buffer, and 158 µL of the labeled DNA. The hybridization mix was heated to 95° C. for 3 minutes, then incubated at 37° C. for 30 minutes and applied onto the active array area. Hybridization with gentle agitation was carried out at 65° C. for 40 hours. After hybridization, the slides were washed in Oligo aCGH Wash Buffer 1 and Oligo aCGH Wash Buffer 2, followed by acetonitrile and Stabilization and Drying Solution (Agilent) per the manufacturer's protocol. The slides were scanned using an Agilent Scanner and the data was analyzed using Agilent Feature Extraction software 8.1 (Agilent). Visualization and comparison of the datasets were done with CGH-Analytics 3.2 (Agilent).

Pyrosequencing:

500 ng of each MBC and CVS sample was bisulfite converted using the EZ DNA® Methylation Kit (Zymo Research, Orange, Calif.) as per manufacturer's protocol. Each PCR reaction contained 1× AmpliTaq buffer Gold, 2.0 mM $MgCl_2$, 0.5 mM dNTP, 0.2 µM each primer, 20 ng bisulfite converted DNA, and 1.5 U AmpliTaq Gold in a 504 reaction volume. The PCR primers were purchased from Integrated DNA Technologies, Inc. (Coralville, Iowa), and the reverse primers biotinylated at their 5' end. PCR cycling conditions were: 95° for 10 min, 47×(95° for 15 s, Tm for 30 s, 72° for 30 s), 72° for 7 min, 4° hold. Pyrosequencing was performed and analyzed on the above-amplified PCR products on a Biotage PSQ 96MA machine as per the manufacturer's protocol (Biotage Co., Uppsala, Sweden). Unless otherwise noted, all reagents and consumables were purchased directly from Biotage. In brief, 404 of a Streptavidin Sepharose bead (GE Healthcare Co.)/binding buffer mixture were combined with 40 µL of each amplified PCR product in a V-well 96 well plate and mixed for ten minutes at maximum speed on a vortex. Each sequencing primer was diluted in annealing buffer and this mixture placed in a well in a PSQ 96 low plate. After mixing, the beads were captured using a vacuum prep tool and then flushed with 70% ethanol, 0.2M NaOH, and wash buffer successively for 15 seconds each. Beads were released into the sequencing primer/annealing buffer solution by turning off the vacuum and placing the probes in this solution. The primers were annealed by heating to 95° for 2 minutes. Based on the sequence to be analyzed, the pyrosequencing cartridge was prepared, the plate loaded into the machine, and the pyrosequencing program initiated.

Sequenom Epityper Analysis:

PCR reactions were carried out in a 384 well format as follows. To each reaction was added 1.42 µL $ddH_2O$, 0.5 µL 10× Hot Star Buffer (Qiagen) (15 mM $MgCl_2$, Tris-C1, KCl, $(NH_4)_2SO4$, pH 8.7), 0.04 µL dNTP mix (25 mM each), 5 U/µL Hot Star Taq (Qiagen). Primers were then added to a final concentration (each) of 1 µM and 1 µL bisulphite converted DNA (1 ng/µL per reaction). Reactions were incubated as follows: 94° C. for 15 minutes then 45 cycles of 94° C. for 20 seconds, 56° C. for 30 seconds (temperature adjusted according to primer Tm), 72° C. for 1 minute followed by 72° C. for 3 minutes. Reactions were then treated with Shrimp alkaline phosphatase (SAP), in vitro transcribed and analyzed according to the manufacturer's instructions (Sequenom). Fully methylated DNA controls were obtained from Millipore-(CpGenome™ Universal Methylated DNA, part number S7821).

Statistical Methods:

Each custom Agilent array was hybridized with an HpaII digested sample (HpaII+) against the same sample without HpaII digestion (HpaII−). This HpaII+/− hybridization is designed to detect hypomethylated MspI recognition sites. If the CpG dinucleotide in an MspI site recognition site is hypomethylated, the DNA segments containing this site will be digested by HpaII; thus the signal from the HpaII− sample should be stronger than the signal from the corresponding HpaII+ sample, which will be selectively digested by HpaII. In other words, the log signal ratio of HpaII− to HpaII+ should be positive. Based on this design, the MspI sites can be identified, where the CVS samples and the MBC samples have different methylation patterns in the following way:

First, MspI sites were identified that are hypomethylated in either the CVS samples or the MBC samples, but not in both. It can be tested if an MspI site is hypomethylated in a type of tissue by testing the log signal ratios of the probe targeting that site. If the log signal ratio of HpaII− to HpaII+ is significantly above 0, the MspI site is hypomethylated. Next, MspI sites were identified that were differentially methylated between CVS and MBC. This is done by testing if the log ratio of HpaII+/HpaII− for a probe is the same in both CVS and MBC. If the log ratio is significantly different, the MspI site is differentially methylated. The intersection of the two sets of MspI sites identified in the two previous steps is the set of MspI sets with tissue specific methylation patterns.

The statistical tests used were based on the empirical Bayesian method described in Smyth (Smyth, Sat. Appl. Genet. Mol. Biol. 3: Article 3, 2004), with false discovery rate (FDR) controlled at 5%. The data (green/red signal ratios) are normalized using the cyclic loss method (Bolstad et al., Bioinformatics 19: 185-193, 2003). All analyses were performed using the statistical computing package R.

Example 2

Detection of Methylated Sequences and Results

In order to generate a target library of DNA fragments that are enriched for methylated DNA sequences, an approach was used that takes advantage of the inability of HpaII, an isoschizomer of MspI, to cleave its CCGG recognition sequence when the central CpG dinucleotide of that core site is methylated (Shann et al., Gen. Res. 18: 791-801, 2008).

Pre-digestion of the sample DNA with TspRI generates a 9 bp overhang that renders the sample resistant to digestion by exonuclease III. However, exonuclease III is able to digest HpaII-generated 2 bp overhangs and so fragments that are unmethylated at HpaII (MspI) sites and therefore cleaved by this enzyme are lost from the fragment library after digestion with exonuclease III. Sham-digestion of a control library without HpaII provides a comparative analysis between HpaII-digested and sham-digested libraries for the high-throughput determination of DNA methylation status. This procedure is summarized in FIG. 1.

A custom microarray was designed such that every MspI site on chromosomes 13, 18 and 21 is represented by two flanking 60 bp oligonucleotide probes. Each array contains 215,060 informative probes. Among them, 78,548 probes target 42,978 MspI/HpaII sites in chr18, with 35,570 sites targeted by a matching pair of probes. Also, 46,675 probes target 25,878 MspI/HpaII sites in chr21, with 20,797 sites targeted by a matching pair of probes. Furthermore, 89,837 probes target 49285 MspI/HpaII sites in chr13, with 40,552 sites targeted by a matching pair of probes. The complete array design is provided in Supplementary File F1 of Chu et al., "A microarray based approach for the identification of epigenic biomarkers for the non-invasive diagnosis of fetal disease," Prenatal Diagnosis 29: 1020-1030, 2009, published on-line Jul. 31, 2009; the manuscript and the on-line supplementary information is incorporated by reference herein.

Each member of a probe pair matches one flanking sequence of an MspI recognition site whilst the other member of the pair matches the opposite flanking sequence. Thus two non-overlapping probes are present for every MspI site. To minimize false positive and negative results a pooling strategy was adopted for DNA samples prior to target library preparation in which two pools each of CVS and MBC were used, where each pool contained samples from four individuals respectively. technical replicate experiments were also carried out using a dye-swapping approach.

Using this approach, 6,311 MspI/HpaII sites were identified across all three chromosomes that were differentially methylated between CVS and MBCs and reached statistical significance under the criteria described in Materials and Methods. These included 1,272 sites on chromosome 21; 2,297 on chromosome 18; and 2,742 on chromosome 13 respectively. These can be considered to be tissue specific differentially methylated CpG sites (T-DMRs). Of these differentially methylated sites, 5,499 are hypomethylated in CVS versus MBC whereas only 812 are hypomethylated in MBC versus CVS. The entire list of T-DMRs is provided in Table S1 of Chu et al., "A microarray based approach for the identification of epigenic biomarkers for the non-invasive diagnosis of fetal disease," Prenatal Diagnosis 29: 1020-1030, 2009, published on-line Jul. 31, 2009; the manuscript and the on-line supplementary information is incorporated by reference herein.

Given that the diagnostic utility of methylation-specific quantitative analysis of fetal DNA requires that the target amplicon include a polymorphic marker for which the fetus is heterozygous (Tong et al., 2006), the data was analyzed for significant T-DMRs that are located within 150 bp of a known SNP. This is because the most attractive candidate T-DMRs will be adjacent to SNPs that are highly polymorphic and therefore common amongst target patient populations (Tong et al., 2006). Of the CpG sites hypomethylated in CVS relative to MBC, 888, 755 and 482 on chromosomes 13, 18 and 21 respectively, were found to be within 150 bp of a polymorphic SNP using a heterozygosity cut-off of 0.25. Similarly, of the CpG sites hypomethylated in MBC relative to CVS, 151, 115 and 107 were found to be within 150 bp of a polymorphic SNP using a heterozygosity cut-off of 0.25. The top 15 T-DMRs within 150 bp of a polymorphic SNP are shown in Table 1 and the full list, ranked by statistical significance, in Tables S2-1 through S2-6 of Chu et al., "A microarray based approach for the identification of epigenic biomarkers for the non-invasive diagnosis of fetal disease," Prenatal Diagnosis 29: 1020-1030, 2009, published on-line Jul. 31, 2009; the manuscript and the on-line supplementary information is incorporated by reference herein.

TABLE 1

T-DMRs within 150 bp of a polymorphic SNP determined by custom Agilent microarray analysis for chromosomes 21 (A and B), 18 (C and D) and 13 (E and F).

| SNP rs.id | Combined pval | Probe Unique ID | Probe Position |
|---|---|---|---|
| A. Hypomethylated in MBC Versus CVS on Chromosome 21 ||||
| 11702354 | 2.01E−13 | 202853 | chr21: 34806349-34806290 |
| 11702354 | 2.01E−13 | 13099 | chr21: 34806348-34806407 |
| 11702450 | 3.30E−12 | 15805 | chr21: 46528161-46528220 |
| 11702450 | 3.30E−12 | 107388 | chr21: 46528162-46528103 |
| 2839418 | 4.57E−11 | 88603 | chr21: 42192976-42193035 |
| 2839418 | 4.57E−11 | 172376 | chr21: 42192977-42192918 |
| 6517531 | 2.35E−10 | 172933 | chr21: 39559604-39559545 |
| 6517531 | 2.35E−10 | 172764 | chr21: 39559603-39559662 |
| 2824493 | 9.08E−10 | 130381 | chr21: 18087813-18087872 |
| 2824493 | 9.08E−10 | 115667 | chr21: 18087814-18087755 |
| 2835676 | 1.67E−09 | 195931 | chr21: 37513226-37513285 |
| 2835676 | 1.67E−09 | 74314 | chr21: 37513227-37513168 |
| 2823026 | 2.50E−09 | 170571 | chr21: 15346480-15346539 |
| 2823026 | 2.50E−09 | 125765 | chr21: 15346481-15346422 |
| 6517254 | 5.09E−09 | 120612 | chr21: 35002142-35002201 |
| 6517254 | 5.09E−09 | 105469 | chr21: 35002143-35002084 |
| 2070368 | 5.09E−09 | 105469 | chr21: 35002143-35002084 |
| 2070368 | 5.09E−09 | 120612 | chr21: 35002142-35002201 |
| 220269 | 5.55E−09 | 212124 | chr21: 42357349-42357290 |
| 220269 | 5.55E−09 | 165397 | chr21: 42357348-42357407 |
| B. Hypomethylated in CVS Versus MBC on Chromosome 21 ||||
| 225395 | 1.33E−14 | 31538 | chr21: 42559967-42560026 |
| 225395 | 1.33E−14 | 115974 | chr21: 42559968-42559909 |
| 2837528 | 2.52E−14 | 136995 | chr21: 40533598-40533539 |
| 2837528 | 2.52E−14 | 1216 | chr21: 40533597-40533656 |
| 2827557 | 1.33E−13 | 12999 | chr21: 22839640-22839581 |
| 2827557 | 1.33E−13 | 178006 | chr21: 22839639-22839698 |
| 2822564 | 9.55E−13 | 188482 | chr21: 14608183-14608242 |
| 2822564 | 9.55E−13 | 73052 | chr21: 14608184-14608125 |
| 233895 | 2.13E−12 | 85116 | chr21: 27247103-27247162 |
| 233895 | 2.13E−12 | 11559 | chr21: 27247104-27247045 |
| 9980448 | 3.89E−12 | 193547 | chr21: 42712730-42712789 |
| 9980448 | 3.89E−12 | 58155 | chr21: 42712731-42712672 |
| 2827384 | 3.07E−11 | 97870 | chr21: 22605322-22605263 |
| 2827384 | 3.07E−11 | 120832 | chr21: 22605321-22605380 |
| 2826052 | 6.62E−11 | 14852 | chr21: 20457190-20457249 |
| 2826052 | 6.62E−11 | 2381 | chr21: 20457191-20457132 |
| 9977149 | 1.02E−10 | 30513 | chr21: 15936203-15936144 |
| 9977149 | 1.02E−10 | 39772 | chr21: 15936202-15936261 |
| 3453 | 1.16E−10 | 145449 | chr21: 34741083-34741024 |
| 3453 | 1.16E−10 | 142382 | chr21: 34741082-34741141 |
| C. Hypomethylated in MBC Versus CVS on Chromosome 18 ||||
| 8083921 | 6.01E−12 | 90918 | chr18: 58916958-58917017 |
| 8083921 | 6.01E−12 | 189198 | chr18: 58916959-58916900 |
| 546680 | 5.81E−11 | 158354 | chr18: 30988045-30988104 |
| 546680 | 5.81E−11 | 76298 | chr18: 30988046-30987987 |
| 4891159 | 1.53E−10 | 48439 | chr18: 72230922-72230863 |
| 4891159 | 1.53E−10 | 89527 | chr18: 72230921-72230980 |
| 16978450 | 4.22E−10 | 211790 | chr18: 41517172-41517231 |
| 3786395 | 4.22E−10 | 211790 | chr18: 41517172-41517231 |
| 7245283 | 4.32E−10 | 174750 | chr18: 957430-957371 |
| 7245283 | 4.32E−10 | 169527 | chr18: 957429-957488 |
| 9945379 | 4.47E−10 | 57634 | chr18: 10928196-10928255 |
| 9945379 | 4.47E−10 | 52550 | chr18: 10928197-10928138 |

TABLE 1-continued

T-DMRs within 150 bp of a polymorphic SNP determined by custom Agilent microarray analysis for chromosomes 21 (A and B), 18 (C and D) and 13 (E and F).

| SNP rs.id | Combined pval | Probe Unique ID | Probe Position |
|---|---|---|---|
| 12958513 | 1.06E−09 | 28434 | chr18: 41520963-41521022 |
| 16978452 | 1.06E−09 | 28434 | chr18: 41520963-41521022 |
| 7228161 | 1.06E−09 | 28434 | chr18: 41520963-41521022 |
| 16978452 | 1.06E−09 | 41831 | chr18: 41520964-41520905 |
| 12958513 | 1.06E−09 | 41831 | chr18: 41520964-41520905 |
| 7228161 | 1.06E−09 | 41831 | chr18: 41520964-41520905 |
| 11875350 | 1.57E−09 | 50589 | chr18: 66307845-66307786 |
| 11152348 | 2.01E−09 | 118255 | chr18: 58349522-58349463 |
| D. Hypomethylated in CVS Versus MBC on Chromosome 18 | | | |
| 12955286 | 2.23E−14 | 197827 | chr18: 39459451-39459510 |
| 1852531 | 2.23E−14 | 197827 | chr18: 39459451-39459510 |
| 1852531 | 2.23E−14 | 111977 | chr18: 39459452-39459393 |
| 12955286 | 2.23E−14 | 111977 | chr18: 39459452-39459393 |
| 1244833 | 1.58E−13 | 206906 | chr18: 67161475-67161534 |
| 1244833 | 1.58E−13 | 100157 | Chr18: 67161476-67161417 |
| 2923220 | 3.66E−13 | 98530 | Chr18: 67061707-67061648 |
| 2923220 | 3.66E−13 | 114767 | Chr18: 67061706-67061765 |
| 16977803 | 7.31E−13 | 15847 | Chr18: 39904531-39904590 |
| 16977803 | 7.31E−13 | 13551 | Chr18: 39904532-39904473 |
| 603884 | 7.62E−13 | 6351 | Chr18: 50016366-50016425 |
| 603884 | 7.62E−13 | 155051 | Chr18: 50016367-50016308 |
| 4800573 | 8.57E−13 | 40020 | Chr18: 20313668-20313609 |
| 4800573 | 8.57E−13 | 165509 | Chr18: 20313667-20313726 |
| 12970409 | 9.62E−13 | 107335 | Chr18: 23756169-23756228 |
| 12970409 | 9.62E−13 | 97494 | Chr18: 23756170-23756111 |
| 11663168 | 1.10E−12 | 173600 | chr18: 910151-910092 |
| 11663172 | 1.10E−12 | 173600 | chr18: 910151-910092 |
| 11663172 | 1.10E−12 | 174485 | chr18: 910150-910209 |
| 11663168 | 1.10E−12 | 174485 | chr18: 910150-910209 |
| E. Hypomethylated in MBC Versus CVS on Chromosome 13 | | | |
| 7317471 | 6.71E−13 | 10348 | Chr13: 20518120-20518061 |
| 7317471 | 6.71E−13 | 44374 | Chr13: 20518119-20518178 |
| 3742160 | 5.09E−12 | 200018 | chr13: 105943751-105943810 |
| 3742160 | 5.09E−12 | 153614 | chr13: 105943752-105943693 |
| 206321 | 1.75E−11 | 94618 | Chr13: 31888677-31888736 |
| 206321 | 1.75E−11 | 2447 | Chr13: 31888678-31888619 |
| 9579199 | 2.41E−11 | 70801 | Chr13: 28062767-28062708 |
| 9578047 | 2.41E−11 | 70801 | Chr13: 28062767-28062708 |
| 9578047 | 2.41E−11 | 202671 | Chr13: 28062766-28062825 |
| 9579199 | 2.41E−11 | 202671 | Chr13: 28062766-28062825 |
| 9506534 | 2.82E−11 | 173211 | Chr13: 20145259-20145318 |
| 9506534 | 2.82E−11 | 72382 | Chr13: 20145260-20145201 |
| 1411551 | 8.55E−11 | 49844 | chr13: 109170896-109170837 |
| 1411551 | 8.55E−11 | 49787 | chr13: 109170895-109170954 |
| 4772302 | 1.50E−10 | 77302 | chr13: 99968298-99968239 |
| 9515119 | 5.74E−10 | 73274 | chr13: 109207221-109207162 |
| 9515119 | 5.74E−10 | 197654 | chr13: 109207220-109207279 |
| 9551454 | 1.09E−09 | 201286 | chr13: 27730895-27730954 |
| 9551454 | 1.09E−09 | 214291 | chr13: 27730896-27730837 |
| 17593586 | 2.72E−09 | 121914 | chr13: 40694042-40693983 |
| F. Hypomethylated in CVS Versus MBC on Chromosome 13 | | | |
| 9542537 | 2.39E−13 | 16916 | chr13: 70392637-70392696 |
| 9542537 | 2.39E−13 | 193406 | chr13: 70392638-70392579 |
| 7983181 | 3.47E−13 | 118841 | chr13: 82628956-82628897 |
| 7983181 | 3.47E−13 | 113031 | chr13: 82628955-82629014 |
| 166710 | 5.70E−13 | 2591 | chr13: 35186503-35186562 |
| 166710 | 5.70E−13 | 103271 | chr13: 35186504-35186445 |
| 9301803 | 6.28E−13 | 90142 | chr13: 91837064-91837005 |
| 9301804 | 6.28E−13 | 46449 | chr13: 9837063-91837122 |
| 9301804 | 6.28E−13 | 90142 | chr13: 91837064-91837005 |
| 9301803 | 6.28E−13 | 46449 | chr13: 91837063-91837122 |
| 2025675 | 1.06E−12 | 158650 | chr13: 70621925-70621984 |
| 2025675 | 1.06E−12 | 40595 | chr13: 70621926-70621867 |
| 11617606 | 2.44E−12 | 24847 | chr13: 109322585-109322526 |
| 11617606 | 2.44E−12 | 156269 | chr13: 109322584-109322643 |
| 9535813 | 3.74E−12 | 62282 | chr13: 51453087-51453146 |
| 9316563 | 3.74E−12 | 18480 | chr13: 51453088-51453029 |
| 9316563 | 3.74E−12 | 62282 | chr13: 51453087-51453146 |
| 9535813 | 3.74E−12 | 18480 | chr13: 51453088-51453029 |

TABLE 1-continued

T-DMRs within 150 bp of a polymorphic SNP determined by custom Agilent microarray analysis for chromosomes 21 (A and B), 18 (C and D) and 13 (E and F).

| SNP rs.id | Combined pval | Probe Unique ID | Probe Position |
|---|---|---|---|
| 980094 | 4.48E−12 | 156466 | chr13: 94960749-94960808 |
| 2389355 | 4.48E−12 | 19072 | chr13: 94960750-94960691 |

Figure 2A:
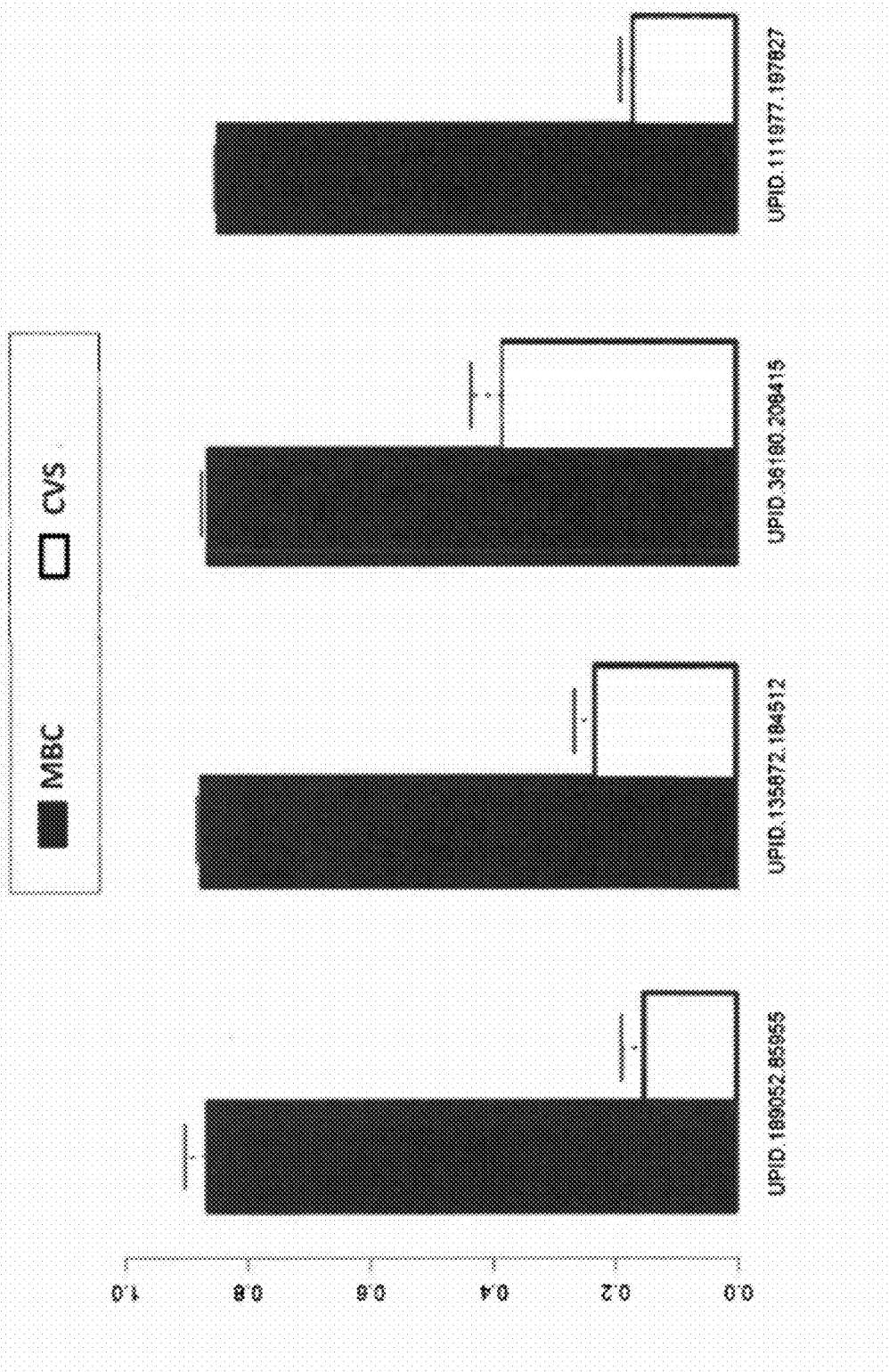
FIG. 2A-B is a set of graphs.
Figure 2B:
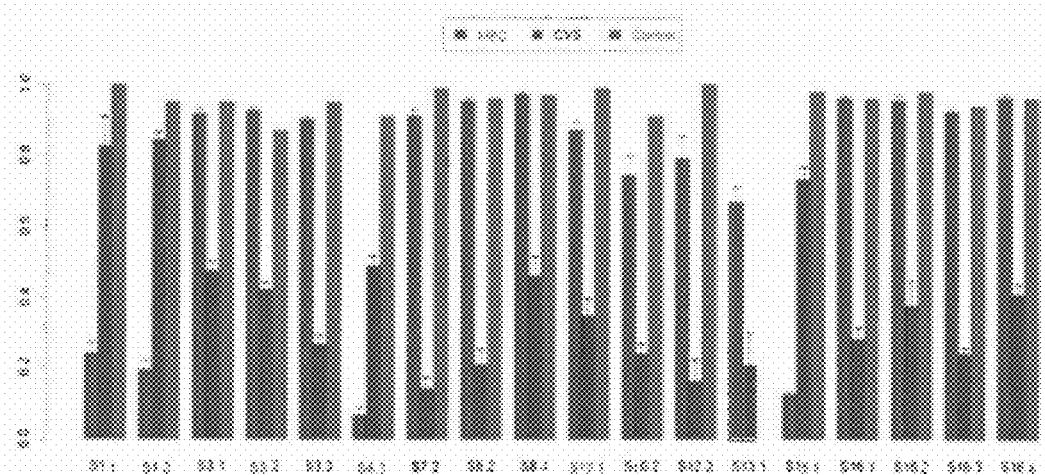

To confirm the accuracy of the microarray data, the differential methylation of a number of MspI sites was confirmed by pyrosequencing (FIG. 2A) and Mass Array/Epityper (FIG. 2B). Notably, a number of these sites are flanked by additional CpGs that are also differentially methylated, as indicated in FIG. 2B. Furthermore, of 14 CpG islands previously suggested to be good candidates for development as biomarkers for fetal aneuploidies on chromosome 21 (Chim et al., Clin. Chem. 54: 500-511, 2008), 70% are found in genes that we identified in our data as containing T-DMRs (Table 2).

TABLE 2

Comparison between previously identified chromosome 21 T-DMRs (Chim et al., supra, 2008) and current data

| | Gene Previously Identified as T-DMR (Chim et al., 2008) | T-DMR Identified by Current Study (probe unique ID) |
|---|---|---|
| Methylated in CVS and unmethylated in MBC | C21orf63 | Yes (30351) |
| | OLIG2 | No |
| | CBR1 | No |
| | SIM2 | Yes (72327) |
| | DSCAM | Yes (88779) |
| | TRPM2 | Yes (149601) |
| | C21orf29 | Yes (19822) |
| | COL18A1 | Yes (29860) |
| Unmethylated in CVS, methylated in MBC | RUNX1 | Yes (32873) |
| | PDE9A | Yes (49044) |
| | HIST1H2BK | No |
| | HSF2BP | Yes (98506) |
| | COL6A1 | Yes (107986) |
| | COL6A2 | Yes (135238) |

In this study, the first trimester placental DNA methylome at its maternal interface was evaluated to identify potential biomarkers for the minimally-invasive diagnosis of fetal genetic disease. Differentially methylated MspI recognition sequences (CCGG) on human chromosome 13, 18 and 21 were identified using DNA extracted from CVS compared to DNA from maternal leukocyte samples. This was achieved using a custom microarray designed for this purpose and novel computational and statistical methods.

Thus, a comprehensive analysis of DNA methylation differences between genomic DNA isolated from first trimester human placental samples at their maternal interface and gestational age-matched MBC samples was performed. These data provided candidate markers for further development in the context of fetal genetic diagnosis. These biomarkers are of use, as they exhibited differential methylation between CVS and MBCs and were found with 150 bp of highly polymorphic SNPs.

It was first demonstrated in 1997 that Y chromosome DNA derived from a male fetus can be detected by PCR in maternal plasma and serum (Lo et al., Am. J. Hum. Genet. 62: 768-775, 1998b). This minimally invasive approach requires only a maternal blood sample. Fetal DNA constitutes approximately 3-10% of total maternal plasma DNA and it has been shown that this frequency is increased both in aneuploid and preeclamptic pregnancies when compared to those that progress nominally (Lo et al., Clin. Chem. 45: 1747-51, 1999a, Lo et al., Clin. Chem. 45: 184-188, 1999b, Lun et al., Clin. Chem. 45: 1664-1672, 2008). Methods for the detection of specific sex-linked fetal DNA mutations (Costa et al., N. Engl. J. Med. 346: 1502, 2002) and paternally inherited Beta-thalassemia and achrondroplasia have been published (Li et al., JAMA 293: 843-849, 2005, Li et al., Prenat. Diagnosis 27: 11-172007) and a plasma-based DNA test to predict fetal Rhesus D blood group status is now widely used in clinical practice (Lo et al., NEJM 339: 1734-1738, 1998a).

Recently, differences in the methylation status of the RASSF1 and Maspin genes in the DNA of placental tissue and maternal hematopoetic cells have been exploited via methylation-specific PCR to selectively amplify fetal DNA sequences on chromosomes 3 and 18 respectively from maternal blood (Chim et al., PNAS 102: 14753-8, 2005, Chan et al., Clin. Chem. 52: 2211-2218, 2006). This approach has been shown to have diagnostic potential in the context of fetal disease in that elevated placental RASSF1 levels in maternal plasma have been shown in early pregnancy to be associated with an eventual diagnosis of preeclampsia (Tsui et al., Prenat. Diagn. 27: 1212-1218, 2007b) and Maspin may have potential for the detection of a subset of cases of trisomy 18 (Tong et al., Clin. Chem. 52: 2194-2202, 2006). One limitation to progression in this field, however, is the lack of comprehensive information relating to CpG sites that are differentially methylated between CVS and MBC (see Chim et al., Clin Chem. 54: 500-11, 2008). Provided herein is a comprehensive list of T-DMRs that exist between CVS and MBC on chromosomes with diagnostic significance in the context of fetal aneuploidy. Furthermore, within this context, sequences have been identified that detect aneuploidy in a fetus. These sequences are provided herein.

Example 3

Detection of Fetal Aneuploidy

Recruitment of Pregnant Individuals During Early Gestation:

Patients who are >35 years of age or have a family history of birth defects or genetic conditions are referred for genetic counseling as a matter of routine. During this consult they are generally offered amniocentesis or CVS depending on gestational age and preference. Regardless of whether they elect to undergo an invasive diagnostic procedure, the vast majority of these individuals receive a first trimester serum screen and an ultrasound for nuchal translucency. Patients who are <35 years of age and have no family history of birth defects or genetic conditions are not routinely scheduled for genetic counseling. Instead they undergo a first trimester serum screen and a nuchal translucency test. If the patient has an increased risk result, she is contacted by a genetic counselor and is offered a consult and diagnostic testing via amniocentesis or CVS. All study participants are drawn from the population of individuals undergoing informed consent and patient recruitment will take place in the Center for Medical Genetics. Should individuals who are consented elect not to undergo either CVS or amniocentesis, these deliveries are tracked through the GIS database (above) to obtain post-natal outcome data.

Data and Sample Tracking:

Each participant entering into the study is assigned a unique bar code, to be issued at the time of consent. This bar code is used to track the patient's blood sample, plasma-derived DNA, sequencing library and the resulting data and is linked to all available clinical and demographic information including diagnostic test results and birth outcome.

Separation of Plasma from Whole Blood:

Whole blood is centrifuged at 1600×g for 13 min at 4° C., setting acceleration and deceleration to 3. 1 ml aliquots of plasma are pipetted into 1.5 ml centrifuge tubes. Cellular debris is pelleted by centrifuging the plasma at 16000×g for 10 min at 4° C. 900 ul from each tube is pipetted into a clean 1.5 ml tube. Plasma aliquots are stored at −80° C.

DNA Extraction from Plasma:

DNA is extracted from plasma using the QIAMP® DNA mini kit (Qiagen) and supplied reagents. Briefly, 1 vial of frozen plasma is thawed to room temperature and split into two tubes. 40 ul of Qiagen Protease is added to each tube and the sample inverted 5 times to mix. 400 ul buffer AL is added to each tube and the sample vortexed for 15 sec. Samples are incubated at 56° C. for 10 min. 400 ul 100% ethanol is added to each tube and tubes are vortexed for 15 sec. 600 ul of mixture is applied to the spin column and centrifuged at 6000×g for 1 min, repeating this step as many times as necessary to get the entire plasma sample through the same column. The column is washed by adding 500 ul buffer AW and centrifuging for 1 min at 6000×g. The column is then washed again by adding 500 ul buffer AW2, and centrifuging for 4 min at maximum speed. To remove residual ethanol, the column is placed in a clean collection tube and centrifuged at maximum speed for 2 min. To elute the DNA, the column is placed in a 1.5 ml tube, 75 ul of RNase/DNase free water is added to the column, the column is incubated at room temp for 5 minutes and then centrifuged for 1 min at 6000×g.

Figure 3:
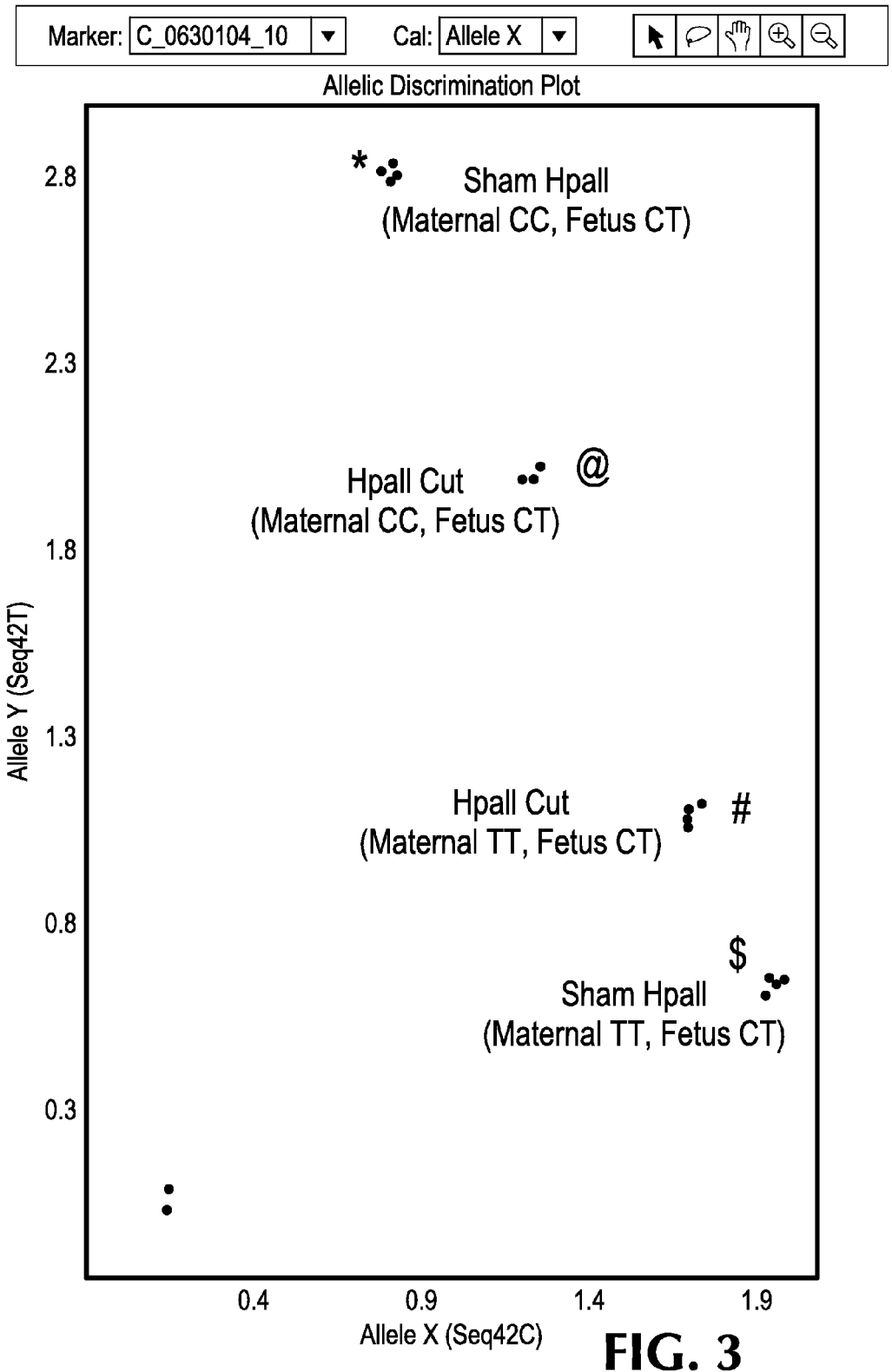
FIG. 3 is a presentation of data from a real time PCR analysis of two different maternal plasma samples. Each cluster of four dots represents 4 replicates for each condition. The cluster represented by the * is from maternal plasma DNA that was not cut with HpaII. Therefore there is no selection for fetal DNA and the overwhelming signal read by the instrument is the TT genotype. When this DNA is cut with HpaII the fetal DNA is preserved and the maternal DNA lost because it will not amplify (@). The bottom two clusters are from a second plasma sample. The lowest cluster is the uncut (sham) sample and clearly shows the maternal CC genotype (#). The higher of the two is the fetal genotype (CT) that has is detectable only after selection of fetal DNA via HpaII digestion ($). The nucleic acid sequence reference is SEQ ID NO: 1.

HpaII Digestion for Selection of Methylated DNA Loci:

DNA is combined with 4 ul 10× Fast Digestion Green buffer and 0.5 ul Fast Digest HpaII (Fermentas, Glen Burnie, Md.) in a 40 ul reaction volume and incubated at 37° C. for 5 min. An additional 0.5 ul Fast Digest HpaII is added and the mixture is incubated for another 5 min at 37 degrees. The reaction is then incubated at 70° C. for 5 minutes to heat inactivate the enzyme. For each sample, a mock digestion in which no HpaII was added is run simultaneously. Samples are then purified using Qiagen's MINELUTE® Reaction Clean-up Kit (Qiagen, Valencia, Calif.) as per the manufacturer's protocol. Each sample is combined with 300 ul buffer ERC, applied to a spin column and centrifuged at maximum speed for 1 min. The column is washed with 750 ul buffer PE and then transferred to a 1.5 ml tube. DNA is eluted by adding 10 ul water to the center of the spin column, incubating for 1 minute at room temperature and centrifuging at maximum speed for 1 min), see FIG. 3.

Bisulphite Treatment of DNA:

DNA can be bisulfite converted using the EZ DNA® Methylation Kit (Zymo Research, Irvine, Calif.) as per manufacturer's protocol. Briefly, 500 ng DNA is combined with 5 ul M-Dilution buffer in a total reaction volume of 50 ul and incubated at 37 degrees for 15 min. 100 ul of the CT Conversion Reagent is added and the mixture incubated at 50 degrees for 16 hr. After incubating on ice for 10 min, the sample is combined with 400 ul M-Binding Buffer in a spin column. The column is inverted several times to mix and then centrifuged at maximum speed for 30 sec. After washing the column with 100 ul M-Wash Buffer, 200 ul M-desulphonation buffer is added to the column and incubated at room temperature for 20 min. The column is centrifuged at maximum speed for 30 sec and then washed twice with 200 ul M-Wash Buffer. After transferring the column to a 1.5 ml tube, the DNA is eluted by adding 10 ul M-Elution Buffer and centrifuging at maximum speed for 30 sec.

MBD2 Protein Mediated Enrichment of Methylated DNA:

Enrichment of DNA by methylation status is performed using the METHYLMINER® Methylated DNA Enrichment Kit (Invitrogen, Carlsbad, Calif.) as per manufacturer's protocol. Briefly, 10 ul of DYNABEADS® M-280 Streptavidin beads is washed with 90 ul binding/wash buffer and then resuspended in 100 ul binding/wash buffer. 3.5 ug of MBD-Biotin Protein in 100 ul binding/wash buffer is combined with the beads, and the mixture is incubated at room temperature for 1 hr on a rotating mixer. The beads are washed three times in wash/binding buffer and then resuspended in 100 ul binding/wash buffer. Up to 1 ug fragmented DNA in 100 ul binding/wash buffer is combined with the beads, and this mixture is incubated on a rotating mixer for 1 hour at room temperature. The beads are collected against the side of the tube by a magnet and the supernatants removed. This fraction contains the non-methylated DNA. The beads are washed twice with 200 ul bind/wash buffer. The beads then are incubated in 200 ul 2M NaCl on a rotating mixer for 3 min at room temperature, collected against the side of the tube by a magnet and the supernatant containing the methylated DNA pipetted into a clean tube. The beads are incubated with an additional 200 ul 2M NaCl to ensure total collection of the methylated DNA. DNA is then purified and concentrated by ethanol precipitation and resuspended in water.

Enzymatic Enrichment of Methylated DNA Using TspRI and Exonuclease:

This method can be used prior to a gene/locus specific amplification or other enrichment step. This method selectively isolates methylated DNA fragments from a complex DNA sample. It is highly effective in this regard and can be used prior to simple amplification/enrichment and subsequent copy number analysis. Genomic DNA samples (3 μg) are digested for 2 hours at 37° C. with 50 U HpaII (New England Biolabs) in 904 total reaction volume using NEB buffer 4. A second aliquot of 50 U, 1 μL of buffer 4, and 44 water is added and digestion continued overnight (total reaction volume was 1004). Mock digestion controls are included to monitor digestion efficiency. Following overnight digestion, reactions are digested further with 5 uL (50 U) of TspRI (NEB) at 65° C. for three hours. Reactions are then incubated further with 75 U (0.75 μl) Exonuclease III (NEB) and incubated at 30° C. for 1 hour. Enzymatic activity is then nullified by heating at 70° C. for 20 min after which 50 U of RecJF (NEB) are added to remove single stranded DNA. Reactions are incubated for 30 min at 37° C. and inactivated at 65° C. for 20 min. Reactions are then phenol-chloroform extracted and the DNA precipitated and resuspended in 21.24 nuclease-free de-ionized water. Finally, extracted genomic DNA is quantified and assessed for purity using a NanoDrop ND-1000 UV-VIS Spectrophotometer.

Illumina DNA Sequencing Sample/DNA Library Preparation:

Plasma is separated from whole blood following centrifugation at 1,600×g for 10 minutes, followed by a second centrifugation to remove contaminating nucleated cells at 16,000×g for 10 minutes. DNA is extracted from plasma using the QIAAMP® DNA Blood Mini kit (Qiagen) and an Illumina sequencing library prepared as follows. The following oligos 5'—ACA CTC TTT CCC TAC ACG ACG CTC TTC CGA TC*T—3' (SEQ ID NO: 69) and 5'-/5Phos/GAT CGG AAG AGC TCG TAT GCC GTC TTC TGC TTG—3' (SEQ ID NO: 70) are resuspended in TE and annealed in 1×T4 DNA Ligase Reaction Buffer (NEW ENGLAND BIOLABS®, NEB) by heating at 95° C. for 5 minutes and then slowly cooled to room temperature for a final concentration of 36 mM annealed adaptor. Plasma DNA fragments is end repaired and then terminal A-residues added using the NEBNext End Repair and the NEBNext dA-tailing modules as per manufacturer's protocols (NEB). Following reaction cleanup using the MINELUTE® Cleanup kit (Qiagen), DNA fragments is combined with 0.5 uM adaptor and 400 U T4 DNA ligase (NEB) and incubated for 2 hours at 16° C. After reaction cleanup with MINELUTE® Cleanup kit, PCR is performed using the following primers: 5'—CAA GCA GAA GAC GGC ATA CGA GCT CTT CCG ATC*T—3' (SEQ ID NO: 71) and 5'—AAT GAT ACG GCG ACC ACC GAG ATC TAC ACT CTT TCC CTA CAC GAC GCT CTT CCG ATC*T—3' (SEQ ID NO: 72) and Phusion High-Fidelity DNA Polymerase (NEB). PCR conditions will include an initial denaturation (98° C. 30 s), 12 cycles of 98° C. for 10 s, 65° C. for 30 s and 72° C. for 30 s, with a final extension of 72° C. for 7 min. Following amplification, the PCR reaction is cleaned up using the MINELUTE® PCR Purification Kit (Qiagen).

Illumina DNA Sequencing Sample/DNA Library Preparation:

Plasma is separated from whole blood following centrifugation at 1,600×g for 10 minutes, followed by a second centrifugation to remove contaminating nucleated cells at 16,000×g for 10 minutes. DNA is extracted from plasma using the QIAAMP® DNA Blood Mini kit (Qiagen) and an Illumina sequencing library prepared as follows. The following oligos 5'—ACA CTC TTT CCC TAC ACG ACG CTC TTC CGA TC*T—3' (SEQ ID NO: 73) and 5'-/5Phos/GAT CGG AAG AGC TCG TAT GCC GTC TTC TGC TTG—3' (SEQ ID NO: 74) are resuspended in TE and annealed in 1×T4 DNA Ligase Reaction Buffer (NEB) by heating at 95° C. for 5 minutes and then slowly cooled to room temperature for a final concentration of 36 mM annealed adaptor. Plasma DNA fragments is end repaired and then terminal A-residues added using the NEB NEXT END REPAIR® and the NEBNEXT® dA-tailing modules as per manufacturer's protocols (NEB). Following reaction cleanup using the MINELUTE® Cleanup kit (Qiagen), DNA fragments are combined with 0.5 uM adaptor and 400 U T4 DNA ligase (NEB) and incubated for 2 hours at 16° C. After reaction cleanup with MINELUTE® Cleanup kit, PCR is performed using the following primers: 5'—CAA GCA GAA GAC GGC ATA CGA GCT CTT CCG ATC*T—3' (SEQ ID NO: 75) and 5'—AAT GAT ACG GCG ACC ACC GAG ATC TAC ACT CTT TCC CTA CAC GAC GCT CTT CCG ATC*T—3' (SEQ ID NO: 76) and PHUSION® High-Fidelity DNA Polymerase (NEB). PCR conditions include an initial denaturation (98° C. 30 s), 12 cycles of 98° C. for 10 s, 65° C. for 30 s and 72° C. for 30 s, with a final extension of 72° C. for 7 min. Following amplification, the PCR reaction is cleaned up using the MINELUTE® PCR Purification Kit (Qiagen).

Pyrosequencing:

Specific details of Pyrosequencing analysis vary depending on the context of the desired analysis. Examples \ of pyrosequencing based methods that are appropriate for digital analysis of locus-specific DNA copy number are provided below.

Library Preparation:

Prior to the following steps, a variety of methods can be utilized to generate targeted fetal DNA fragments on chromosomes of interest. Fragments are then processed as follows. Fragment ends are polished by incubation in polishing reaction (1× Polishing Buffer, dNTP's, ATP, polynucleotide kinase and T4 DNA polymerase) at 12° C. for 15 minutes and 25° C. for 15 minutes. Polished fragments are cleaned via a second MINELUTE® PCR purification column. Adapters 'A' and 'B' are ligated to the polished DNA fragments by incubation at 25° C. for 15 minutes. Ligation reaction is purified via MINELUTE® PCR purification column. DNA fragments with 2 'A' or 2 'B' adapters are removed using streptavidin coated library immobilization beads. 'B' adapters are biotinylated and thus adhere to the coated beads, while 'A' adapters do not. Fragments with 'A' adapters on both ends are washed away with BEAD WASH® buffer. Following bead washing DNA is denatured and the single unbound strand of 'A' adapter and 'B' complement is retained for future processing. Strands with 'B' adapters on both ends do not have an unbound strand and so are left on the beads at this point. A 1 ml aliquot of final single stranded product is run on a bioanalyzer RNA 6000 pico chip to assess size distribution and concentration.

emPCR:

sstDNA fragments are bound to library capture beads by mixing sample library with capture beads and performing the following thermocycler program: 80° C. for 5 minutes, ramp 0.1° C./sec to 70° C., hold at 70° C. for 1 minute, ramp 0.1° C./sec to 60° C., hold at 60° C. for 1 minutes, ramp 0.1° C./sec to 50° C. hold at 50° C. for 1 minute, ramp 0.1° C./sec to 20° C. Emulsion of PCR reagents in microreactors with library capture beads is prepared by mixing beads, PCR reaction mix (1× amplification mix, amplification primers, 0.15 U/ml PLATINUM TAQ® (Invitrogen)), and emulsion oil and mixing vigorously using a TISSUE LYSER® (Qiagen). Emulsion is distributed into a PCR plate and template amplification is carried out in a thermocycler using the following cycling conditions: Hotstart activation for 4 minutes at 94° C., 40 cycles of 94° C. for 30 seconds, 58° C. for 1 minute, 68° C. for 90 seconds followed by 13 cycles of 94° C. for 30 seconds and 58° C. for 6 minutes. Following template amplification, emulsions are broken and beads with amplified product recovered by repeated washes with ethanol using a syringe filter unit.

Bead Enrichment:

Enrichment beads are added to the recovered amplification beads. Enrichment beads are coated with oligos complementary to the free end of the amplified template. Successful amplification beads become bound to the paramagnetic enrichment beads and are drawn out of solution using a magnetic rack. Unsuccessful amplification beads are drawn off with the supernatant and discaraded. The bond between the amplification and enrichment beads is broken using 125 mM NaOH. Enrichment beads are pelleted using a magnetic rack and the enriched amplification beads are recovered. Melt solution is neutralized by repeated washes with 1× Annealing buffer and the beads left suspended in annealing buffer.

Sequencing primers are added to the mixture of beads and annealing buffer and annealed to the template using the following thermocycler conditions: 65° C. for 5 minutes, ramp to 50° C. at 0.1° C./second, hold at 50° C. for 1 minute, ramp to 40° C. at 0.1° C./second, hold at 40° C. for 1 minute, ramp to 15° C. at 0.1° C./second, hold 15° C. Beads are counted using a Beckman Z1 particle counter.

PICOTITERPLATE® Preparation:

Based on bead count obtained above and manufacturer recommendations for the PICOTITERPLATE® region size being used, control beads and sample beads are mixed to form the sequencing sample. Packing beads, sample beads and enzyme beads are applied to the PICOTITERPLATE® as per manufacturer instructions.

Sequencing Reaction:

The PICOTITERPLATE® is loaded onto the FLX® sequencer and the run started. The FLX® uses pyrosequencing chemistry and detects the incorporation of each nucleotide in real time.

emPCR Titration:

For each sample, a preliminary titration run must be performed in order to determine the best ratio of DNA template to amplification beads to obtain a maximum amount of usable sequence from the final data run. The concentration of DNA template is determined in copies/ml by applying the mass of the average fragment size as determined from the bioanalyzer output to the measured concentration of sstDNA library. emPCR reactions corresponding to titration points of 0.5, 2, 4 and 16 copies/bead are performed as described for emPCR above. Emulsions are broken and beads recovered. Amplification beads are not enriched but are counted and loaded onto a pico titer plate for sequencing analysis. The number of beads that can be successfully sequenced is used to determine the optimum ratio of DNA to beads for the final emPCR reaction to produce template for data production.

DNA Copy Number Analysis by Real Time PCR:

TAQMAN® Copy Number assays for each target gene as well as the TAQMAN® Copy Number Reference assay may be purchased from Applied Biosystems. For each real time PCR reaction, 10 ul 2× TAQMAN® Genotyping Master Mix, 1 ul 20× TAQMAN® Copy Number assay, 1 ul 20× TAQMAN® Copy Number Reference assay, 20 ng DNA and water are combined for a total reaction volume of 20 ul. Each sample is run in triplicate for quality control. Cycling conditions were 95 degrees for 10 min followed by 40 cycles of 95 degrees for 15 sec and 60 degrees for 1 min. The real time PCR reactions are read and analyzed using COPYCALLER® Software on the 7900HT Sequence Detection System (Applied Biosystems), see FIG. 3.

Tissue Handling and DNA Extraction:

DNA can be recovered from placental tissues or blood cells to confirm DNA methylation levels in pure sample. Placental samples are dissected under a microscope and separated from any decidua or flecks of blood. The culture media is removed and the tissue placed in 1.5-2.0 mL microcentrifuge tubes before freezing at −80° C. until DNA is extracted. To extract the DNA, one 5 mm stainless steel bead and 180 ul buffer ATL (from Qiagen's DNEASY® Blood and Tissue kit) were added to each CVS sample. The samples are placed in the TISSUELYSER® (Qiagen) Adaptor set 2×24, and the TISSUELYSER® operated for 20 seconds at 30 Hz. The DNA is then purified using the DNEASY® Blood and Tissue kit as per the manufacturer's protocol. MBCs are obtained between gestational weeks 11 and 13. DNA is extracted from the MBC's using a modified protocol previously described by Iovannisci, et al., 2006 (25), using reagents from the MASTUREPURE® DNA Purification Kit (Epincentre Technologies, Madison, Wis., Cat. No. MCD85201). Briefly, clotted blood (approximately 1 mL) is mixed with an equal volume (imp of 2× Tissue and Cell Lysis Solution, votexed for 10 s and combined with 2 mL Tissue and Cell Lysis Solution (MASTUREPURE® kit) containing 25 ng/µL proteinase K. 2 mL of MPC Protein Precipitation Reagent is added to the total volume (4 mL) of the lysed sample and vortex vigorously for 10-15 sec, after which samples are cooled on ice for 1 hour. Cell debris are then pelleted by centrifugation (×2) for at least 30 min at 2000 g and supernatants transferred to a new 50 mL conical tube. DNA is precipitated in 2 volumes of isoproponal, purified by phenol/chloroform extraction and resuspended in 50 µL DNAse/RNAse free water.

Quantification of Fetal DNA Frequency Using Real Time PCR:

To validate fetal DNA frequency in maternal plasma of samples in a clinical trial, Real Time PCR determination of fetal DNA concentration in maternal plasma is carried according to the method of Maron, et al (Maron, 2007) using the following primers:

```
SRY: Forward primer
                                     (SEQ ID NO: 77)
5'-TCCTCAAAAGAAACCGTGCAT-3'

Reverse primer
                                     (SEQ ID NO: 78)
5'-AGATTAATGGTTGCTAAGGACTGGAT-3'

Probe-
                                     (SEQ ID NO: 79)
5'-FAM-CACCAGCAGTAACTCCCCACAACCTCTTT-TAMRA-3'

B-globin: Forward primer
                                     (SEQ ID NO: 80)
5'-GTGCACCTGACTCCTGAGGAGA-3'

Reverse primer-
                                     (SEQ ID NO: 81)
5'-CCTTGATACCAACCTGCCCAG-3'

Probe-
                                     (SEQ ID NO: 82)
5'-FAM-AAGGTGAACGTGGATGAAGTTGGTGG-TAMRA-3'
```

B-globin is an ubiquitous housekeeping gene and is run concurrently with the SRY to ensure that DNA was present for each sample, irrespective of fetal gender. In order to estimate DNA concentration in the plasma DNA, a standard curve is run simultaneously alongside the plasma DNA sample. The standard curve DNA is prepared using commercially available DNA of known concentration. The range of values for the standard curve is approximately 6.4 µg/5 ul to 20,000 µg/5 ul. For each real time PCR reaction, 12.5 ul 2× TAQMAN® Universal PCR Master Mix, 1.25 ul 10 uM forward primer, 1.25 ul 10 uM reverse primer and 0.0625 ul 100 uM probe, 10 ul plasma DNA, 5 ul standards or 10 ul water (to serve as negative control) is added to the appropriate wells. Each plasma DNA sample and the negative control are run in triplicate. The standard curve DNA will also be run in triplicate. The thermal cycling conditions involve an initial denaturation step of 95° C. for 10 minutes, followed by 50 cycles of 95° C. for 15 sec and 60° C. for 1 min. The real time PCR reactions are performed using the 7900HT Sequence Detection System (Applied Biosystems).

Sequenom Epityper Analysis:

DNA methylation can be abalyzed in a quantitative fashion using the Mass Array method from SEQUENOM®. This is not suitable for digital chromosome copy number analysis but rather serves as a suitable method for confirming DNA methylation levels in samples of DNA. This method was used to validate results obtained by microarray based discovery (Chu et al., 2009, supra) of differentially methylated fetal versus maternal DNA. PCR reactions are carried out in a 384 well format as follows. To each reaction is added 1.42 µL ddH$_2$O, 0.54 µL 10× HOT STAR® Buffer (Qiagen) (15 mM MgCl$_2$, Tris-Cl, KCl, (NH$_4$)$_2$SO4, pH 8.7), 0.044 dNTP mix (25 mM each), 5 U/µL HOT STAR® Taq (Qiagen). Primers are then added to a final concentration (each) of 1 µM and 14 bisulphite converted DNA (1 ng/4 per reaction). Reactions are incubated as follows: 94° C. for 15 minutes then 45 cycles of 94° C. for 20 seconds, 56° C. for 30 seconds (temperature adjusted according to primer Tm), 72° C. for 1 minute followed by 72° C. for 3 minutes. Reactions are then treated with Shrimp alkaline phosphatase (SAP), in vitro transcribed and analyzed according to the manufacturer's instructions (Sequenom). Fully methylated DNA controls are obtained from Millipore-(CpGenome Universal Methylated DNA, part number S7821).

It is apparent that the precise details of the methods or compositions described may be varied or modified without departing from the spirit of the described invention. We claim all such modifications and variations that fall within the scope and spirit of the claims below.

The invention claimed is:

1. A method of detecting aneuploidy of chromosome 21 in human fetal genomic DNA from a human fetus, comprising:
   (a) obtaining purified human fetal genomic DNA from a human maternal biological sample comprising fetal genomic DNA and maternal DNA, comprising separating a fetal CpG-containing genomic sequence from chromosome 21 comprising at least 15 consecutive nucleotides of SEQ ID NO: 1 comprising the CpG at position 153-154 from said maternal DNA, wherein the CpG at position 153-154 is not methylated on said maternal DNA and is methylated on said fetal DNA; and
   (b) detecting an aneuploid copy number of the CpG-containing genomic sequence from chromosome 21 in the purified human fetal genomic DNA obtained in step (a).

2. The method of claim 1, wherein detecting the aneuploid copy number of the CpG-containing genomic sequence comprises detecting an allelic ratio of a bi-allelic single nucleotide polymorphism in the purified human fetal genomic DNA, wherein an allelic ratio of 1:2 or 2:1 is detected.

3. The method of claim 2, wherein SEQ ID NO: 1 comprises the single nucleotide polymorphism.

4. The method of claim 1, wherein detecting the aneuploid copy number of the CpG-containing genomic sequence comprises detecting an allelic ratio of a biallelic short tandem repeat polymorphism in the purified human fetal genomic DNA, wherein an allelic ratio of other than 1:1 is detected.

5. The method of claim 1, wherein obtaining purified human fetal genomic DNA from a human maternal biological sample comprises the use of a microarray.

6. The method of claim 1, wherein obtaining purified human fetal genomic DNA from a human maternal biological sample comprises the use of a restriction enzyme that differentially cleaves methylated or unmethylated DNA.

7. The method of claim 6, wherein the restriction enzyme is Hpa II.

8. The method of claim 1, wherein obtaining purified human fetal genomic DNA from a human maternal biological sample comprises the use of bisulfite.

9. The method of claim 1, further comprising amplifying the purified human fetal genomic DNA.

10. The method of claim 1, wherein obtaining purified human fetal genomic DNA from a human maternal biological sample comprises separating a fetal CpG-containing genomic sequence from chromosome 21 comprising SEQ ID NO: 1.

11. The method of claim 1, wherein detecting an aneuploid copy number comprises at least one of 1) DNA amplification; 2) detecting a fluorescent signal; 3) detecting hybridization of a probe; and 4) DNA sequencing.

12. The method of claim 1, wherein the aneuploidy is trisomy 21.

13. The method of claim 1, wherein the human maternal biological sample is a maternal blood sample.

14. The method of claim 1, wherein the human fetus is between 11 and 13 weeks of age.

15. The method of claim 1, further comprising karyotyping the human fetus.

* * * * *